US011781156B2

(12) United States Patent
Yang et al.

(10) Patent No.: US 11,781,156 B2
(45) Date of Patent: Oct. 10, 2023

(54) PLAKOPHILLIN-2 GENE THERAPY METHODS AND COMPOSITIONS

(71) Applicant: Tenaya Therapeutics, Inc., South San Francisco, CA (US)

(72) Inventors: Zhihong Jane Yang, Menlo Park, CA (US); Jaclyn Ho, San Mateo, CA (US); Chris Reid, San Bruno, CA (US); Jin Yang, Belmont, CA (US)

(73) Assignee: TENAYA THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 17/390,395

(22) Filed: Jul. 30, 2021

(65) Prior Publication Data

US 2022/0112517 A1 Apr. 14, 2022

Related U.S. Application Data

(60) Provisional application No. 63/216,322, filed on Jun. 29, 2021, provisional application No. 63/172,053, filed on Apr. 7, 2021, provisional application No. 63/089,951, filed on Oct. 9, 2020.

(51) Int. Cl.

| | |
|---|---|
| *A01N 63/00* | (2020.01) |
| *C12N 15/86* | (2006.01) |
| *A61P 9/00* | (2006.01) |
| *C07K 14/47* | (2006.01) |
| *A61K 48/00* | (2006.01) |

(52) U.S. Cl.
CPC .......... *C12N 15/86* (2013.01); *A61K 48/0058* (2013.01); *A61P 9/00* (2018.01); *C07K 14/47* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,797,368 A | 1/1989 | Carter et al. |
| 4,962,091 A | 10/1990 | Eppstein et al. |
| 5,139,941 A | 8/1992 | Muzyczka et al. |
| 5,449,614 A | 9/1995 | Danos et al. |
| 5,591,624 A | 1/1997 | Barber et al. |
| 5,817,491 A | 10/1998 | Yee et al. |
| 5,834,256 A | 11/1998 | Finer et al. |
| 5,928,906 A | 7/1999 | Koster et al. |
| 5,994,136 A | 11/1999 | Naldini et al. |
| 6,013,516 A | 1/2000 | Verma et al. |
| 6,156,303 A | 12/2000 | Russell et al. |
| 6,306,434 B1 | 10/2001 | Hong et al. |
| 6,872,528 B2 | 3/2005 | Klatzmann et al. |
| 6,910,434 B2 | 6/2005 | Lundgren |
| 6,962,815 B2 | 11/2005 | Bartlett |
| 6,984,517 B1 | 1/2006 | Chiorini et al. |
| 6,995,009 B1 | 2/2006 | Kitamura et al. |
| 7,070,994 B2 | 7/2006 | Barber et al. |
| 7,105,345 B2 | 9/2006 | Wilson et al. |
| 7,198,951 B2 | 4/2007 | Gao et al. |
| 7,259,151 B2 | 8/2007 | Arbetman et al. |
| 7,718,424 B2 | 5/2010 | Chiorini et al. |
| 7,790,449 B2 | 9/2010 | Gao et al. |
| 7,867,484 B2 | 1/2011 | Samulski et al. |
| 7,906,111 B2 | 3/2011 | Wilson et al. |
| 8,119,119 B2 | 2/2012 | Mallet et al. |
| 8,524,446 B2 | 9/2013 | Gao et al. |
| 8,784,799 B2 | 7/2014 | Samulski et al. |
| 8,999,678 B2 | 4/2015 | Vandenberghe et al. |
| 9,169,494 B2 | 10/2015 | Hewitt et al. |
| 9,233,131 B2 | 1/2016 | Schaffer et al. |
| 9,434,928 B2 | 9/2016 | Mendell et al. |
| 9,447,433 B2 | 9/2016 | Hirsch et al. |
| 9,737,618 B2 | 8/2017 | Wilson et al. |
| 9,783,824 B2 | 10/2017 | Kay et al. |
| 10,046,016 B2 | 8/2018 | Schaffer et al. |
| 10,485,883 B2 | 11/2019 | Wilson et al. |
| 10,526,617 B2 | 1/2020 | Gao et al. |
| 2003/0022870 A1* | 1/2003 | Dzau ...................... A61K 45/06 514/152 |
| 2007/0161031 A1 | 7/2007 | Trinklein et al. |
| 2011/0104679 A1 | 5/2011 | DeAngelis et al. |
| 2011/0296544 A1 | 12/2011 | Domon et al. |
| 2016/0022836 A1 | 1/2016 | Banfi et al. |
| 2016/0340393 A1 | 11/2016 | Schaffer et al. |
| 2018/0066285 A1 | 3/2018 | Ojala et al. |
| 2018/0360992 A1* | 12/2018 | Patel ...................... C12N 15/62 |

(Continued)

FOREIGN PATENT DOCUMENTS

| | | |
|---|---|---|
| JP | 2017514813 A | 6/2017 |
| WO | WO-9303769 A1 | 3/1993 |

(Continued)

OTHER PUBLICATIONS

Asokan (Human Gene Therapy, 24: 1-8, 2013). (Year: 2013).*
Cruz (JACC, 65(14): 1-13, 2015). (Year: 2015).*
Chamberlain (Current Opinion in Cardology, 32(3): 1-14, 2017). (Year: 2017).*
Cerrone (Nature Communications, 8(6): 1-16, 2017). (Year: 2017).*
Mauro (BioDrugss 32: 1-13, 2018) (Year: 2018).*
Akdis et al. Myocardial expression profiles of candidate molecules in patients with arrhythmogenic right ventricular cardiomyopathy/dysplasia compared to those with dilated cardiomyopathy and healthy controls. Heart Rhythm 13(3):731-741 (2016).
Ali et al. Adeno-associated virus gene transfer to mouse retina. Hum Gene Ther 9:81-86 (1998).

(Continued)

*Primary Examiner* — Michael C Wilson
(74) *Attorney, Agent, or Firm* — WILSON SONSINI GOODRICH & ROSATI

(57) ABSTRACT

Provided herein are methods and compositions for plakophilin-2 gene therapy for treating heart diseases such as arrhythmogenic right ventricular cardiomyopathy (ARVC) or arrhythmogenic cardiomyopathy (ACM).

17 Claims, 29 Drawing Sheets

Specification includes a Sequence Listing.

(56) References Cited

U.S. PATENT DOCUMENTS

| | | |
|---|---|---|
| 2019/0241622 A1 | 8/2019 | Ito et al. |
| 2021/0024956 A1 | 1/2021 | Sheikh et al. |
| 2022/0168446 A1 | 6/2022 | Herzog et al. |
| 2022/0168447 A1 | 6/2022 | Herzog et al. |
| 2023/0041648 A1 | 2/2023 | Yang et al. |
| 2023/0051968 A1 | 2/2023 | Yang et al. |
| 2023/0056066 A1 | 2/2023 | Yang et al. |

FOREIGN PATENT DOCUMENTS

| | | | |
|---|---|---|---|
| WO | WO-9309239 A1 | 5/1993 | |
| WO | WO-9319191 A1 | 9/1993 | |
| WO | WO-9407529 A1 | 4/1994 | |
| WO | WO-9412649 A2 | 6/1994 | |
| WO | WO-9428938 A1 | 12/1994 | |
| WO | WO-9500655 A1 | 1/1995 | |
| WO | WO-9511984 A2 | 5/1995 | |
| WO | WO-0183692 A2 | 11/2001 | |
| WO | WO-2007078599 A2 | 7/2007 | |
| WO | WO-2008021290 A2 * | 2/2008 | ......... G01N 33/6845 |
| WO | WO-2015162161 A1 | 10/2015 | |
| WO | WO-2016133917 A1 | 8/2016 | |
| WO | WO-2018222503 A1 | 12/2018 | |
| WO | WO-2019060454 A2 | 3/2019 | |
| WO | WO-2019207132 A1 | 10/2019 | |
| WO | WO-2020193698 A1 | 10/2020 | |
| WO | WO-2020205889 A1 | 10/2020 | |
| WO | WO-2021053222 A1 * | 3/2021 | ......... C07K 14/4716 |
| WO | WO-2021187380 A1 | 9/2021 | |
| WO | WO-2022032226 A1 | 2/2022 | |
| WO | WO-2022076648 A1 | 4/2022 | |
| WO | WO-2022195074 A2 | 9/2022 | |

OTHER PUBLICATIONS

Ali et al. Gene transfer into the mouse retina mediated by an adeno-associated viral vector. Hum Mol Genet 5:591-594 (1996).
Asimaki et al. A New Diagnostic Test for Arrhythmogenic Right Ventricular Cardiomyopathy. N Engl J Med 360(11):1075-84 (2009).
Asokan et al. An emerging adeno-associated viral vector pipeline for cardiac gene therapy. Hum Gene Ther. 24:906-13 (2013).
Balaji et al. Pseudotyped adeno-associated viral vectors for gene transfer in dermal fibroblasts: implications for wound-healing applications. J Surg Res. 184:691-98 (2013).
Bennett et al. Real-time, noninvasive in vivo assessment of adeno-associated virus-mediated retinal transduction. Invest Ophthalmol Vis Sci. 38(13):2857-2863 (1997).
Bitter et al. Expression and secretion vectors for yeast. Methods Enzymol 153:516-544 (1987).
Blomer et al. Highly efficient and sustained gene transfer in adult neurons with a lentivirus vector. J Virol. 71(9):6641-6649 1997.
Borras et al. Adenoviral reporter gene transfer to the human trabecular meshwork does not alter aqueous humor outflow. Relevance for potential gene therapy of glaucoma. Gene Ther 6(4):515-524 (1999).
Brodehl et al. Human Induced Pluripotent Stem-Cell-Derived Cardiomyocytes as Models for Genetic Cardiomyopathies. Int. J. Mol. Sci. 20:4381 (2019).
Brodehl et al. Molecular insights into cardiomyopathies associated with desmin (DES) mutations. Biophysical Reviews 10:983-1006 (2018).
Cerrone et al. Plakophilin-2 is required for transcription of genes that control calcium cycling and cardiac rhythm. Nat Commun 8(1):106 (2017).
Cotten et al. High-efficiency receptor-mediated delivery of small and large (48 kilobase gene constructs using the endosome-disruption activity of defective or chemically inactivated adenovirus particles. PNAS USA 89(13):6094-6098 (1992).
Curiel et al. High-efficiency gene transfer employing adenovirus-polylysine-DNA complexes. Nat Immun 13(2-3):141-64 (1994).
De et al. High levels of persistent expression of alpha1-antitrypsin mediated by the nonhuman primate serotype rh. 10 adeno-associated virus despite preexisting immunity to common human adeno-associated viruses. Mol. Ther. 13(1):67-76 (2006).
Dull et al. A third-generation lentivirus vector with a conditional packaging system. J Virol 71(11):8463-8471 (1998).
Flannery et al. Efficient photoreceptor-targeted gene expression in vivo by recombinant adeno-associated virus. PNAS USA 94(13):6916-6921 (1997).
Flotte et al. Stable in vivo expression of the cystic fibrosis transmembrane conductance regulator with an adeno-associated virus vector. PNAS USA 90(22):10613-10617 (1993).
Franz et al. Analysis of tissue-specific gene delivery by recombinant adenoviruses containing cardiac-specific promoters. Cardiovasc. Res. 35:560-566 (1997).
Gao et al.: Clades of Adeno-associated viruses are widely disseminated in human tissues. J Virol. 78(12): 6381-6388 (2004).
Gerull et al. Genetic Animal Models for Arrhythmogenic Cardiomyopathy. Front Physiol 11:624 (2020).
Green et al. Desmosomes: Essential contributors to an integrated intercellular junction network. F1000Res F1000 Faculty Rev-2150 (2019).
Hunter et al. Targeting gene expression to specific cardiovascular cell types in transgenic mice. Hypertension 22:608-617 (1993).
Jomary et al. Rescue of photoreceptor function by AAV-mediated gene transfer in a mouse model of inherited retinal degeneration. Gene Ther. 4(7):683-690 (1997).
Kanegae et al. Efficient gene activation in mammalian cells by using recombinant adenovirus expressing site-specific Cre recombinase. Nucleic Acids Res 23:3816-3821 (1995).
Kelleher et al. Long-term episomal gene delivery in human lymphoid cells using human and avian adenoviral-assisted transfection. Biotechniques 17(6):1110-7 (1994).
Kimatura et al. Retrovirus-mediated gene transfer and expression cloning: powerful tools in functional genomics. Exp Hematol 31:1007-1014 (2003).
Kotterman et al. Engineering adeno-associated viruses for clinical gene therapy. Nature reviews Genetics 15:445-451 (2014).
Lee et al. Adenovirus-Mediated Gene Delivery: Potential Applications for Gene and Cell-Based Therapies in the New Era of Personalized Medicine. Genes Dis 4(2):42-63 (2017).
Li et al. In vivo transfer of a reporter gene to the retina mediated by an adenoviral vector. Invest Opthalmol Vis Sci 35:2543-2549 (1994).
Li et al. Phenotype correction in retinal pigment epithelium in murine mucopolysaccharidosis VII by adenovirus-mediated gene transfer. PNAS USA 92:7700-7704 (1995).
Linn et al. Conservation of an AE3 Cl-/HCO3-exchanger cardiac-specific exon and promoter region and AE3 mRNA expression patterns in murine and human hearts. Circ. Res. 76:584-591 (1995).
Mann et al. Construction of a retrovirus packaging mutant and its use to produce helper-free defective retrovirus. Cell 33:153-159 (1983).
Marsic et al. Vector design Tour de Force: integrating combinatorial and rational approaches to derive novel adeno-associated virus variants. Mol. Therapy. 22(11):1900-1009 (2014).
Mendelson et al. Expression and rescue of a nonselected marker from an integrated AAV vector. Virology 166(1):154-165 (1988).
Miller et al. Radiation resistance in a doxorubicin-resistant human fibrosarcoma cell line. Am. J. Clin. Oncol. 15(3):216-221 (1992).
Miyoshi et al. Development of a self-inactivating lentivirus vector. J. Virol 72(10):8150-8157 (1998).
Miyoshi et al. Stable and efficient gene transfer into the retina using an HIV-based lentiviral vector. PNAS USA 94(19):10319-10323 (1997).
Moncayo-Arlandi et al. Unmasking the molecular link between arrhythmogenic cardiomyopathy and Brugada syndrome. Nat Rev Cardiol 14(12):744-756 (2017).
Morgenstern et al. Advanced mammalian gene transfer: high titre retroviral vectors with multiple drug selection markers and a complementary helper-free packaging cell line. Nucleic Acids Res. 18(12):3587-3596 (1990).

(56) References Cited

OTHER PUBLICATIONS

Mori et al. Two novel adeno-associated viruses from cynomolgus monkey: pseudotyping characterization of capsid protein. Virology 330(2):375-383 (2004).
Morita et al. Plat-E: an efficient and stable system for transient packaging of retroviruses. Gene Therapy 7(12):1063-1066 (2000).
Mura et al. Identification of a PKP2 gene deletion in a family with arrhythmogenic right ventricular cardiomyopathy. Eur J Hum Genet 21(11):1226-1231 (2003).
Muzyczka et al. Use of Adeno-Associated Virus as a General Transduction Vector for Mammalian Cells. Curr Top Microbiol Immunol 158:97-129 (1992).
Naldini et al. In vivo gene delivery and stable transduction of nondividing cells by a lentiviral vector. Science 272:263-7 (1996).
Naldini et al. Lentiviruses as gene transfer agents for delivery to non-dividing cells. Curr Opin Biotechnol. 9(5):457-463 (1998).
Nicolas et al. Chapter 25: Retroviral Vectors. In Vectors: A survey of molecular cloning vectors and their uses Rodriguez and Denhardt eds. Stoneham: Butterworth (pp. 494-513) (1988).
Onishi et al. Applications of retrovirus-mediated expression cloning. Exp Hematol 24:324-329 (1996).
Parmacek et al. A novel myogenic regulatory circuit controls slow/cardiac troponin C gene transcription in skeletal muscle. Mol Cell Biol 14:1870-1885 (1994).
Paskind et al. Dependence of Moloney murine leukemia virus production on cell growth. Virology 67:242-248 (1975).
Piras et al. Systemic injection of AAV9 carrying a periostin promoter targets gene expression to a myofibroblast-like lineage in mouse hearts after reperfused myocardial infarction. Gene Therapy 23:469-478 (2016).
Pozsgai et al. Systemic AAV-Mediated β-Sarcoglycan Delivery Targeting Cardiac and Skeletal Muscle Ameliorates Histological and Functional Deficits in LGMD2E Mice. Mol Ther. 25:855-69 (2017).
Riviere et al. Effects of retroviral vector design on expression of human adenosine deaminase in murine bone marrow transplant recipients engrafted with genetically modified cells. PNAS USA 92(15):6733-6737 (1995).
Robbins et al. In vivo definition of a cardiac specific promoter and its potential utility in remodeling the heart. Ann. N.Y. Acad. Sci.752:492-505 (1995).
Rolling et al. Evaluation of adeno-associated virus-mediated gene transfer into the rat retina by clinical fluorescence photography. Hum Gene Ther 10:641-648 (1999).
Sakamoto et al. A vitrectomy improves the transfection efficiency of adenoviral vector-mediated gene transfer to Müller cells. Gene Ther. 5(8):1088-1097 (1998).
Samulski et al. Helper-free stocks of recombinant adeno-associated viruses: normal integration does not require viral gene expression. J Virol. 63(9):3822-3828 (1989).
Sartorelli et al. Myocardial activation of the human cardiac alpha-actin promoter by helix- loop-helix proteins. PNAS USA 89:4047-4051 (1992).
Srivastava et al. Nucleotide sequence and organization of the adeno-associated virus 2 genome. J. Virol. 45:555-564 (1983).
Takahashi et al. Rescue from photoreceptor degeneration in the rd mouse by human immunodeficiency virus vector-mediated gene transfer. J Virol 73:7812-7816 (1999).
Temin. Chapter 6: Retrovirus Vectors for Gene Transfer: Efficient Integration into and Expression of Exogenous DNA in Vertebrate Cell Genomes. Gene Transfer Kucherlapati (ed.) New York: Plenum Press (pp. 149-188) (1986).
Wang et al. Diagnostic and therapeutic strategies for arrhythmogenic right ventricular dysplasia/cardiomyopathy patient. Europace 21(1):9-21 (2018).
Yee et al. A General Method for the Generation of High-Titer, Pantropic Retroviral Vectors: Highly Efficient Infection of Primary Hepatocytes. PNAS USA 91:9564-9568 (1994).
Zufferey et al. Multiply attenuated lentiviral vector achieves efficient gene delivery in vivo. Nat Biotechnol 15(9):871-875 (1997).
PCT/US2021/053908 Invitation to Pay Additional Fees dated Jan. 5, 2022.
Burke et al. Arrhythmogenic right ventricular cardiomyopathy and fatty replacement of the right 75ventricular myocardium: are they different diseases? Circulation 97(16):1571-1580 (1998).
PCT/US2021/053908 International Search Report and Written Opinion dated Mar. 16, 2022.
U.S. Appl. No. 17/882,314 Office Action dated Dec. 30, 2022.
U.S. Appl. No. 17/882,395 Office Action dated Dec. 30, 2022.
U.S. Appl. No. 17/882,314 Office Action dated Apr. 6, 2023.
U.S. Appl. No. 17/882,395 Office Action dated Apr. 6, 2023.
Presnyak et al. Codon optimality is a major determinant of mRNA stability. Cell 160(6):1111-1124 (2015).
Wu et al. Cardiac AAV:PKP2 Gene Therapy Reduces Ventricular Arrhythmias, Reverses Adverse Right Ventricular Remodeling, Improves Heart Function, and Extends Survival in a Pkp2-deficient Mouse Model of Arrhythmogenic Right Ventricular Cardiomyopathy Cardiac AAV:PKP2 Gene Therapy Improves Symptoms of ARVC and E. Poster (2022) Retrieved from the Internet: URL:https://www.tenayatherapeutics.com/wp-content/uploads/PKP2-Gene-Therapy-for-Arrhythmogenic-Right-Ventricular-Cardiomyopathy.pdf [retrieved on Jul. 17, 2023].

* cited by examiner

PLAKOPHILLIN-2 GENE THERAPY METHODS AND COMPOSITIONS

CROSS REFERENCE

This patent application claims the benefit of U.S. Provisional Application No. 63/089,951, filed Oct. 9, 2020, U.S. Provisional Application No. 63/172,053, filed Apr. 7, 2021, and U.S. Provisional Application No. 63/216,322, filed Jun. 29, 2021, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Aug. 30, 2021, is named 50971-701_201_SL.txt and is 38,735 bytes in size.

BACKGROUND

Arrhythmogenic right ventricular cardiomyopathy (ARVC) or arrhythmogenic cardiomyopathy (ACM) is an inherited cardiac disease found in 1/2000 to 1/5000 people. ARVC is characterized by fibrofatty tissue replacement, myocardial atrophy, predominant right ventricular dilation, ventricular arrhythmias, and sudden cardiac death (Wang et al., 2018). The disease is difficult to diagnose by conventional imaging and ECG particularly at its early stage due to its subclinical presentations. At the late stage, the disease progresses to more overt manifestations such as ventricular arrhythmias and morphological abnormalities in the ventricle. Sudden cardiac arrest in the young and athletes is found to be associated with ARVC and exercise-related cardiac wall stress. So far, there is no effective treatment of ARVC (Wang et al., 2018).

SUMMARY

In one aspect, there are provided methods for treating a heart disease or disorder in an individual in need thereof. In some embodiments, the method comprises administering a composition comprising (a) a gene therapy vector comprising a nucleic acid encoding a plakophilin 2 (PKP2) polypeptide or a fragment thereof operatively linked to a promoter and a 3' element; and (b) a pharmaceutically acceptable carrier or excipient. In some embodiments, the gene therapy vector comprises a viral vector selected from the group consisting of an adeno-associated virus, an adenovirus, a lentivirus, a pox virus, a vaccinia virus, or a herpes virus. In some embodiments, the gene therapy vector is an adeno-associated virus. In some embodiments, the adeno-associated virus is selected from the group consisting of an AAV6, an AAV8, and an AAV9. In some embodiments, the adeno-associated virus is an AAV9 having a nucleic acid sequence with at least 95% identity to SEQ ID NO: 7. In some embodiments, the heart disease or disorder is arrhythmogenic right ventricular cardiomyopathy (ARVC) or arrhythmogenic cardiomyopathy (ACM). In some embodiments, the promoter is a promoter that causes expression in tissues including the heart or a cardiac specific promoter. In some embodiments, the cardiac specific promoter is a PKP2 promoter, a troponin promoter, or an alpha-myosin heavy chain promoter. In some embodiments, the PKP2 promoter has a nucleic acid sequence having at least 95% identity to SEQ ID NO: 4. In some embodiments, the troponin promoter has a nucleic acid sequence having at least 95% identity to SEQ ID NO: 3. In some embodiments, the 3' element comprises a Woodchuck Hepatitis Virus Posttranscriptional Regulatory Element (WPRE), a bovine growth hormone polyadenylation (bGH polyA) sequence, or a combination thereof. In some embodiments, the gene therapy vector further comprises a cardiac specific enhancer. In some embodiments, the nucleic acid encoding the PKP2 gene has a sequence having at least 95% identity to SEQ ID NO: 1 or SEQ ID NO: 2. In some embodiments, the nucleic acid has a size less than or equal to about 4.7 kb. In some embodiments, the pharmaceutically acceptable carrier or excipient comprises a buffer, a polymer, a salt, or a combination thereof. In some embodiments, the method reverses, reduces, or prevents at least one of fibrofatty tissue replacement; myocardial atrophy; predominant right ventricular dilation; ventricular arrhythmias; sudden cardiac death; exercise-triggered cardiac events; right ventricular cardiomyopathy, dilation, or heart failure; left ventricular cardiomyopathy, dilation, or heart failure; atrial arrhythmias; syncope; palpitations; shortness of breath; or chest pain. In some embodiments, the method restores desmosome structure and/or function. In some embodiments, the method restores PKP2 mRNA expression and/or PKP2 protein and activity levels. In some embodiments, the method restores expression of one or more genes having a direct or indirect effect on one or more symptoms of the heart disease. In some embodiments, the gene comprises one or more of Ryanodine Receptor 2 (Ryr2), Ankyrin-B (Ank2), Cacna1c (CaV1.2), triadin (Trdn), or calsequestrin-2 (Casq2). In some embodiments, the individual is identified as having at least one variation in a desmosome protein. In some embodiments, the desmosome protein is PKP2. In some embodiments, the variation comprises a deletion, an insertion, a single nucleotide variation, or a copy number variation.

In one aspect, provided herein are methods for treating a heart disease or disorder in an individual in need thereof. In some embodiments, the method comprises administering a composition comprising a gene therapy vector comprising a nucleic acid encoding a plakophilin 2 (PKP2) polypeptide or a fragment thereof operatively linked to at least one promoter and a pharmaceutically acceptable carrier or excipient. In some embodiments, the gene therapy vector comprises a viral vector. In some embodiments, the viral vector is selected from the group consisting of an adeno-associated virus, an adenovirus, a lentivirus, a pox virus, a vaccinia virus, or a herpes virus. In some embodiments, the gene therapy vector is an adeno-associated virus. In some embodiments, the adeno-associated virus is selected from the group consisting of an AAV6, an AAV8, and an AAV9. In some embodiments, the adeno-associated virus is an AAV9 or a derivative thereof. In some embodiments, the AAV9 has a nucleic acid sequence with at least 95% identity to SEQ ID NO: 7. In some embodiments, the heart disease or disorder is arrhythmogenic right ventricular cardiomyopathy (ARVC) or arrhythmogenic cardiomyopathy (ACM). In some embodiments, the composition is administered intravenously, intracardially, pericardially, or intraarterially. In some embodiments, the promoter is a cardiac specific promoter. In some embodiments, the cardiac specific promoter is a troponin promoter, or an alpha-myosin heavy chain promoter. In some embodiments, the troponin promoter has a nucleic acid sequence having at least 95% identity to SEQ ID NO: 3. In some embodiments, the promoter is a PKP2 promoter. In some embodiments, the PKP2 promoter has a nucleic acid sequence having at least 95% identity to SEQ ID NO: 4. In some embodiments, the promoter is a constitutive promoter. In some embodiments, the constitutive promoter is an beta-actin promoter. In some embodiments, the gene therapy vector further comprises a cardiac specific enhancer. In some embodiments, the nucleic acid encoding the PKP2 gene has a sequence having at least 95% identity to SEQ ID NO: 1 or SEQ ID NO: 2. In some embodiments, the pharmaceutically acceptable carrier or excipient comprises a buffer, a polymer, a salt, or a combination thereof. In some embodiments, the method reverses, reduces, or prevents at least one of fibrofatty tissue replacement, myocardial atrophy, predominant right ventricular dilation, ventricular arrhythmias, sudden cardiac death, or exercise-triggered cardiac events; right ventricular cardiomyopathy, dilation, or heart failure; left ventric. In some embodiments, the method restores desmosome structure and/or function. In some embodiments, the method restores PKP2 mRNA expression and/or PKP2 protein and activity levels. In some embodiments, the method restores PKP2 induced gene expression. In some embodiments, the method restores expression of one or more genes having a direct or indirect effect on one or more symptoms of the heart disease. In some embodiments, the method restores expression of one or more of Ryanodine Receptor 2 (Ryr2), Ankyrin-B (Ank2), Cacna1c (CaV1.2), triadin (Trdn), or calsequestrin-2 (Casq2). In some embodiments, the individual is identified as having at least one variation in a desmosome protein. In some embodiments, the desmosome protein is PKP2. In some embodiments, the variation comprises a deletion, an insertion, a single nucleotide variation, or a copy number variation.

In another aspect, there are provided gene therapy vectors comprising a plakophilin 2 gene operatively linked to at least one promoter. In some embodiments, the gene therapy vector comprises a viral vector. In some embodiments, the viral vector is selected from the group consisting of an adeno-associated virus, an adenovirus, a lentivirus, a pox virus, a vaccinia virus, or a herpes virus. In some embodiments, the gene therapy vector is an adeno-associated virus. In some embodiments, the adeno-associated virus is selected from the group consisting of an AAV6, an AAV8, and an AAV9. In some embodiments, the adeno-associated virus is an AAV9 or a derivative thereof. In some embodiments, the AAV9 has a nucleic acid sequence with at least 95% identity SEQ ID NO: 7. In some embodiments, the promoter is a cardiac specific promoter. In some embodiments, the cardiac specific promoter is a troponin promoter or an alpha-myosin heavy chain promoter. In some embodiments, the troponin promoter has a nucleic acid sequence having at least 95% identity to SEQ ID NO: 3. In some embodiments, the promoter is a PKP2 promoter. In some embodiments, the PKP2 promoter has a nucleic acid sequence having at least 95% identity to SEQ ID NO: 4. In some embodiments, the promoter is a constitutive promoter. In some embodiments, the constitutive promoter is an beta-actin promoter. In some embodiments, the gene therapy vector further comprises a cardiac specific enhancer. In some embodiments, the nucleic acid encoding the PKP2 gene has a sequence having at least 95% identity to SEQ ID NO: 1 or SEQ ID NO: 2. In some embodiments, the gene therapy vector is formulated in a pharmaceutically acceptable carrier or excipient comprising a buffer, a polymer, a salt, or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

An understanding of the features and advantages of the present disclosure will be obtained by reference to the following detailed description that sets forth illustrative embodiments, in which the principles of the disclosure are utilized, and the accompanying drawings of which:

FIG. 3A shows the disappearance of DSP from the cellular membrane. FIG. 3B shows a graph illustrating the reduction in sarcomere density. FIG. 3C shows the disarray of cell compaction in patterned iPSCM.

FIG. 6A shows a vector map of the AAV construct. FIG. 6B shows an immunofluorescence image of restoration of DSP membrane localization.

FIG. 7A shows the experimental timeline. FIG. 7B shows two contractility assays which demonstrate functional rescue of reduced velocity post PKP2 silencing.

FIG. 9A shows expression in soluble and insoluble fractions in cells transduced in different multiplicities of infection. FIG. 9B shows rescue of contraction velocity in cells post PKP2 silencing.

FIG. 11A shows body weight before and after AAV9 injection. FIG. 11B shows ejection fraction in mice treated with the AAV9 human or mouse PKP2a. FIG. 11C and FIG. 11D show LV structure measured by internal diameters end diastole and systole. FIG. 11E, FIG. 11F, and FIG. 11G show electrophysiology activity by QRS (11E), QT interval (11F) and P/R amplitude (11G).

FIG. 13A (left panel) shows images that illustrate increased RV internal dimension at end-diastole (RVIDd) in PKP2-cKO mice. FIG. 13A (right panel) shows a graph of RVIDd over time in PKP2-cKO mice. FIG. 13B (left panel) shows images illustrating the increase in RV area in PKP2- cKO mice. FIG. 13B (right panel) shows a graph of RV area over time in PKP2-cKO mice.

FIG. 14A (left panel) shows images of increased LV internal dimension at end-systole (LVIDs) and end-diastole (LVIDd) in PKP2-cKO mice. FIG. 14A (right panel) shows a graph which shows the increase in LVIDs and LVIDd in PKP2-cKO mice over time. FIG. 14B shows a graph of LV performance as measured by percent ejection fraction over time.

FIG. 16A shows PKP2 RNA expression in RV and LV (top) and desmosome and Cx43 protein expression (bottom) of PKP2-cKO mice compared with control. FIG. 16B shows enhanced expression of fibrosis genes: TGFβ1, Col1a1, and Col3a1; and tissue remodeling genes: Timp1 and Mmp2 in PKP2-cKO mice compared with control. FIG. 16C shows enhanced expression of heart failure markers, NPPA and NPPB, in PKP2-cKO mice compared with control mice.

FIG. 18A shows a schematic of the AAV expression cassettes for human and mouse PKP2a.

FIG. 20A shows a graph illustrating improvement in ejection fraction in AAV9:PKP2 treated mice. FIG. 20B shows a graph illustrating reduction of RV dilation in AAV9:PKP2 treated mice. FIG. 20C shows graphs illustrating improvement in LVIDd (top) and LVIDs (bottom).

FIG. 21A shows exemplary raw ECG traces of control and PKP2-cKO mice treated with AAV9:mPKP2 and buffer. FIG. 21B shows graphs illustrating improvement of P/R ratio, QT interval, and QRS interval in PKP2-cKO mice treated with AAV9:PKP2 compared with treatment with buffer.

FIG. 22A (top) shows a table grading of severity of arrhythmias. FIG. 22A (bottom) shows a graph which summarizes improvement of arrhythmia scores of PKP2-cKO mice treated with AAV9:PKP2 compared with control. FIG. 22B shows a distribution graph showing improvement in severity of arrhythmias in PKP2-cKO mice treated with AAV9:PKP2 compared with control. Each dot represents an animal.

DETAILED DESCRIPTION

Figures 1, 2:
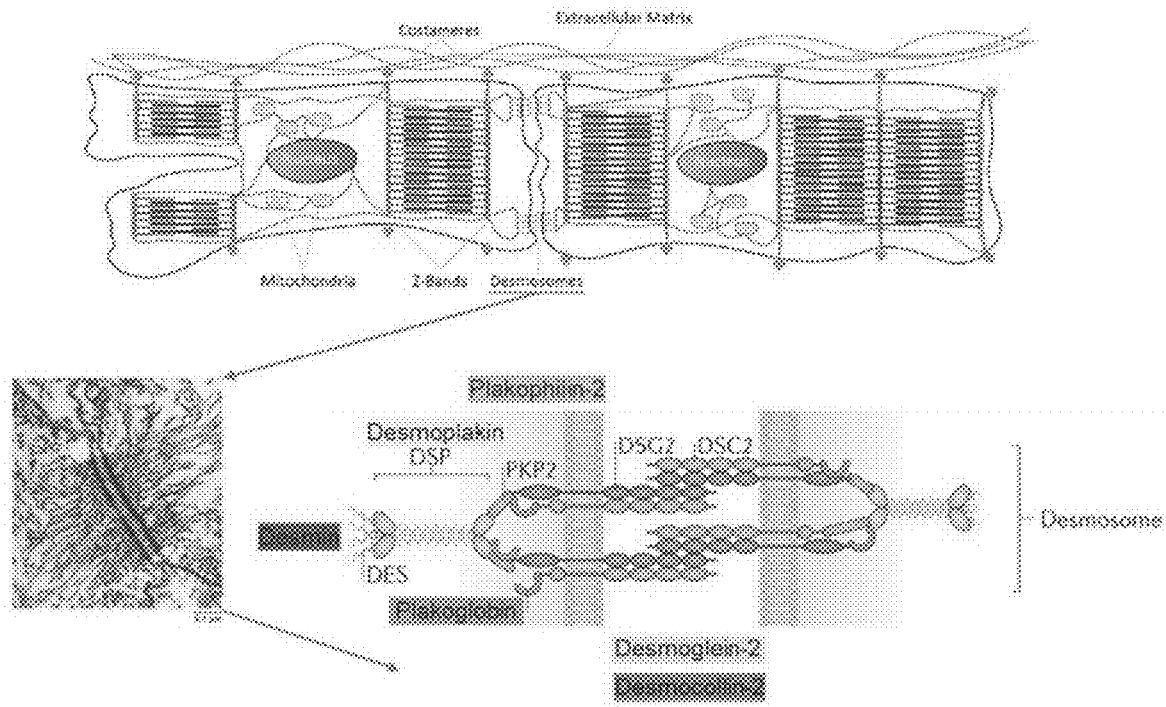
FIG. 1 illustrates how cardiac desmosomes tie cells together.
FIG. 2 shows a summary of ARVC disease indications and possible disease mechanisms.

The most common genetic basis of ARVC is mutations in genes encoding desmosomal proteins. Functionally, desmosomes are adhesive intercellular connections that hold intercalated cardiomyocytes together. Plakophillin-2 (PKP2), one of desmosomal genes, is most frequently identified as the causal factor for ARVC. Internal to the membrane-located complex, PKP2 interacts with desmosomal proteins, plakoglobin (PKG) and desmoplakin (DSP). DSP anchors the intermediate filaments, desmin, which form an interwoven network to stabilize the contractile units of cardiac cells, sarcomeres, and other organelles (FIG. 1, Brodehl et al., 2018; Moncayo-Arlandi and Brugada, 2017). It is believed that the loss of desmosome impacts cell-cell adhesion, signal transduction, and electrical coupling of cardiomyocytes (Wang et al., 2018). Furthermore, the lost signal transduction and electrical coupling are joint defective outcomes by additional collapse of connexin-containing Gap junctions (GJs). GJs are essential in electrically coupling cells and facilitate synchronous beating by allowing flow of small molecules between cells (Green et al., 2019)(FIG. 2 summary on ARVC disease indication and possible mechanisms).

To delineate the functionality of desmosomes, genetic mouse lines and patient-derived iPSCM models were generated. Cardiac knock-out mouse model of PKP2 (the Delmar mouse model, Cerrone et al., 2017) showed profound early development of biventricular dilation, fibrosis, and a significant reduction of genes regulating $Ca^{2+}$ homeostasis, revealing underling mechanisms for arrhythmias possibly before overt structural changes. Several patient-derived iPSCM lines harboring PKP2 mutations showed reduction of PKP2 expression, $Ca^{2+}$ handling defects, and lipid droplet accumulation induced by culturing in lipogenic induction media (Brodehl et al., 2019).

Reduction of PKP2 at both mRNA and protein level was reported in ARVC patient heart samples with PKP2 mutations (Akdis et al., 2016; Asimaki et al., 2009). Nonsense-mediated mRNA-decay (NMD) was proposed for some desmosomal gene mutations including PKP2 mutations, suggesting a much less known cellular mechanism in balancing expression of mutated transcripts and proteins (Gerull and Brodehl, 2020; Mura et al., 2003). Those observations suggest a possibility of gene therapy-based intervention of ARVC by restoring expression level of WT PKP2 in heart.

Methods of Treatment

PKP2 gene therapy vectors provided herein in various aspects are useful for treating an individual with a heart disease or condition. "Treating" or "treatment of a condition or subject in need thereof" refers to (1) taking steps to obtain beneficial or desired results, including clinical results such as the reduction of symptoms; (2) preventing the disease, for example, causing the clinical symptoms of the disease not to develop in a patient that is predisposed to the disease, for example a carrier of a genetic mutation in a desmosome gene such as PKP2, but does not yet experience or display symptoms of the disease; (3) inhibiting the disease, for example, arresting or reducing the development of the disease or its clinical symptoms; (4) relieving the disease, for example, causing regression of the disease or its clinical symptoms; or (5) delaying the disease. In one aspect, provided herein are methods for treating a heart disease or disorder in an individual in need thereof. In some cases, the method comprises administering a composition comprising a gene therapy vector comprising a nucleic acid encoding a plakophilin 2 (PKP2) polypeptide or a fragment thereof operatively linked to at least one promoter and a pharmaceutically acceptable carrier or excipient. In some cases, the heart disease or disorder is arrhythmogenic right ventricular cardiomyopathy (ARVC) or arrhythmogenic cardiomyopathy (ACM). In some cases, methods of treatment herein reduce at least one symptom of a arrhythmogenic cardiomyopathy, including but not limited to the method reverses, reduces, or prevents at least one of fibrofatty tissue replacement, myocardial atrophy, predominant right ventricular dilation, ventricular arrhythmias, sudden cardiac death, or exercise-triggered cardiac events; right ventricular cardiomyopathy, dilation, or heart failure; left ventric. In some cases, the method restores desmosome structure and/or function. In some cases, the method restores PKP2 mRNA expression and/or PKP2 protein and activity levels. In some cases, the method restores PKP2 induced gene expression. In some cases, PKP2 induced gene expression comprises expression of genes whose expression are direct or indirect causal factors leading to one or more disease phenotypes. In some embodiments, the method restores expression of one or more genes having a direct or indirect effect on one or more symptoms of the heart disease. In some cases, the method restores expression of one or more of Ryanodine Receptor 2 (Ryr2), Ankyrin-B (Ank2), Cacna1c (CaV1.2), triadin (Trdn), or calsequestrin-2 (Casq2).

In some embodiments of methods of treatment provided herein, the gene therapy vector comprises a viral vector. Any suitable viral vector is contemplated for use in methods herein including but not limited to a viral vector selected from the group consisting of an adeno-associated virus, an adenovirus, a lentivirus, a pox virus, a vaccinia virus, or a herpes virus. In some cases, the gene therapy vector is an adeno-associated virus. In some cases, the adeno-associated virus is selected from the group consisting of an AAV6, an AAV8, and an AAV9, or a derivative thereof. In some cases, the adeno-associated virus is an AAV9 or a derivative thereof. In some cases, the AAV9 has a nucleic acid sequence with at least 80%, 85%, 90%, 95%, or 99% identity to SEQ ID NO: 7. In some cases, the adeno-associated virus is modified to improve transduction of affected cells, such as cardiomyocytes, for example, in some cases, the adeno-associated virus is a derivative of an AAV6, an AAV8, or an AAV9. In some cases, the derivative is any AAV described in U.S. Patent Application No. 63/012,703, which is hereby incorporated by reference in its entirety.

In some embodiments or methods of treatment provided herein, the composition comprising a gene therapy vector is administered through any suitable route to reach the affected cells. For example, in some cases, the composition is administered intravenously, intracardially, pericardially, or intraarterially.

In some embodiments of methods of treatment provided herein, PKP2 is expressed by any promoter suitable for expression in the affected cells and tissues, for example cardiomyocytes. For example in some cases, the promoter is a cardiac specific promoter. In some cases, the cardiac specific promoter is a troponin promoter or an alpha-myosin heavy chain promoter. In some cases, the promoter is a PKP2 promoter. In some cases, a cardiac specific enhancer is combined with the promoter. In some cases, the troponin promoter has a nucleic acid sequence having at least 80%, 85%, 90%, 95%, or 99% identity to SEQ ID NO: 3. In some cases, the PKP2 promoter has a nucleic acid sequence having at least 80%, 85%, 90%, 95%, or 991 identity to SEQ ID NO: 4. In some cases, the promoter is a constitutive promoter. In some cases, the constitutive promoter is an beta-actin promoter.

In some embodiments of methods of treatment provided herein the nucleic acid encoding the PKP2 gene has any suitable sequence encoding a PKP2 polypeptide for example, any nucleic acid encoding a polypeptide having a sequence of SEQ ID NO: 8. For example, in some cases, the PKP2 gene has a sequence having at least 80%, 85%, 90%, 95%, or 99% identity to SEQ ID NO: 1. In some cases, the PKP2 gene has a sequence having at least 80%, 85%, 90%, 95%, or 99% identity to SEQ ID NO: 2. In some cases, the nucleic acid sequence encoding the PKP2 gene is codon optimized.

In some embodiments of methods of treatment provided herein, the gene therapy vector has a gene expression cassette having a size of about 3 kb to about 5 kb. In some embodiments, the gene expression cassette has a size of about 4 kb to about 5 kb. In some embodiments, the gene expression cassette has a size of about 4.2 kb to about 4.8 kb. In some embodiments, the gene expression cassette has a size of about 4.5 kb. In some embodiments, the gene expression cassette has a size no larger than about 5 kb. In some embodiments, the gene expression cassette has a size no larger than about 4.9 kb. In some embodiments, the gene expression cassette has a size no larger than about 4.8 kb. In some embodiments, the gene expression cassette has a size no larger than about 4.7 kb. In some embodiments, the gene expression cassette has a size no larger than about 4.6 kb. In some embodiments, the gene expression cassette has a size no larger than about 4.5 kb. In some embodiments, the gene expression cassette has a size no larger than about 4.4 kb. In some embodiments, the gene expression cassette has a size no larger than about 4.3 kb. In some embodiments, the gene expression cassette has a size no larger than about 4.2 kb. In some embodiments, the gene expression cassette has a size no larger than about 4.1 kb. In some embodiments, the gene expression cassette has a size no larger than about 4 kb. In some embodiments, the gene expression cassette has a size no larger than about 3.9 kb. In some embodiments, the gene expression cassette has a size no larger than about 3.8 kb. In some embodiments, the gene expression cassette has a size no larger than about 3.7 kb. In some embodiments, the gene expression cassette has a size no larger than about 3.6 kb. In some embodiments, the gene expression cassette has a size no larger than about 3.5 kb. In some embodiments, the gene expression cassette has a size of at least about 3.1 kb. In some embodiments, the gene expression cassette has a size of at least about 3.3 kb. In some embodiments, the gene expression cassette has a size of at least about 3.5 kb. In some embodiments, the gene expression cassette has a size of at least about 3.7 kb. In some embodiments, the gene expression cassette has a size of at least about 3.9 kb. In some embodiments, the gene expression cassette has a size of at least about 4.1 kb. In some embodiments, the gene expression cassette has a size of at least about 4.2 kb. In some embodiments, the gene expression cassette has a size of at least about 4.3 kb. In some embodiments, the gene expression cassette has a size of at least about 4.4 kb. In some embodiments, the gene expression cassette has a size of at least about 4.5 kb. In some embodiments, the gene expression cassette has a size of at least about 4.6 kb. In some embodiments, the gene expression cassette has a size of at least about 4.7 kb. In some embodiments, the gene expression cassette has a size of at least about 4.8 kb. In some embodiments, the gene expression cassette has a size of at least about 4.9 kb. In some embodiments, the gene expression cassette has a size of at least about 5 kb.

In various embodiments of methods herein, the gene therapy vector comprising a PKP2 gene is formulated in a composition comprising a pharmaceutically acceptable carrier or excipient. For example, in some cases, the pharmaceutically acceptable carrier or excipient comprises a buffer, a polymer, a salt, or a combination thereof.

In some embodiments of methods of treatment provided herein, the individual is identified as having at least one variation in a desmosome protein. In some cases, the desmosome protein is PKP2. In some cases, the variation comprises a deletion, an insertion, a single nucleotide variation, or a copy number variation. In some cases, the individual is identified as having at least one variation in a desmosome protein via DNA sequencing, PCR, qPCR, in situ hybridization, or another other suitable method of identifying a gene variation in an individual.

Gene Therapy Vectors

In another aspect, there are provided gene therapy vectors comprising a plakophilin 2 gene operatively linked to at least one promoter. In some cases, the gene therapy vector comprises a viral vector. In some cases, the viral vector is any suitable viral vector for treating a heart disease or condition. In some cases, the viral vector is selected from the group consisting of an adeno-associated virus, an adenovirus, a lentivirus, a pox virus, a vaccinia virus, or a herpes virus. In some cases, the gene therapy vector is an adeno-associated virus. In some cases, the adeno-associated virus is selected from the group consisting of an AAV6, an AAV8, and an AAV9, or a derivative thereof. In some cases, the adeno-associated virus is an AAV9 or a derivative thereof. In some cases, the AAV9 has a nucleic acid sequence with at least 95% identity SEQ ID NO: 7. In some cases, the adeno-associated virus is a derivative of AAV6, AAV8, or AAV9, optimized for transducing cells according to methods of treatment herein. In some cases, the derivative is any AAV described in U.S. Patent Application No. 63/012,703, which is hereby incorporated by reference in its entirety.

In some embodiments of gene therapy vectors provided herein, PKP2 is expressed by any promoter suitable for expression in the affected cells and tissues, for example cardiomyocytes. For example in some cases, the promoter is a cardiac specific promoter. In some cases, the cardiac specific promoter is a troponin promoter or an alpha-myosin heavy chain promoter. In some cases, the promoter is a PKP2 promoter. In some cases, a cardiac specific enhancer is combined with the promoter. In some cases, the troponin promoter has a nucleic acid sequence having at least 80%, 85%, 90%, 95%, or 99% identity to SEQ ID NO: 3. In some cases, the PKP2 promoter has a nucleic acid sequence having at least 80%, 85%, 90%, 95%, or 99% identity to SEQ ID NO: 4. In some cases, the promoter is a constitutive promoter. In some cases, the constitutive promoter is an beta-actin promoter.

In some embodiments of gene therapy vectors provided herein the nucleic acid encoding the PKP2 gene has any suitable sequence encoding a PKP2 polypeptide for example, any nucleic acid encoding a polypeptide having a sequence of SEQ ID NO: 8. For example, in some cases, the PKP2 gene has a sequence having at least 80%, 85%, 90%, 95%, or 99% identity to SEQ ID NO: 1. In some cases, the PKP2 gene has a sequence having at least 80%, 85%, 90%, 95%, or 99% identity to SEQ ID NO: 2. In some cases, the nucleic acid sequence encoding the PKP2 gene is codon optimized.

In some embodiments of gene therapy vectors provided herein, the gene therapy vector comprises a 3' element. In some embodiments, the 3' element stabilizes the transcriptional product of the gene therapy vector (e.g., the PKP2 transcript). In some embodiments, the 3' element comprises a bovine growth hormone (BGH) polyadenylation sequence. In some embodiments, the 3' element comprises a woodchuck hepatitis virus posttranscriptional regulatory element (WPRE).

In some embodiments of gene therapy vectors provided herein, the gene therapy vector has a gene expression cassette having a size of about 3 kb to about 5 kb. In some embodiments, the gene expression cassette has a size of about 4 kb to about 5 kb. In some embodiments, the gene expression cassette has a size of about 4.2 kb to about 4.8 kb. In some embodiments, the gene expression cassette has a size of about 4.5 kb. In some embodiments, the gene expression cassette has a size no larger than about 5 kb. In some embodiments, the gene expression cassette has a size no larger than about 4.9 kb. In some embodiments, the gene expression cassette has a size no larger than about 4.8 kb. In some embodiments, the gene expression cassette has a size no larger than about 4.7 kb. In some embodiments, the gene expression cassette has a size no larger than about 4.6 kb. In some embodiments, the gene expression cassette has a size no larger than about 4.5 kb. In some embodiments, the gene expression cassette has a size no larger than about 4.4 kb. In some embodiments, the gene expression cassette has a size no larger than about 4.3 kb. In some embodiments, the gene expression cassette has a size no larger than about 4.2 kb. In some embodiments, the gene expression cassette has a size no larger than about 4.1 kb. In some embodiments, the gene expression cassette has a size no larger than about 4 kb. In some embodiments, the gene expression cassette has a size no larger than about 3.9 kb. In some embodiments, the gene expression cassette has a size no larger than about 3.8 kb. In some embodiments, the gene expression cassette has a size no larger than about 3.7 kb. In some embodiments, the gene expression cassette has a size no larger than about 3.6 kb. In some embodiments, the gene expression cassette has a size no larger than about 3.5 kb. In some embodiments, the gene expression cassette has a size of at least about 3.1 kb. In some embodiments, the gene expression cassette has a size of at least about 3.3 kb. In some embodiments, the gene expression cassette has a size of at least about 3.5 kb. In some embodiments, the gene expression cassette has a size of at least about 3.7 kb. In some embodiments, the gene expression cassette has a size of at least about 3.9 kb. In some embodiments, the gene expression cassette has a size of at least about 4.1 kb. In some embodiments, the gene expression cassette has a size of at least about 4.2 kb. In some embodiments, the gene expression cassette has a size of at least about 4.3 kb. In some embodiments, the gene expression cassette has a size of at least about 4.4 kb. In some embodiments, the gene expression cassette has a size of at least about 4.5 kb. In some embodiments, the gene expression cassette has a size of at least about 4.6 kb. In some embodiments, the gene expression cassette has a size of at least about 4.7 kb. In some embodiments, the gene expression cassette has a size of at least about 4.8 kb. In some embodiments, the gene expression cassette has a size of at least about 4.9 kb. In some embodiments, the gene expression cassette has a size of at least about 5 kb.

In various embodiments of gene therapy vectors provided herein, the gene therapy vector comprising a PKP2 gene is formulated in a composition comprising a pharmaceutically acceptable carrier or excipient. For example, in some cases, the pharmaceutically acceptable carrier or excipient comprises a buffer, a polymer, a salt, or a combination thereof.

In some embodiments, gene therapy vectors herein comprise nucleic acid sequences provided in Table 1 below.

TABLE 1

Sequences

| Name | Sequence | SEQ ID NO: |
|---|---|---|
| Human PKP2 | ATGGCAGCCCCCGGCGCCCCAGCTGAGTACGGCTACATCCGGAC<br>GTCCTGGGCCAGCAGATCCTGGGACAACTGGACAGCTCCAGCCT<br>GGCGCTGCCCTCCGAGGCCAAGCTGAAGCTGGCGGGGAGCAGCG<br>GCCGCGGCGGCCAGACAGTCAAGAGCCTGCGGATCCAGGAGCAG<br>GTGCAGCAGACCCTCGCCCGGAAGGGCCGCAGCTCCGTGGGCAA<br>CGGAAATCTTCACCGAACCAGCAGTGTTCCTGAGTATGTCTACA<br>ACCTACACTTGGTTGAAAATGATTTTGTTGGAGGCCGTTCCCCT<br>GTTCCTAAAACCTATGACATGCTAAAGGCTGGCACAACTGCCAC<br>TTATGAAGGTCGCTGGGGAAGAGGAACAGCACAGTACAGCTCCC<br>AGAAGTCCGTGGAAGAAAGGTCCTTGAGGCATCCTCTGAGGAGA<br>CTGGAGATTTCTCCTGACAGCAGCCCGGAGAGGGCTCACTACAC<br>GCACAGCGATTACCAGTACAGCCAGAGAAGCCAGGCTGGGCACA<br>CCCTGCACCACCAAGAAAGCAGGCGGGCCGCCCTCCTAGTGCCA<br>CCGAGATATGCTCGTTCCGAGATCGTGGGGGTCAGCCGTGCTGG<br>CACCACAAGCAGGCAGCGCCACTTTGACACATACCACAGACAGT<br>ACCAGCATGGCTCTGTTAGCGACACCGTTTTTGACAGCATCCCT<br>GCCAACCCGGCCCTGCTCACGTACCCCAGGCCAGGGACCAGCCG<br>CAGCATGGGCAACCTCTTGGAGAAGGAGAACTACCTGACGGCAG<br>GGCTCACTGTCGGGCAGGTCAGGCCGCTGGTGCCCCTGCAGCCC<br>GTCACTCAGAACAGGGCTTCCAGGTCCTCCTGGCATCAGAGCTC<br>CTTCCACAGCACCCGCACGCTGAGGGAAGCTGGGCCCAGTGTCG<br>CCGTGGATTCCAGCGGGAGGAGAGCGCACTTGACTGTCGGCCAG<br>GCGGCCGCAGGGGGAAGTGGGAATCTGCTCACTGAGAAGCAC<br>TTTCACTGACTCCCAGCTGGGGAATGCAGACATGGAGATGACTC<br>TGGAGCGAGCAGTGAGTATGCTCGAGGCAGACCACATGCTGCCA<br>TCCAGGATTTCTGCTGCAGCTACTTTCATACAGCACGAGTGCTT<br>CCAGAAATCTGAAGCTCGGAAGAGGGTTAACCAGCTTCGTGGCA<br>TCCTCAAGCTTCTGCAGCTCCTAAAAGTTCAGAATGAAGACGTT<br>CAGCGAGCTGTGTGTGGGGCCTTGAGAAACTTAGTATTTGAAGA<br>CAATGACAACAAATTGGAGGTGGCTGAACTAAATGGGGTACCTC<br>GGCTGCTCCAGGTGCTGAAGCAAACCAGAGACTTGGAGACTAAA<br>AAACAAATAACAGGTTTGCTGTGGAATTTGTCATCTAATGACAA<br>ACTCAAGAATCTCATGATAACAGAAGCATTGCTTACGCTGACGG<br>AGAATATCATCATCCCCTTTTCTGGGTGGCCTGAAGGAGACTAC<br>CCAAAAGCAAATGGTTTGCTCGATTTTGACATATTCTACAACGT<br>CACTGGATGCCTAAGAAACATGAGTTCTGCTGGCGCTGATGGGA<br>GAAAAGCGATGAGAAGATGTGACGGACTCATTGACTCACTGGTC<br>CATTATGTCAGAGGAACCATTGCAGATTACCAGCCAGATGACAA<br>GGCCACGGAGAATTGTGTGTGCATTCTTCATAACCTCTCCTACC<br>AGCTGGAGGCAGAGCTCCCAGAGAAATATTCCCAGAATATCTAT<br>ATTCAAAACCGGAATATCCAGACTGACAACAACAAAAGTATTGG<br>ATGTTTTGGCAGTCGAAGCAGGAAAGTAAAAGAGCAATACCAGG<br>ACGTGCCGATGCCGGAGGAAAAGAGCAACCCCAAGGGCGTGGAG<br>TGGCTGTGGCATTCCATTGTTATAAGGATGTATCTGTCCTTGAT<br>CGCCAAAAGTGTCCGCAACTACACACAAGAAGCATCCTTAGGAG<br>CTCTGCAGAACCTCACGGCCGGAAGTGGACCAATGCCGACATCA<br>GTGGCTCAGACAGTTGTCCAGAAGGAAAGTGGCCTGCAGCACAC<br>CCGAAAGATGCTGCATGTTGGTGACCCAAGTGTGAAAAAGACAG<br>CCATCTCGCTGCTGAGGAATCTGTCCCGGAATCTTTCTCTGCAG<br>AATGAAATTGCCAAAGAAACTCTCCCTGATTTGGTTTCCATCAT<br>TCCTGACACAGTCCCGAGTACTGACCTTCTCATTGAAACTACAG<br>CCTCTGCCTGTTACACATTGAACAACATAATCCAAAACAGTTAC<br>CAGAATGCACGCGACCTTCTAAACACCGGGGCATCCAGAAAAT<br>TATGGCCATTAGrGcAGGCGATGCCTATGCCTCCAACAAAGCAA<br>GTAAAGCTGCTTCCGTCCTTCTGTATTCTCTGTGGGCACACACG<br>GAACTGCATCATGCCTACAAGAAGGCTCAGTTTAAGAAGACAGA<br>TTTTGTCAACAGCCGGACTGCCAAAGCCTACCACTCCCTTAAAG<br>ACTGA | 1 |
| Human PKP2 (codon optimized) | ATGGCTGCTCCTGGTGCTCCTGCCGAGTACGGCTACATCAGAAC<br>AGTGCTGGGCCAGCAGATCCTGGGACAGCTGGATTCTAGCTCTC<br>TGGCCCTGCCTTCTGAGGCCAAGCTGAAACTGGCCGGCAGTTCT<br>GGAAGAGGCGGCCAGACAGTGAAGTCCCTGCGGATCCAAGAACA<br>GGTGCAGCAGACCCTGGCCAGAAAGGGCAGATCTTCTGTCGGCA<br>ACGGCAACCTGCACAGAACCAGCTCTGTGCCCGAGTACGTGTAC<br>AATCTGCACCTGGTGGAAAACGACTTCGTCGGCGGCAGATCCCC<br>TGTGCCTAAGACCTACGATATGCTGAAGGCCGGCACCACCGCCA<br>CCTATGAAGGCAGATGGGGAAGAGGCACAGCCCAGTACAGCAGC<br>CAGAAAAGCGTGGAAGAGAGAAGCCTGCGGCACCCTCTGCGGAG<br>ACTGGAAATCAGCCTGATAGCAGCCCAGAGAGAGCCCACTACA<br>CCCACAGCGACTACCAGTACTCCCAGAGATCTCAGGCCGGCCAC<br>ACACTGCACCACCAAGAGTCTAGAAGGGCCGCTCTGCTGGTGCC<br>TCCTAGATACGCCAGATCTGAGATCGTGGGCGTGTCCAGAGCCG<br>GCACAACAAGCAGACAGAGACACTTCGACACCTACCACCGGCAG<br>TATCAGCACGGCAGCGTGTCCGATACCGTGTTCGATAGCATCCC | 2 |

TABLE 1-continued

Sequences

| Name | Sequence | SEQ ID NO: |
|---|---|---|
|  | CGCCAATCCTGCTCTGCTGACATACCCTAGACCTGGCACCTCCA GATCCATGGGCAATCTGCTGGAAAAAGAGAACTACCTGACCGCC GGACTGACCGTGGGACAAGTTCGACCTCTGGTTCCTCTGCAGCC CGTGACACAGAACAGAGCCAGCAGAAGCAGCTGGCACCAGTCCA GCTTCCACAGCACCAGAACACTGAGAGAAGCTGGCCCTAGCGTG GCCGTGGATTCTTCTGGTAGAAGGGCTCACCTGACAGTTGGCCA AGCAGCTGCAGGCGGAAGCGGAAATCTGCTGACCGAGAGAAGCA CCTTCACCGACAGCCAGCTGGGCAACGCCGACATGGAAATGACA CTGGAACGGGCCGTGICCATGCTGGAAGCCGATCACATGGTGCC CAGCAGAATTAGCGCCGCTGCCACCTTTATCCAGCACGAGTGCT TCCAGAAGTCTGAGGCCCGGAAGAGAGTGAACCAGCTGAGAGGC ATCCTGAAGCTGCTGCAGCTCCTGAAGGTGCAGAACGAGGATGT GCAGAGGGCTGTGTGTGGGGCCCTGAGAAATCTGGTGTTCGAGG ACAACGACAACAAGCTGGAAGTGGCCGAGCTGAACGGCGTGCCA AGACTGCTGCAGGTTCTGAAACAGACCCGCGACCTGGAAACAAA GAAGCAGATCACCGGCCTGCTCTGGAACCTGAGCAGCAACGACA AGCTGAAGAACCTGATGATCACAGAGGCCCTGCTGACCCTGACA GAGAACATCATCATCCCTTTCAGCGGCTGGCCCGAGGGCGATTA CCCTAAAGCTAATGGCCTGCTGGACTTCGACATCTTCTACAACG TGACCGGCTGCCTGAGAAACATGTCTAGCGCTGGCGCCGATGGC AGAAAGGCCATGAGAAGATGTGACGGCCTGATCGACAGCCTGGT GCACTATGTGCGGGGCACAATCGCCGATTACCAGCCTGATGATA AGGCCACCGAGAACTGCGTGTGCATCCTGCACAACCTGAGCTAC CAGCTGGAAGCAGAGCTGCCCGAGAAGTACAGCCAGAACATCTA CATCCAGAACMGAACATCCAGACCGACAACAACAAGAGCATCGG CTGCTTCGGCAGCCGCAGCCGGAAAGTGAAAGAACAGTACCAGG ACGTGCCCATGCCTGAGGAAAAGTCTAACCCCAAAGGCGTGGAA TGGCTGTGGCACAGCATCGTGATCCGGATGTACCTGAGCCTGAT CGCCAAGAGCGTGCGGAATTACACCCAAGAGGCATCTCTGGGCG CCCTGCAGAATCTGACAGCAGGATCTGGCCCTATGCCTACCTCT GTGGCTCAGACCGTGGTGCAGAAAGAGTCTGGCCTGCAGCACAC CCGGAAGATGCTGCATGTGGGAGATCCCAGCGTGAAGAAAACCG CCATCAGCCTGCTGAGAAACCTGAGCCGGAATCTGTCTCTGCAG AATGAGATCGCCAAAGAGACACTGCCCGACCTGGTGTCTATCAT CCCTGACACCGTGCCTAGCACCGACCTGCTGATTGAGACAACAG CCAGCGCCTGCTACACCCTGAACAACATCATTCAGAACTCCTAC CAGAACGCCCGCGATCTGCTGAACACAGGCGGCATCCAGAAAAT CATGGCCATCTCTGCCGGCGACGCCTACGCCTCTAACAAGGCCT CTAAAGCCGCCAGCGTGCTGCTGTATTCTCTGTGGGCCCATACC GAGCTGCACCATGCCTATAAGAAGGCCCAGTTCAAAAAGACCGA CTTCGTGAACAGCCGGACCGCCAAGGCCTACCACTCTCTGAAAG AT |  |
| pcTNT Promoter | GTCATGGAGAAGACCCACCTTGCAGATGTCCTCACTGGGGCTGG CAGAGCCGGCAACCTGCCTAAGGCTGCTCAGTCCATTAGGAGCC AGTAGCCTGGAAGATGTCTTTACCCCCAGCATCAGTTCAAGTGG AGCAGCACATAACTCTTGCCCTCTGCCTTCCAAGATTCTGGTGC TGAGACTTATGGAGTGTCTTGGAGGTTGCCTTCTGCCCCCCAAC CCTGCTCCCAGCTGGCCCTCCCAGGCCTGGGTTGCTGGCCTCTG CTTTATCAGGATTCTCAAGAGGGACAGCTGGTTTATGTTGCATG ACTGTTCCCTGCATATCTGCTCTGGTTTTAAATAGCTTATCTGA GCAGCTGGAGGACCACATGGGCTTATATGGCGTGGGGTACATGT TCCTGTAGCCTTGTCCCTGGCACCTGCCAAAATAGCAGCCAACA CCCCCCACCCCCACCGCCATCCCCCTGCCCCACCCGTCCCCTGT CGCACATTCCTCCCTCCGCAGGGCTGGCTCACCAGGCCCCAGCC CACATGCCTGCTTAAAGCCCTCTCCATCCTCTGCCTCACCCAGT CCCCGCGAGACTGAGCAGACGCCTCCA | 3 |
| PKP2 promoter | CATCTCAGCATCATGGTTGGATGTTTCCACCTGGCTACATAAGC AAGCTTTACACAAGGTGTAATTTGCCTAAATAGTGGTCCATTCT ATTGGGGTGGGAGCAATTGCTTCCAGGACTCACATCCATATGGC TCCCACTTAGCCATGTGGCCTGCTGACAAAGGGTGGCGGAACTG TCACTACTCTGTTGTCCACGCTTTCAGTCCTTTGGTTTCCTCTT CACTCCCTGGACGCTCATGTAAAAAGGGAGGCCATATACCTGTG CATTGTGTGTCTAAGCATTCAGTOTGTGTCTAAAGGCAGAAGGG TGTGGGTAGGAAAAACAAAGACGAGGGAAGCTGCGTTCTCCAAAC ACTTCAGAGTTGAGTAAGTGGGGTTTTGCAGCAATTGAGTGATT TGAGGGAAAGTGAACATACAAACCCAAGCAATCAAAGGGAATAT TATCTTAATACCAGGGATACATGTTTTTCTTTCTGCCTCTTAAG TCCAAAGAGGCAAATCAGGACAAGTGGCTTTGGTTGTAAACTTT AAGGTCAAGGATCCTTTCTGTTGAGCTTAGCTCTCAAGTTCTCA GTAGTCAACTGCGGTGAAACATAATTAATAGCACGATAAATACA AGTTGTGGAAGATTCGATTGAAAGTTGGAGGCCCrCTCCGTGGA TCTCTCTACAAAGAGCCTGTAATAAAGAGGACTTAATGAACGTT AGCAGGGCTATTTAAAAAGCATCGTCTATTAAAATTCATTTCTT | 4 |

TABLE 1-continued

Sequences

| Name | Sequence | SEQ ID NO: |
|---|---|---|
| | CTCTAGAGCCTCTTGTTGGAGTTTCTCTGTGTGGGTGTGTTCGT<br>AAGAGAGGAATGGGTTAGCAAGAGTACTGGGTACAATTTGTGTA<br>TCCAAGAGAAAACAGAAGCTCTCAATGAGGAAGAACATATGTTT<br>CTGGGAGTGCATCTGTGCAAAAAGTACATAGTCCTGACGTTGTA<br>CTAAGAAAAAAAACACTGTCTTTAGAAAGTCTTTTATTTCACAC<br>GTTATCTTCTTGGCACATTTCCCTCATATTGCCCTTTCCGCCTG<br>ACCAAATAGCCCTTTCTCACCCTCAGGTCCAGGAAAACCAGGAA<br>ACGTTTCCAACAGTGCGACAAAGCCTGACTAACCAGACATACTA<br>CTCGCTCGGGGATCCCGGAGGCAAGCCTCAGTCCAAGAACAGGA<br>GTGACTCTCGAGGGCTCACCTGCCTGCAGGGCAGCCCTCCCTG<br>CATCGAGCGGAAATCCATCCTGTCCAGCGCGGGGCGTGGGCAGA<br>GCGGGGCGCGGCCCCGGCAGGCGGTATCCGCTGGGACTCCGACA<br>ACGTGCGCGACCCCAGGCGAACCGCGCCCCTCTCCCCACCTCCC<br>CGCGGGCGGGTACAAGTCTCCAGGTGTCCGCGCGCTCAGCGGGT<br>CCGGCCCGCCCCCGCCCCGCCCCGGGCCCGACTGCGCGTGCC<br>CGGCCGGAGCCGCGCCCCTCCTCAGGGAAGGCCGGGCGTCCGG<br>CCCACGAGGCCGAGCTCCCCCCCGGCCCGGGCCTCTCACCGGCG<br>CGGGGGGCGGGCCAGGGGCGGGGCCGGACTCGAGCGGGGCGGGG<br>CTCGCGGCAGCGCCCCCAGCTCCGTGGCGGCTTCGCCCGCGAGT<br>CCAGAGGCAGGCGAGCAGCTCGGTCGCCCCACCGGCCCC | |
| AAV<br>Human<br>PKP2a<br>Expression<br>Cassette<br>(pcTnT<br>promoter,<br>codon<br>optimized) | ctgcgcgctcgctcgctcactgaggccgccgggcaaagcccgg<br>gcgtcgggcgacctttggtcgcccggcctcagtgagcgagcgag<br>cgcgcagagagggagtggccaactccatcactagggggttccttg<br>tagttaatgattaacccgccatgctacttatctacgfagccatg<br>ctctaggaagatcggaattcGCCCTTAAGTCATGGAGAAGACCC<br>ACCTTGCAGATGTCCTCACTGGGGCTGGCAGAGCCGGCAACCTG<br>CCCAAGGCTGCTCAGTCCATTAGGAGCCAGTAGCCTGGAAGATG<br>TCTTTACCCCCAGCATCAGTTCAAGTGGAGCAGCACATAACTCT<br>TGCCCTCTGCCTTCCAAGATTCTGGTGCTGAGACTTATGGAGTG<br>TCTTGGAGGTTGCCTTCTGCCCCCCAACCCTGCTCCCAGCTGGC<br>CCTCCCAGGCCTGGGTTGCTGGCCTCTGCTTTATCAGGATTCTC<br>AAGAGGGACAGCTGGTTTATGTTGCATGACTGTTCCCTGCATAT<br>CTGCTCTGTTTTAAATAGCTTATGTGAGCAGCTGGAGGACCAC<br>ATGGGCTTATATGGCGTGGGGTACATGTTCCTGTAGCCTTGTCC<br>CTGGCACCTGCCAAAATAGCAGCCAACACCCCCACCTCCCTCC<br>GCAGGGCTGGCTCACCAGGCCCCAGCCCACATGCCTGCTTAAAG<br>CCCTCTCCATCCTCTGCCTCACCCAGTCCCCGCTGAGACTGAGG<br>AGACGCCTCCAGCCACCATGGCTGGTCCTGGTGCTCGTGCCGAG<br>TACGGCTACATCAGAACAGTGCTGGGCCAGCAGATCCTGGGACA<br>GCTGGATTCTAGCTCTCTGGCCCTGCCTTCTGAGGCCAAGCTGA<br>AACTGGCCGGCAGTTCTGGAAGAGGCGGCCAGACAGTGAAGTCC<br>CTGCGGATCCAAGAACAGGTGCAGCAGACCCTGGCCAGAAAGGG<br>CAGATCTTCTGTCGGCAACGGCAACCTGCACAGAACCAGCTCTG<br>TGCCCGAGTACGTGTACAATCTGCACCTGGTGGAAAACGACTTC<br>GTCGGCGGCAGATCGCCTGTGCCTAAGACCTACGATATGCTGAA<br>GGCCGGCACCACCGCCACCTATGAAGGCAGATGGGGAAGAGGCA<br>CAGCCCAGTACAGCAGCCAGAAAAGCGTGGAAGAGAGAAGCCTG<br>CGGCCACCCTCTGCGGAGACTGGAAATCAGCCCTGATAGCAGCC<br>AGAGAGAGCCCACTACACCCACAGCGACTACCAGTACTCCCAGA<br>GATCTCAGGCCGGCCACACACTGCACCACCAAGAGTCTAGAAGG<br>GCCGCTCTGCTGGTGCCTCCTAGATACGCCAGATCTGAGATCGT<br>GGGCGTGTCCAGAGCCGGCACAACAAGCAGACAGAGACACTTCG<br>ACACCTACCACCGGCAGTATCAGCACGGCAGCGTGTCCGATACC<br>GTGTTCGATAGCATCCCCGCCAATCCTGCTCTGCTGACATACCC<br>TAGACCTGGCACCTCCAGATCCATGGGCAATCTGCTGGAAAAAG<br>AGAACTACCTGACCGCGGGACTGACCGTGGGACAAGTTCGACCT<br>CTGGTTCCTCTGCAGCCCGTGACACAGAAGAGAGCCAGCAGAG<br>CAGCTGGCACCAGTCCAGCTTCCACAGCACCAGAACACTGAGAG<br>AAGCTGGCCCTAGCGTGGCCGTGGATTCTTCTGGTAGAAGGGCT<br>CACCTGACAGTTGGCCAAGCAGCTGCAGGCGGAAGCGGAAATCT<br>GCTGACCGAGAGAAGCACCTTCACCGACAGCCAGCTGGGCAACG<br>CCGACATGGAAATGACACTGGAACGGGCCGTGTCCATGCTGGAA<br>GCCGATCACATGCTGCCCAGCAGAATTAGCGCCGCTGCCACCTT<br>TATCCAGCACGAGTGCTTCCAGAAGTCTGAGGCCCGGAAGAGAG<br>TGAACCAGCTGAGAGGCATCCTGAAGCTGCTGCAGCTCCTGAAG<br>GTGCAGAACGAGGATGTGCAGAGGGCTGTGTGTGGGGCCCTGAG<br>AAATCTGGTGTTCGAGGACAACGACAACAAGCTGGAAGTGGCCG<br>AGCTGAACGGCGTGCCAAGACTGCTGCAGGTTCTGAAACAGACC<br>CGCCACCTGGAAACAAAGGAAGCAGATCACCGGCCTGCTCTGGAA<br>CCTGAGCAGCAACGACAAGCTGAAGAACCTGATGATCACAGAGG<br>CCCTGCTGACCCTGACAGAGAACATCATCATCCCTTTCAGCGGC<br>TGGCCCGAGGGCGATTACCCTAAAGCTAATGGCCTGCTGGACTT<br>CGACATCTTCTACAACGTGACCGGCTGCCTGAGAAACATGTCTA<br>GCGCTGGCGCCGATGGCAGAAAGGCCATGAGAAGATGTGACGGC | 5 |

TABLE 1-continued

Sequences

| Name | Sequence | SEQ ID NO: |
|---|---|---|
| | CTGATCGACAGCCTGGTGCACTATGTGCGGGGCACAATCGCCGA<br>TTACCAGCCTGATGATAAGGCCACCGAGAACTGCGTGTGCATCC<br>TGCACAACCTGAGCTACCAGCTGGAAGCAGAGCTGCCCGAGAAG<br>TACAGCCAGAACATCTACATCCAGAACCGGAACATCCAGACCGA<br>CAACAACAAGAGCATCGGCTGCTTCGGCAGCCGCAGCCGGAAAG<br>TGAAAGAACAGTACCAGGACGTGCCCATGCCTGAGGAAAGTCT<br>AACCCCAAAGGCGTGGAATGGCTGTGGCACAGCATCGTGATCCG<br>GATGTACCTGAGCCTGATCGCCAAGAGCGTGCGGAATTACACCC<br>AAGAGGCATCTCTGGGCGCCCTGCAGAATCTGACAGCAGGATCT<br>GGCCCTATGCCTACCTCTGTGGCTCAGACCGTGGTGCAGAAAGA<br>GTCTGGCCTGCAGCACACCCGGAAGATGCTGCATGTGGGAGATC<br>CCAGCGTGAAGAAAACCGCCATCAGCCTGCTGAGAAACCTGAGC<br>CGGAATCTGTCTCTGCAGAATGAGATCGCCAAAGAGACACTGCC<br>CGACCTGGTGTCTATCATCCCTGACACCGTGCCTAGCACCGACC<br>TGCTGATTGAGACAACAGCCAGCGCCTGCTACACCCTGAACAAC<br>ATCATTCAGAACTCCTACCAGAACGCCCGCGATCTGCTGAACAC<br>AGGCGGCATCCAGAAAATCATGGCCATCTCTGCCGGCGACGCCT<br>ACGCCTCTAACAAGGCCTCTAAAGCCGCCAGCGTGCTGCTGTAT<br>TCTCTGTGGGCCCATACCGAGCTGCACCATGCCTATAAGAAGGC<br>CCAGTTCAAAAAGACCGACTTCGTGAACAGCCGGACCGCCAAGG<br>CCTACCACTCTCTGAAAGATGTCGACGGATCCGGTACCGATTAC<br>AAGGACGACGATGACAAGGGCAGCGGCGCCACAAACTTCTCTCT<br>GCTAAAGCAAGCAGGTGATGTTGAAGAAAACCCCGGGCCTGGCT<br>CCGGCGAGGGCAGGGGAAGTCTTCTAACATGCGGGGACGTGGAG<br>GAAAATCCCGGCCCAATGGTGAGCAAGGGCGAGGAGCTGTTCAC<br>CGGGGTGGTGCCCATCCTGGTCGAGCTGGACGGCGACGTAAACG<br>GCCACAAGTTCAGCGTGTCCGGCGAGGGCGAGGGCGATGCCACC<br>TACGGCAAGCTGACCCTGAAGTTCATCTGCACCACCGGCAAGCT<br>GCCCGTGCCCTGGCCCACCCTCGTGACCACCCTGACCTACGGCG<br>TGCAGTGCTTCAGCCGCTACCCCGACCACATGAAGCAGCACGAC<br>TTCTTCAAGTCCGCCATGCCCGAAGGCTACGTCCAGGAGCGCAC<br>CATCTTCTTCAAGGACGACGGCAACTACAAGACCCGCGCCGAGG<br>TGAAGTTCGAGGGCGACACCCTGGTGAACCGCATCGAGCTGAAG<br>GGCATCGACTTCAAGGAGGACGGCAACATCCTGGGGCACAAGCT<br>GGAGTACAACTACAACAGCCACAACGTCTATATCATGGCCGACA<br>AGCAGAAGAACGGCATCAAGGTGAACTTCAAGATCCGCCACAAC<br>ATCGAGGACGGCAGCGTGCAGCTCGCCGACCACTACCAGCAGAA<br>CACCCCCATCGGCGACGGCCCCGTGCTGCTGCCCGACAACCACT<br>ACCTGAGCACCCAGTCCGCCCTGAGCAAAGACCCCAACGAGAAG<br>CGCGATCACATGGTCCTGCTGGAGTTCGTGACCGCCGCCGGGAT<br>CACTCTCGGCATGGACGAGCTGTACAAGTAAAGCTTAATAAAAG<br>ATCTTTATTTTCATTAGATCTGTGTGTTGGTTTTTTGTGTGCTG<br>GGGGACTCGAGTTAAGGGCgaattcccgataaggatcttcctaga<br>gcatggctacgtagataagtagcatggcgggttaatcattaact<br>acaaggaaccccctagtgatggagttggccactccctctctgcgc<br>gctcgctcgctcactgaggccgggcgaccaaaggtcgcccgacg<br>cccgggctttgcccgggcggcctcagtgagcgagcgagcgcgca<br>g | |
| AAV<br>Human<br>PKP2a<br>Expression<br>Cassette<br>(PKP2<br>promoter,<br>codon<br>optimized) | ctgcgcgctcgctcgctcactgaggccgccccgggcaaagcccgg<br>gcgtcgggcgacctttggtcgcccggcctcagtgagcgagcgag<br>cgcgcagagagggagtggccaactccatcactaggggttccttg<br>tagttaatgattaacccgccatgctacttatctacgtagccatg<br>ctctaggaagatcggaattcGCCCTTAACATCTCAGCATCATGG<br>TTGGATGTTTCCACCTGGCTACATAAGCAAGCTTTACACAAGGT<br>GTAATTTGCCTAAATAGTGGTCCATTCTATTGGGGTGGGAGCAA<br>TTGCTTCCAGGACTCACATCCATATGGCTCCCACTTAGCCATGT<br>GGCCTGCTGACAAAGGGTGGCGGAACTGTCACTACTCTGTTGTC<br>CACGCTTTCAGTCCTTTGGTTTCCTCTTCACTCCCTGGACGCTC<br>ATGTAAAAAGGGAGGCCATATACCTGTGCATTGTGTCTAAGC<br>ATTCAGTGTGTCTAAAGGCAGAAGGGTGTGGGTAGGAAAACA<br>AAGACGAGGGAAGCTGCGTTCTCCAAACACTTCAGACTTAGTA<br>AGTGGGGTTTTGCAGCAATTGAGTGATTTGAGGGAAAGTGAACA<br>TACAAACCCAAGCAATGAAAGGGAATATTATCTTAATACCAGGG<br>ATACATGTTTTTCTTTCTGCCTCTTAAGTCCAAAGAGGCAAATC<br>AGGACAAGTGGCTTTGGTTGTAAACTTTAAGGTCAAGGATCCTT<br>TCTGTTGAGCTTAGCTCTCAAGTTCTCAGTAGTCAACTGCGGTG<br>AAACATAATTAATAGCACGATAAATACAAGTTGTGGAAGATTCG<br>ATTGAAAGTTGGAGGCCCTCTCCGTGGATCTCTCTACAAAGAGC<br>CTGTAATAAAGAGGACTTAATCAACGTTAGCAGGGCTATTTAAA<br>AAGCATCGTCTATTAAAATTCATTTCTTCTCTAGAGCCTCTTGT<br>TGGAGTTTCTCTGTGTGGGTGTGTTCGTAAGAGAGGAATGGGTT<br>AGCAAGAGTACTGGGTACAATTTGTGTATCCAAGAGAAAACAGA<br>AGCTCTCAATGAGGAAGACATATGTTTCTGGGACTGCATCTGTG<br>CAAAAAGTACATAGTCCTGACGTTGTACTAAGAAAAAAAACACT | 6 |

TABLE 1-continued

Sequences

| Name | Sequence | SEQ ID NO: |
|---|---|---|
| | CTCTTTAGAAAGTCTTTTATTTCACACGTTATCTTCTTGGCACA | |
| | TTTCCCTCATATTGCCCTTTCCGCCTGACCAAATAGCCCTTTCT | |
| | CACCCTCAGGTCCAGGAAAACCAGGAAACGTTTCCAACAGTGCG | |
| | ACAAAGCCTGACTAACCAGACATACTACTCGCTCGGGGATCCCG | |
| | GAGGCAAGCCTCAGTCCAAGAACAGGAGTGACTCTCGAGGGCTC | |
| | ACCTGCCTGCAGGGCAGCCCCTCCCTGCATCGAGCGGAAATCCA | |
| | TCCTGTCCAGCGCGGGGCGTGGGCAGAGCGGGGCGCGGCCCCGG | |
| | CAGGCGGTATCCGCTGGGACTCCGACAACGTGCGCGACCCCAGG | |
| | CGAACCGCGCCCCTCTCCCCACCTCCCCGCGGGCGGGTACAAGT | |
| | CTCCAGGTGTCCGCGCGCTCAGCGGGTCCGGCCCGCCCCCGCCC | |
| | CCGCCCCCGGGCCCGACTGCGCGTGCCCGGCCGGAGCCGCGCCC | |
| | CCTCCTCAGGGAAGGCCGGGCGTCCGGCCCACGAGGCCGAGCTC | |
| | CCCCCCGGCCCGGGCCTCTCACCGGCGCGGGGGGCGGGCCAGGG | |
| | GCGGGGCCGGACTCGAGCGGGGCGGGGCTCGCGCCAGCGCCCCC | |
| | AGCTCCGTGGCGGCTTCGCCCGCGAGTCCAGAGGCAGGCGAGCA | |
| | GCTCGGTCGCCCCCACCGGCCCCATGGCTGCTCCTGGTGCTCCT | |
| | GCCGAGTACGGCTACATCAGAACAGTGCTGGGCCAGCAGATCCT | |
| | GGGACAGCTGGATTCTAGCTCTCTGGCCCTGCCTTCTGAGGCCA | |
| | AGCTGAAACTGGCCGGCAGTTCTGGAAGAGGCGGCCAGACAGTG | |
| | AAGTCCCTGCGGATCCAAGAACAGGTGCAGCAGACCCTGGCCAG | |
| | AAAGGGCAGATCTTCTGTCGGCAACGGCAACCTGCACAGAACCA | |
| | GCTCTGTGCCCGAGTACGTGTACAATCTGCACCTGGTGGAAAAC | |
| | GACTTCGTCGGCGGCAGATCCCCTGTGCCTAAGACCTACGATAT | |
| | GCTGAAGGCCGGCACCACCGCCACCTATGAAGGCAGATGGGGAA | |
| | GAGGCACAGCCCAGTACAGCAGCCAGAAAAGCGTGGAAGAGAGA | |
| | AGCCTGCGGCACCCTCTGCGGAGACTGGAAATCAGCCCTGATAG | |
| | CAGCCCAGAGAGAGCCCACTACACCCACAGCGACTACCAGTACT | |
| | CCCAGAGATCTCAGGCCGGCCACACACTGCACCACCAAGAGTCT | |
| | AGAAGGGCCGCTCTGCTGGTGCCTCCTAGATACGCCAGATCTGA | |
| | GATCGTGGGCGTGTCCAGAGCCGGCACAACAAGCAGACAGAGAC | |
| | ACTTCGACACCTACCACCGGCAGTATCAGCACGGCAGCGTGTCC | |
| | GATACCGTGTTCGATAGCATCCCCGCCAATCCTGCTCTGCTGAC | |
| | ATACCCTAGACCTGGCACCTCCAGATCCATGGGCAATCTGCTGG | |
| | AAAAAGAGAACTACCTGACCGCCGGACTGACCGTGGGACAAGTT | |
| | CGACCTCTGGTTCCTCTGCAGCCCGTGACACAGAACAGAGCCAG | |
| | CAGAAGCAGCTGGCACCAGTCCAGCTTCCACAGCACCAGAACAC | |
| | TGAGAGAAGCTGGCCCTAGCGTGGCCGTGGATTCTTCTGGTAGA | |
| | AGGGCTCACCTGACAGTTGGCCAAGCAGCTGCAGGCGGAAGCGG | |
| | AAATCTGCTGACCGAGAAGCACCTTCACCGACAGCCAGCTGG | |
| | GCAACGCCGACATGGAAATGACACTGGAACGGGCCGTGTCCATG | |
| | CTGGAAGCCGATCACATGCTGCCCAGCAGAATTAGCGCCGCTGC | |
| | CACCTTTATCCAGCACGAGTGCTTCCAGAAGTCTGAGGCCCGGA | |
| | AGAGAGTGAACCAGCTGAGAGGCATCCTGAAGCTGCTGCAGCTC | |
| | CTGAAGGTGCAGAACGAGGATGTGCAGAGGGCTGTGTGTGGGGC | |
| | CCTGAGAAATCTGGTGTTCGAGGACAACGACAACAAGCTGGAAG | |
| | TGGCCGAGCTGAACGGCGTGCCAAGACTGCTGCAGGTTCTGAAA | |
| | CAGACCCGCGACCTGGAAACAAAGAAGCAGATCACCGGCCTGCT | |
| | CTGGAACCTGAGCAGCAACGACAAGCTGAAGAACCTGATGATCA | |
| | CAGAGGCCCTGCTGACCCTGACAGAGAACATCATCATCCCTTTC | |
| | AGCGGCTGGCCCGAGGGCGATTACCCTAAAGCTAATGGCCTGCT | |
| | GGACTTCGACATCTTCTACAACGTGACCGGCTGCCTGAGAAACA | |
| | TGTCTAGCGCTGGCGCCGATGGCAGAAAGGCCATGAGAAGATGT | |
| | GACGGCCTGATCGACAGCCTGGTGCACTATGTGCGGGGCACAAT | |
| | CGCCGATTACCAGCCTGATGATAAGGCCACCGAGAACTGCGTGT | |
| | GCATCCTGCACAACCTGAGCTACCAGCTGGAAGCAGAGCTGCCC | |
| | GAGAAGTACAGCCAGAACATCTACATCCAGAACCGGAACATCCA | |
| | GACCGACAACAACAAGAGCATCGGCTGCTTCGGCAGCCGCAGCC | |
| | GGAAAGTGAAAGAACAGTACCAGGACGTGCCCATGCCTGAGGAA | |
| | AAGTCTAACCCCAAAGGCGTGGAATGGCTGTGGCACAGCATCGT | |
| | GATCCGGATGTACCTGAGCCTGATCGCCAAGAGCGTGCGGAATT | |
| | ACACCCAAGAGGCATCTCTGGGCGCCCTGCAGAATCTGACAGCA | |
| | GGATCTGGCCCTATGCCTACCTCTGTGGCTCAGACCGTGGTGCA | |
| | GAAAGAGTCTGGCCTGCAGCACACCCGGAAGATGCTGCATGTGG | |
| | GAGATCCCAGCGTGAAGAAAACCGCCATCAGCCTGCTGAGAAAC | |
| | CTGAGCCGGAATCTGTCTCTGCAGAATGAGATCGCCAAAGAGAC | |
| | ACTGCCCGACCTGGTGTCTATCATCCCTGACACCGTGCCTAGCA | |
| | CCGACCTGCTGATTGAGACAACAGCCAGCGCCTGCTACACCCTG | |
| | AACAACATCATTCAGAACTCCTACCAGAACGCCCGCGATCTGCT | |
| | GAACACAGGCGGCATCCAGAAAATCATGGCCATCTCTGCCGGCG | |
| | ACGCCTACGCCTCTAACAAGGCCTCTAAAGCCGCCAGCGTGCTG | |
| | CTGTATTCTCTGTGGGCCCATACCGAGCTGCACCATGCCTATAA | |
| | GAAGGCCCAGTTCAAAAAGACCGACTTCGTGAACAGCCGGACCG | |
| | CCAAGGCCTACCACTCTCTGAAAGATGTCGACGGATCCGGTACC | |
| | GATTACAAGGACGACGATGACAAGTGAAGCTTAATAAAAGATCT | |
| | TTATTTTCATTAGATCTGTGTGTTGGTTTTTTGTGTGCTGGGGA | |

TABLE 1-continued

Sequences

| Name | Sequence | SEQ ID NO: |
|---|---|---|
| | CTCGAGTTAAGGGCgaattcccgataaggatcttcctagagcat<br>ggctacgtagataagtagcatggcgggttaatcattaactacaa<br>ggaacccctagtgatggagttggccactccctactgcgcgctcg<br>ctcgctcactgaggccgggcgaccaaaggtcgcccgacgcccgg<br>gattgcccgggcggcctcagtgagcgagcgagcgcgcag | |
| AAV9 genome sequence | TTGGCCACTCCCTCTCTGCGCGCTCGCTCGCTCACTGAGGCCGG<br>GCGACCAAAGGTCGCCCGACGCCCGGGCTTTGCCCGGGCGGCCT<br>CAGTGAGCGAGCGAGCGCGCAGAGAGGGAGTGGCCAACTCCATC<br>ACTAGGGGTTCCTGGAGGGGTGGAGTCGTGACGTGAAGTACGTC<br>ATAGGGTTAGGGAGGTCCTGTATTAGAGGTCACGTGAGTGTTTT<br>GCGACATTTTGCGACACCATGTGGTTACGCTGGGTATTTAAGCC<br>CGAGTGAGCACGCAGGGTCTCCATTTTGAAGCGGGAGGTTTGAA<br>CGCGCAGCCGCCATGCCGGGGTTTTACGAGATTGTGATTAAGGT<br>CCCCAGCGACCTTGACGAGCATCTGCCCGGTATTTCTGACAGCT<br>TTGTGAACTGGGTGGCCGAGAAAGAATGGGAGTTGCCGCCAGAT<br>TCTGACATGGATCTGAATCTGATTGAGCAGGCACCCCTGACCGT<br>AGCCGAGAAACTGCAGCGCGACTTTCTGACAGAATGGCGCCGTG<br>TGAGTAAGGCCCCCGAGGCCCTCTTTTTTGTGCAATTTGAAAAG<br>GGAGAGAGCTACTTCCACATGCACGTGCTGGTGGAGACCACCGG<br>GGTGAAGTCCATGGTTTTGGGACGTTTCCTGAGTCAGATTCGCG<br>AAAAACTGATTCAGAGAATTTACCGCGGGATCGAGCCGACTTTG<br>CCAAATTGGTFCGCGGTCACAAAGACCCGAAATGGCGCCGGAGG<br>CGGGAACAAGGTGGTGGACGAGTGCTACATCCCCAATTACCTGC<br>TCCCTAAAACCCAGCCTGAGCTCCAGTGGGCGTGGACTAATATG<br>GAACAGTATTTAAGCGCCTGTTTGAACCTCGCGGAGCGTAAACG<br>GTTGGTGGCGCAGCATCTGACGCACGTGTCGCAGACCCAGGAGC<br>AGAACAAAGAAAATCAGAATCCCAATTCTGACGCGCCGGTGATC<br>AGATCAAAAACCTCAGCCAGGTACATGGAGCTGGTCGGGTGGCT<br>CGTGGACAAGGGGATTACCTCCGAGAAACAGTGGATTCAGGAGG<br>ACCAGGCTTCATACATCTCCTTCAATGCGGCCTCCAACTCGCGG<br>TCTCAAATCAAGGCTGCTCTGGACAATGCGGGAAAGATTATGAG<br>CCTCACTAAAACCGCCCCCGACTACCTGGTGGGCCAGCAGCCCG<br>TGGAGGACATTTCCGGCAATCGGATTTATAAAATCTTGGAACTG<br>AACGGGTACGATCCCCAATACGCGGCTTCCGTCTTTCTGGGATG<br>GGCCACGAAAAAGTTCGGCAAGAGGAACACCATCTGGCTGTTTG<br>GGCCTGCAACTACCGGGAAGACCAACATCGCGGAGGCCATAGCC<br>CACACGGTGCCCTTCTACGGGTGCGTAAACTGGACCAACGAGAA<br>CTTTCCCTTTAACGACTGCGTCGACAAGATGGTGATTTGGTGGG<br>AGGAGGGGAAGATGACCGCCAAGGTCGTGGAATCGGCCAAAGCC<br>ATTCTCGGAGGAAGCAAGGTGCGCGTGGACCAGAGAATGCAAGTC<br>CTCGGCCCAGATAGACCCGACTCCCGTGATCGTCACCTCCAACA<br>CCAACATGTGCGCCGTGATTGACGGGAACTCAACGACCTTCGAG<br>CACCAGCAGCCGTTGCAAGACCGGATGTTCAAATTTGAACTCAC<br>CCGCCGTCTGGATCATGACTTTGGGAAGGTCACCAAGCAGGAAG<br>TCAAAGACTTTTTCCGGTGGGCAAAGGATCACGTGGTTGAGGTG<br>GAGCATGAATTCTACGTCAAAAAGGGTGGAGCTAAGAAAAGGCC<br>CGCCCCCAGTGACGCAGATATAAGTGAGCCCAAACGGGCGCGCG<br>AGTCAGTTGCGCAGACATCGACGTCAGACGCGGAAGCTTCGATC<br>AACTACGCGGACAGGTACCAAAACAAATGTTCTCGTCACGTGGG<br>CATGAATCTGATGCTGTTTCCGTGCAAAACCTGCGAGAGAATGA<br>ATCAGATTTCAAATGTCTGTTTCACGCACGGTGTCAAAGACTGT<br>GGGGAGTGCTTTCCCGTGTCAAAATCTCAACCCGTTTCTGTCGT<br>CAAAAAGAAGACTTATCAGAAACTGTGTCCAATTCATCACATTT<br>TGGGAAGAGCACCCGAGATTGCGTGTTCGGCCTGCGATATGGCC<br>AATGTGGACTTGGATGACTGTGTTTCTGAACAATAAATGACTTA<br>AACCAGGTATGGCTGCCGATGGTTATCTTCCAGATTGGCTCGAG<br>GACAACCTCAGTGAAGGAATTCGCGAGTGGTGGCTTTGAAACC<br>TGGAGCCCCTCAACCCAAGGCAAATCAACAACATCAIAGACAAC<br>GCTCGGGGTCTTGTGCTTCCGGGTTACAAATACCTTGGACCCGG<br>CAACGGACTCGACAAGGGGGAGCCGGTCAACGCAGCAGACGCGG<br>CGGCCCTCGAGCACGACAAGGCATACGACAAGCAGCTCAAGGCC<br>GGAGACAACCCGTACCTCAAGTACAACCACGCCGACGCGGAGTT<br>TCAGGAGCGTCTTAAAGAAGATACGTCTTTTGGGGCAACCTCG<br>GACGAGCAGTCTTCCAGGCGAAAAAGAGGGTTCTCGAACCTCTG<br>GGCCTGGTTGAGGAACCTGTTAAGACGGCTCCGGGAAAAAAGAG<br>GCCGGTAGAGCACTCTCCTGCGGAGCCAGATTCCTCCTCCGGAA<br>CTGGAAAGTCGGGCCAACAGCCTGCAAGAAAAAGATTGAATTTT<br>GGTCAGACTGGAGACGCAGACTCCGTACCTGACCCCCAGCCTCT<br>CGGACAGCACCACCAGCAGCCCCCTCTGGTCTGGGATCTACTACAA<br>TGGCTACAGGCAGTGGCGCACCAATGGCAGACAATAACGAGGGT<br>GCCGATGGAGTGGGTAATTCCTCAGGAAATTGGCATTGCGATTC<br>CCAATGGCTGGGCGACAGAGTCATCACCACCAGCACCCGAACCT<br>GGGCCCTGCCCACCTACAACAATACCTCTACAAGCAAATCTCC<br>AGCCAATCAGGAGCTTCGAACGACAACCACTACTTTGGCTACAG | 7 |

TABLE 1-continued

Sequences

| Name | Sequence | SEQ ID NO: |
|---|---|---|
| | CACCCCTTGGGGGTATTTTGACTTCAACAGATTCCACTGCCACT<br>TTTCACCACGTGACTGGCAAAGACTCATCAACAACAACTGGGGA<br>TTCCGACCCAAGAGACTCAACTTCAAGCTCTTTAACATTCAAGT<br>CAAAGAGGTCACGCAGAATGACGGTACGACGACGATTGCCAATA<br>ACCTTACCAGCACGGTTCAGGTGTFTACTGACTCGGAGTACCAG<br>CTCCCGTACGTCCICGGCTCGGCGCATCAAGGATGCCTCCCGCC<br>GTTTCCAGCGGACGTCTTCATGGTGCCACAGTATGGATACCTCA<br>CCCTAAACAACGGGAGTCAGGCGGTAGGACGCTCTTCCTTTTAC<br>TGCCTGGAGTACTTTCCTTCTCAGATGCTGCGTACAGGAAACAA<br>CTTTCAGTTCAGCTACACTTTTGAAGACGTGCCTTTCCACAGCA<br>GCTACGCTCACAGCCAGAGTCTGGATCGGCTAATGAATCCTCTG<br>ATCGACCAGTACCTGTATTATCTAAACAGGACACAAACAGCCAG<br>TGGAACTCAGCAGTCTCGGCTACTGTTTAGCCAAGCTGGACCCA<br>CCAGCATGTCTCTTCAAGCTAAAAACTGGCTGCCTGGACCTTGC<br>TACAGACAACAGCGTTTGTCAAAGCAGGCAAACGACAACAACAA<br>TAGCAACTTFCCCTGGACTGCGGCTACAAAGTACCACCTCAATG<br>GCAGAGACTCTCTGGTGAATCCGGGCCCTGCTATGGCCAGTCAC<br>AAAGACGATGAAGAAAAGTTTTTCCCCATGCATGGAACCCTGAT<br>ATTTGGTAAAGAAGGAACAAATGCTACCAACGCGGATTTGGACA<br>ATGTCATGATTACAGATGAAGAAGAAATCCGCACCACAAATCCT<br>GTAGCTACGGAGCAGTATGGATATGTGTCAAATAATTTGCAAAA<br>CTCAAATACTGCTGCAACTACTGAAACTGTCAATCACCAAGGAG<br>CGTTACCTGGTATGGTGTGGCAGGATAGAGACGTGTACCTGCAG<br>GGACCCATTTGGGCCAAAATTCCTCACACCGATGGACACTTTCA<br>TCCTTCTCCGCTGATGGGAGGTTTTGGACTCAAACACCCACCTC<br>CTCAGATCATGATCAAAAACACTCCCGTTCCAGCCAATCCTCCC<br>ACAAACTTTAGTGCGGCAAAGTTTGCTTCTTTCATCACACAGTA<br>TTCCACGGGGCAAGTCAGCGTGGAGATCGAGTGGGAGCTGCAGA<br>AGGAGAACAGCAAACGCTGGAACCCCGAGATCCAGTACACTTCC<br>AACTACAACAAATCTGTTAATGTGGACTTTACTGTGGACACTAA<br>TGGTGTGTATTCAGAGCCTCGCCCCATTGGCACCAGATACCTGA<br>CTCGTAATCTGTAATTGCTTGTTAATTAATAAACCGTTTAATTC<br>GTTTCAGTTAAACTTTGGTCTCTGCGTACTTCTTTCTTATCTAG<br>TTTTCCATGGCTACGTAGATAAGTACCATGGCGGGTAATCATTA<br>ACTCTAAGGAACCCCTAGTGATGGAGTTGGCCACTCCCTCTCTG<br>CGCGCTCGCTCGCTCACTGAGGCCGCCCGGGCAAAGCCCGGGCG<br>TCGGGCGACCTTTGGTCGCCCGGCCTCAGTGAGCGAGCGAGCGC<br>GCAGAGAGGGAGTGGCCAA | |
| PKP2 Protein | MAAPGAPAEYGYIRTVLGQQILGQLDSSSLALPSEAKLKLAGSS<br>GRGGQTVKSLRIQEQVQQTLARKGRSSVGNGNLHRTSSVPEYVY<br>NLHLVENDFVGGRSPVPKTYDMLKAGTTATYEGRWGRGTAQYSS<br>QKSVEERSLRHPLRRLFISPDSSPERAHYTHSDYQYSQRSQAGH<br>TLHHQESRRAALLVPPRYARSEIVGVSRAGTTSRQRHFDTYHRQ<br>YQHGSVSDTVFDSIPANPALLTYPRPGTSRSMGNLLEKENYLTA<br>GLTVGQVRPLVPLQPVTQNRASRSSWHQSSFHSTRTLREAGPSV<br>AVDSSGRRAHLTVGQAAAGGSGNLLTERSTFTDSQLGNADMEMT<br>LERAVSMLEADHMLPSRISAAATFTQHECFQKSEARKRVNQLRG<br>ILKLLQLLKVQNEDVQRAVCGALRNLVFEDNDNKLEVAELNGVP<br>RLLQVLKQTRDLETKKQITGLLWNLSSNDKLKNLMITEALLTLT<br>ENIIIPFSGWPEGDYPKANGLLDFDIFYNVTGCLRNMSSAGADG<br>RKAMRRCDGLIDSLVHYVRGTIADYQPDDKATENCVCILHNLSY<br>QLEAELPEKYSQNIYIQNRNIQTDNNKSIGCFGSRSRKVKEQYQ<br>DWMPEEKSNPKGVEWLWHSIVIRMYLSLIAKSVRNYTQEASLGA<br>LQNLTAGSGPMPTSVAQTVVQKESGLQHTRKMLHVGPPSVKKTA<br>ISLLRNLSRNLSLQNEIAKETLPDLVSIIPDTWSTDLLIETTAS<br>ACYTLNNIIQNSYQNARDLLNTGGIQKIMAISAGDAYASNKASK<br>AASVLLYSLWAHTFXHHAYKKAQFKKTDFVNSRTAKAYHSLKD | 8 |
| WPRE | TCAACCTCTGGATTACAAAATTTGTGAAAGATTGACTGGTATTC<br>TTAACTATGTTGCTCCTTTTACGCTATGTGGATACGCTGCTTTA<br>ATGCCTTTGTATCATGCTATTGCTTCCCGTATGGCTTTCATTTT<br>CTCCTCCTTGTATAAATCCTGGTTGCTGTCTCTTTATGAGGAGTT<br>GTGGCCCGTTGTCAGGCAACGTGGCGTGGTGTGCACTGTGTTTG<br>CTGACGCAACCCCCACTGGTTGGGGCATTGCCACCACCTGTCAG<br>CTCCTTTCCGGGACTTTCGCTTTCCCCCTCCCTATTGCCACGGC<br>GGAACTCATCGCCGCCTGCCTTGCCCGCTGCTGGACAGGGGCTC<br>GGCTGTTGGCACTGACAATTCCGTGGTGTTGTCGGGGAAATCA<br>TCGTCCTTTCCTTGGCTGCTCGCCTGTGTTGCCACCTGGATTCT<br>GCGCGGGACGTCCTTCTGCTACGTCCCTTCGGCCCTCAATCCAG<br>CGGACCTTCCTTCCCGCGGCCTGCTGCCGGCTCTGCGGCCTCTT<br>CCGCGTCTTCG | 9 |

TABLE 1-continued

Sequences

| Name | Sequence | SEQ ID NO: |
|---|---|---|
| hGH polyA signal | CCTCGACTGTGCCTTCTAGTTGCCAGCCATCTGTTGTTTGCCCC TCCCCCGTGCCTTCCTTGACCCTGGAAGGTGCCACTCCCACTGT CCTTTCCTAATAAAATGAGGAAATTGCATCGCATTGTCTGAGTA GGTGTCATTCTATTCTGGGGGGTGGGGTGGGGCAGGACAGCAAG GGGGAGGATTGGGAAGACAATAGCAGGCATGCTGGGGACTGGGG A | 10 |
| WPRE - hGH polyA signal cassette | TCAACCTCTGGATTACAAAATTTGTGAAAGATTGACTGGTATTC TTAACTATGTTGCTCCTTTTACGCTATGTGGATACGCTGCTTTA ATGCCTTTGTATCATGCTATTGCTTCCCGTATGGCTTTCATTTT CTCCTCCTTGTATAAATCCTGGTTGCTGTCTCTTTATGAGGAGT TGTGGCCCGTTGTCAGGCAACGTGGCGTGGTGTGCACTGTGTTT GCTGACGCAACCCCCACTGGTTGGGGCATTGCCACCACCTGTCA GCTCCTTTCCGGGACTTTCGCTTTCCCCCTCCCTATTGCCACGG CGGAACTCATCGCCGCCTGCCTTGCCCGCTGCTGGACAGGGGCT CGGCTGTTGGGCACTGACAATTCCGTGGTGTTGTCGGGGAAATC ATCGTCCTTTCCTTGGCTGCTCGCCTGTGTTGCCACCTGGATTC TGCGCGGGACGTCCTTCTGCTACGTCCCTTCGGCCCTCAATCCA GCGGACCTTCCTTCCCGCGGCCTGCTGCCGGCTCTGCGGCCTCT TCCGCGTCTTCGAGATCTGCCTCGACTGTGCCTTCTAGTTGCCA GCCATCTGTTGTTTGCCCCTCCCCCGTGCCTTCCTTGACCCTGG AAGGTGCCACTCCCACTGTCCTTTCCTAATAAAATGAGGAAATT GCATCGCATTGTCTGAGTAGGTGTCATTCTATTCTGGGGGGTGG GGTGGGGCAGGACAGCAAGGGGGAGGATTGGGAAGACAATAGCA GGCATGCTGGGGACTGGGGACTCGAGTTAAGGGCGAATTCCCGA TAAGGATCTTCCTAGAGCATGGCTACGTAGATAAGTAGCATGGC GGGTTAATCATTAACTACA | 11 |

Viral Vectors

Suitable viral vectors for methods and gene therapy vectors provided herein include, but are not limited to, viral vectors (e.g. viral vectors based on vaccinia virus; poliovirus; adenovirus (e.g., Li et al. (1994) Invest Opthalmol Vis Sci 35:2543-2549; Borras et al. (1999) Gene Ther 6:515-524; Li and Davidson, (1995) Proc. Natl. Acad. Sci. 92:7700-7704; Sakamoto et al. (1999) Hum Gene Ther 5:1088-1097; WO 94/12649; WO 93/03769; WO 93/19191; WO 94/28938; WO 95/11984 and WO 95/00655); adeno-associated virus (e.g., Ai et al. (1998) Hum Gene Ther 9(1):81-86, 1998, Flannery et al. (1997) Proc. Natl. Acad. Sci. 94:6916-6921; Bennett et al. (1997) Invest Opthalmol Vis Sci 38:2857-2863; Jomary et al. (1997) Gene Ther 4:683-690; Rolling et al. (1999), Hum Gene Ther 10:641-648; Ali et al. (1996) Hum Mol Genet. 5:591-594; WO 93/09239, Samulski et al. (1989) J. Vir. 63:3822-3828; Mendelson et al. (1988) Virol. 166: 154-165; and Flotte et al. (1993) Proc. Natl. Acad. Sci. 90: 10613-10617; SV40; herpes simplex virus; human immunodeficiency virus (e.g., Miyoshi et al. (1997) Proc. Natl. Acad. Sci. 94: 10319-10323; Takahashi et al. (1999) J Virol 73:7812-7816); a retroviral vector (e.g., Murine-Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. Numerous suitable expression vectors are known to those of skill in the art, and many are commercially available. The following vectors are provided by way of example; for eukaryotic cells: pXT1, pSG5 (Stratagene), pSVK3, pBPV, pMSG, pSVLSV40 (Pharmacia), and pAd (Life Technologies). However, any other vector is contemplated for use so long as it is compatible with the methods of the present disclosure.

The ability of certain viruses to infect cells or enter cells via receptor-mediated endocytosis, and express viral genes stably and efficiently have made them attractive candidates for the transfer of foreign nucleic acids into cells (e.g., mammalian cells). Viral vectors are contemplated to include control sequences such as promoters for expression of the polypeptide of interest. Although many viral vectors integrate into the host cell genome, if desired, the segments that allow such integration can be removed or altered to prevent such integration. Moreover, in some embodiments, the vectors do not contain a mammalian origin of replication. Non-limiting examples of virus vectors are described below that are contemplated for use in delivering nucleic acids encoding PKP2 into a selected cell. In some embodiments, the viral vector is derived from a replication-deficient virus.

In general, other useful viral vectors are based on non-cytopathic eukaryotic viruses in which non-essential genes have been replaced with the polypeptide of interest. Non-cytopathic viruses include certain retroviruses, the life cycle of which involves reverse transcription of genomic viral RNA into DNA with subsequent proviral integration into host cellular DNA. In general, the retroviruses are replication-deficient (e.g., capable of directing synthesis of the desired transcripts, but incapable of manufacturing an infectious particle). Such genetically altered retroviral expression vectors have general utility for the high-efficiency transduction of polynucleotide in vivo.

In some embodiments, a polynucleotide encoding PKP2 is housed within an infective virus that has been engineered to express a specific binding ligand. The virus particle will thus bind with specificity to the cognate receptors of the target cell and deliver the contents to the cell. In some embodiments, the virus is modified to impart particular viral tropism, e.g., the virus preferentially infects fibroblasts, heart cells, or more particularly cardiac fibroblasts (CFs). For AAV, in some cases, capsid proteins are mutated to alter the tropism of the viral vector. For example, lentivirus tropism is often modified by using different envelope proteins; this is known as "pseudotyping."

In some embodiments, the viral vector is a retroviral vector. Retroviruses often integrate their genes into the host genome, transfer a large amount of foreign genetic material, infect a broad spectrum of species and cell types, and are often packaged in special cell-lines (Miller et al., Am. J. Clin. Oncol., 15(3):216-221, 1992). In some embodiments, a retroviral vector is altered so that it does not integrate into the host cell genome.

In some embodiments, the recombinant retrovirus comprises a viral polypeptide (e.g., retroviral env) to aid entry into the target cell. Such viral polypeptides are well-established in the art, for example, U.S. Pat. No. 5,449,614. In some embodiments, the viral polypeptide is an amphotropic viral polypeptide, for example, amphotropic env, which aids entry into cells derived from multiple species, including cells outside of the original host species. In some embodiments, the viral polypeptide is a xenotropic viral polypeptide that aids entry into cells outside of the original host species. In some embodiments, the viral polypeptide is an ecotropic viral polypeptide, for example, ecotropic env, which aids entry into cells of the original host species.

Examples of viral polypeptides capable of aiding entry of retroviruses into cells include, but are not limited to: MMLV amphotropic env, MMLV ecotropic env, MMLV xenotropic env, vesicular stomatitis virus-g protein (VSV-g), HIV-1 env, Gibbon Ape Leukemia Virus (GALV) env, RD114, FeLV-C, FeLV-B, MLV 10A1 env gene, and variants thereof, including chimeras. Yee et al. (1994) Methods Cell Biol, Pt A:99-112 (VSV-G); U.S. Pat. No. 5,449,614. In some cases, the viral polypeptide is genetically modified to promote expression or enhanced binding to a receptor.

In embodiments, the retroviral construct is derived from a range of retroviruses, e.g., MMLV, HIV-1, SIV, FIV, or other retrovirus described herein. In some embodiments, the retroviral construct encodes all viral polypeptides necessary for more than one cycle of replication of a specific virus. In some cases, the efficiency of viral entry is improved by the addition of other factors or other viral polypeptides. In other cases, the viral polypeptides encoded by the retroviral construct do not support more than one cycle of replication, e.g., U.S. Pat. No. 6,872,528. In such circumstances, the addition of other factors or other viral polypeptides often help facilitate viral entry. In an exemplary embodiment, the recombinant retrovirus is HIV-1 virus comprising a VSV-g polypeptide, but not comprising a HIV 1 env polypeptide.

In some embodiments, the retroviral construct comprises: a promoter, a multi-cloning site, and/or a resistance gene. Examples of promoters include but are not limited to CMV, SV40, EFla, β-actin; retroviral LTR promoters, and inducible promoters. In some embodiments, the retroviral construct comprises a packaging signal (e.g., a packaging signal derived from the MFG vector; a psi packaging signal). Examples of some retroviral constructs known in the art include but are not limited to: pMX, pBabeX or derivatives thereof. Onishi et al. (1996) Experimental Hematology, 24:324-329. In some cases, the retroviral construct is a self-inactivating lentiviral vector (SIN) vector. Miyoshi et al. (1998) J. Virol 72(10):8150-8157. In some cases, the retroviral construct is LL-CG, LS-CG, CL-CG, CS-CG, CLG or MFG. Miyoshi et al. (1998) J. Virol 72(10):8150-8157; Onishi et al. (1996) Experimental Hematology, 24:324-329; Riviere et al. (1995) Proc. Natl. Acad. Sci., 92:6733-6737.

In some embodiments, a retroviral vector is constructed by inserting a nucleic acid (e.g., one encoding a polypeptide of interest or an RNA) into the viral genome in the place of some viral sequences to produce a virus that is replication-defective. To produce virions, a packaging cell line containing the gag, pol, and env genes, but without the LTR and packaging components, is constructed (Mann et al., Cell 33:153-159, 1983). When a recombinant plasmid containing a cDNA, together with the retroviral LTR and packaging sequences is introduced into a special cell line (e.g., by calcium phosphate precipitation or lipid transfection), the packaging sequence allows the RNA transcript of the recombinant plasmid to be packaged into viral particles, which are then secreted into the culture media (Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986; Mann et al., Cell, 33:153-159, 1983). The media containing the recombinant retroviruses is then collected, optionally concentrated, and used for gene transfer. Retroviral vectors are able to infect a broad variety of cell types. However, integration and stable expression typically involves the division of host cells (Paskind et al., Virology, 67:242-248, 1975).

In some embodiments, the viral vector is a lentiviral vector. Lentiviruses are complex retroviruses, which, in addition to the common retroviral genes gag, pol, and env, contain other genes with regulatory or structural function. Information on lentiviral vectors is available, for example, in Naldini et al., Science 272(5259):263-267, 1996; Zufferey et al., Nat Biotechnol 15(9):871-875, 1997; Blomer et al., J Virol. 71(9):6641-6649, 1997; U.S. Pat. Nos. 6,013,516 and 5,994,136, each of which is incorporated herein by reference in its entirety. Some examples of lentivirus include the Human Immunodeficiency Viruses: HIV-1, HIV-2 and the Simian Immunodeficiency Virus: SIV. Lentiviral vectors have been generated by attenuating the HIV virulence genes, for example, the genes env, vif, vpr, vpu and nef are deleted to make the vector biologically safe. The lentivirus employed is sometimes replication and/or integration defective.

Recombinant lentiviral vectors are capable of infecting non-dividing cells and are sometimes used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, which is incorporated herein by reference in its entirety. In some embodiments, the recombinant virus is targeted by linkage of the envelope protein with an antibody or a particular ligand for targeting to a receptor of a particular cell type. For example, a target-specific vector is sometimes generated by inserting a nucleic acid segment (including a regulatory region) of interest into the viral vector, along with another gene that encodes a ligand for a receptor on a specific target cell type.

Lentiviral vectors are known in the art, see Naldini et al., (1996 and 1998); Zufferey et al., (1997); Dull et al., 1998, U.S. Pat. Nos. 6,013,516; and 5,994,136 all incorporated herein by reference. In general, these vectors are plasmid-based or virus-based, and are configured to carry the essential sequences for incorporating foreign nucleic acid, for selection and for transfer of the nucleic acid into a host cell. In some cases, a lentiviral vector is introduced into a cell concurrently with one or more lentiviral packaging plasmids, which include, without limitation, pMD2.G, pRSV-rev, pMDLG-pRRE, and pRRL-GOI. Introduction of a lentiviral vector alone or in combination with lentiviral packaging plasmids into a cell, in some embodiments causes the lentiviral vector to be packaged into a lentiviral particle. In some embodiments, the lentiviral vector is a non-integrating lentiviral (NIL) vector. Illustrative methods for generating NIL vectors, such as the D64V substitution in the integrase gene, are provided in U.S. Pat. No. 8,119,119.

In some embodiments, the viral vector is an adenoviral vector. The genetic organization of adenovirus includes an approximate 36 kb, linear, double-stranded DNA virus, which allows substitution of large pieces of adenoviral DNA with foreign sequences up to 7 kb (Grunhaus et al., Seminar in Virology 200(2):535-546, 1992)). In some cases, PKP2 is introduced into the cell using adenovirus assisted transfection. Increased transfection efficiencies have been reported in cell systems using adenovirus coupled systems (Kelleher and Vos, Biotechniques, 17(6):1110-7, 1994; Cotten et al., Proc Natl Acad Sci USA, 89(13):6094-6098, 1992; Curiel, Nat Immun, 13(2-3):141-64, 1994).

In some embodiments, the viral vector is an adeno-associated virus (AAV) vector. AAV is an attractive vector system as it has a low frequency of integration and it can infect non-dividing cells, thus making it useful for delivery of polynucleotides into mammalian cells, for example, in tissue culture (Muzyczka, Curr Top Microbiol Immunol, 158:97-129, 1992) or in vivo. Details concerning the generation and use of rAAV vectors are described in U.S. Pat. Nos. 5,139,941 and 4,797,368, each incorporated herein by reference in its entirety.

AAV is a replication-deficient parvovirus, the single-stranded DNA genome of which is about 4.7 kb in length including two 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in U.S. Pat. No. 9,434,928, incorporated herein by reference. Cis-acting sequences directing viral DNA replication (rep), encapsidation/packaging and host cell chromosome integration are contained within the AAV TTRs. Three AAV promoters (named p5, p19, and p40 for their relative map locations) drive the expression of the two AAV internal open reading frames encoding rep and cap genes. The two rep promoters (p5 and pi 9), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and often persists essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, in some embodiments, some or all of the internal approximately 4.3 kb of the genome (encoding replication and structural capsid proteins, rep-cap) is replaced with foreign DNA. To generate AAV vectors, in some cases, the rep and cap proteins are provided in trans. Another significant feature of AAV is that it is an extremely stable and hearty virus. It easily withstands the conditions used to inactivate adenovirus (56° to 65° C. for several hours), making cold preservation of AAV less critical. In some cases, AAV is even be lyophilized. Finally, AAV-infected cells are not resistant to superinfection. The AAV vectors of the disclosure include self-complementary, duplexed AAV vectors, synthetic ITRs, and/or AAV vectors with increased packaging compacity. Illustrative methods are provided in U.S. Pat. Nos. 8,784,799; 8,999,678; 9,169,494; 9,447,433; and 9,783,824, each of which is incorporated by reference in its entirety.

AAV DNA in the rAAV genomes is contemplated to be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh74. Production of pseudotyped rAAV is disclosed in, for example, WO 01/83692. Other types of rAAV variants, for example rAAV with capsid mutations, are also contemplated. See, for example, Marsic et al., Mol. Therapy. 22):1900-09 (2014). The nucleotide sequences of the genomes of various AAV serotypes are known in the art. AAV vectors of the present disclosure include AAV vectors of serotypes AAV1, AAV2, AAV4, AAV5, AAV6, AAV7, AAV8, AAV9, AAV10, AAV39, AAV43, AAV.rh74, and AAV.rh8. Illustrative AAV vectors are provided in U.S. 63/012,703; U.S. Pat. No. 7,105,345; U.S. Ser. No. 15/782,980; U.S. Pat. Nos. 7,259,151; 6,962,815; 7,718,424; 6,984,517; 7,718,424; 6,156,303; 8,524,446; 7,790,449; 7,906,111; 9,737,618; U.S. application Ser. No. 15/433,322; U.S. Pat. No. 7,198,951, each of which is incorporated by reference in its entirety.

In some embodiments, the AAV expression vector is pseudotyped to enhance targeting. To promote gene transfer and sustain expression in cardiomyocytes, AAV6, AAV8, and AAV9, are contemplated for use. In some cases, the AAV2 genome is packaged into the capsid of producing pseudotyped vectors AAV2/5, AAV2/7, and AAV2/8 respectively, as described in Balaji et al. J Surg Res. 184:691-98 (2013). In some embodiments, an AAV9 is used to target expression in myofibroblast-like lineages, as described in Piras et al. Gene Therapy 23:469-478 (2016). In some embodiments, AAV1, AAV6, or AAV9 is used, and in some embodiments, the AAV is engineered, as described in Asokari et al. Hum Gene Ther. 24:906-13 (2013); Pozsgai et al. Mol Ther. 25:855-69 (2017); Kotterman et al. Nature Reviews Genetics 15:445-51(2014); and US20160340393A1 to Schaffer et al. In some embodiments, the viral vector is AAV engineered to increase target cell infectivity as described in US20180066285A1.

In some embodiments, the AAV vectors of the disclosure comprise a modified capsid, in particular as capsid engineered to enhance or promote in vivo or ex vivo transduction of cardiac cells, or more particularly cardiomyocytes; or that evade the subject's immune system; or that have improved biodistribution. Illustrative AAV capsids are provided in U.S. Pat. Nos. 7,867,484; 9,233,131; 10,046,016; WO 2016/133917; WO 2018/222503; and WO 20019/060454, each of which is incorporated by reference in its entirety. In an AAV capsid (or in particular an AAV9 capsid), one or more substitutions are contemplated to increase infectivity towards cardiomyocytes. More particularly, in some embodiments, the AAV vectors of the disclosure, optionally AAV9-based vectors, comprise in their capsid proteins one or more substitutions. In some embodiments, the AAV vectors of the disclosure comprise the AAV-A9 capsid and/or serotype. It will be appreciated that these substitutions and insertions are contemplated to be combined together to generate various capsid proteins useful in the present disclosure.

Methods of Producing Viral Vectors

In general, a viral vector is produced by introducing a viral DNA or RNA construct into a producer cell. In some cases, the producer cell does not express exogenous genes. In other cases, the producer cell is a "packaging cell" comprising one or more exogenous genes, e.g., genes encoding one or more gag, pol, or env polypeptides and/or one or more retroviral gag, pol, or env polypeptides. In some embodiments, the retroviral packaging cell comprises a gene encoding a viral polypeptide, e.g., VSV-g, that aids entry into target cells. In some cases, the packaging cell comprises genes encoding one or more lentiviral proteins, e.g., gag, pol, env, vpr, vpu, vpx, vif, tat, rev, or nef. In some cases, the packaging cell comprises genes encoding adenovirus proteins such as El A or El B or other adenoviral proteins. For example, in some cases, proteins supplied by packaging cells are retrovirus-derived proteins such as gag, pol, and env; lentivirus-derived proteins such as gag, pol, env, vpr, vpu, vpx, vif, tat, rev, and nef; and adenovirus-derived proteins such as El A and El B. In many examples, the packaging cells supply proteins derived from a virus that differs from the virus from which the viral vector is derived. Methods of producing recombinant viruses from packaging cells and their uses are well established; see, e.g., U.S. Pat. Nos. 5,834,256; 6,910,434; 5,591,624; 5,817,491; 7,070,994; and 6,995,009.

Packaging cell lines include but are not limited to any easily-transfectable cell line. Packaging cell lines are often based on 293T cells, NIH3T3, COS or HeLa cell lines. Packaging cells are often used to package virus vector plasmids deficient in at least one gene encoding a protein required for virus packaging. Any cells that supply a protein or polypeptide lacking from the proteins encoded by such viral vectors or plasmids are contemplated for use as packaging cells. Examples of packaging cell lines include, but are not limited to: Platinum-E (Plat-E), Platinum-A (Plat-A), BOSC 23 (ATCC CRL 11554) and Bing (ATCC CRL 11270). Morita et al. (2000) Gene Therapy 7(12): 1063-1066; Onishi et al. (1996) Experimental Hematology, 24:324-329; U.S. Pat. No. 6,995,009. Commercial packaging lines are also useful, e.g., Ampho-Pak 293 cell line, Eco-Pak 2-293 cell line, RetroPack PT67 cell line, and Retro-X Universal Packaging System (all available from Clontech).

Virus vector plasmids (or constructs), include: pMXs, pMxs-IB, pMXs-puro, pMXs-neo (pMXs-IB is a vector carrying the blasticidin-resistant gene instead of the puromycin-resistant gene of pMXs-puro) Kimatura et al. (2003) Experimental Hematology 31: 1007-1014; MFG Riviere et al. (1995) Proc. Natd. Acad. Sci., 92:6733-6737; pBabePuro; Morgenstern et al. (1990) Nucleic Acids Research 18:3587-3596; LL-CG, CL-CG, CS-CG, CLG Miyoshi et al. (1998) J. Vir. 72:8150-8157 and the like as the retrovirus system, and pAdexl Kanegae et al. (1995) Nucleic Acids Research 23:3816-3821 and the like as the adenovirus system. In exemplary embodiments, the retroviral construct comprises blasticidin (e.g., pMXs-IB), puromycin (e.g., pMXs-puro, pBabePuro), or neomycin (e.g., pMXs-neo). Morgenstern et al. (1990) Nucleic Acids Research 18:3587-3596.

Promoters and Enhancers

In some embodiments, a nucleic acid encoding a PKP2 is operably linked to a promoter and/or enhancer to facilitate expression of PKP2. Depending on the host/vector system utilized, any of a number of suitable transcription and translation control elements, including constitutive, tissue specific, and inducible promoters, transcription enhancer elements, transcription terminators, etc. are suitable for use in the expression vector (e.g., Bitter et al. (1987) Methods in Enzymology, 153:516-544).

Non-limiting examples of suitable eukaryotic promoters (promoters functional in a eukaryotic cell) include CMV, CMV immediate early, HSV thymidine kinase, early and late SV40, long terminal repeats (LTRs) from retrovirus, and mouse metallothionein-I. In some embodiments, promoters that are capable of conferring cardiac-specific expression will be used. Non-limiting examples of suitable cardiac-specific promoters include alpha-myosin heavy chain (a-MHC), myosin light chain 2 (MLC-2), cardiac troponin T (cTnT), and cardiac troponin C (cTnC). In some embodiments, a PKP2 or a desmin promoter is used. In some cases, a chimeric promoter with cardiac specific expression is used. In some cases, a cardiac specific enhancer is combined with the promoter.

Examples of suitable promoters for driving expression PKP2 include, but are not limited to, retroviral long terminal repeat (LTR) elements; constitutive promoters such as CMV, HSV1-TK, SV40, EF-la, β-actin, phosphoglycerol kinase (PGK); inducible promoters, such as those containing Tet-operator elements; and cardiac-specific promoters, such as alpha-myosin heavy chain (a-MHC), myosin light chain 2 (MLC-2), cardiac troponin T (cTnT), and cardiac troponin C (cTnC). In some embodiments, a PKP2 or a desmin promoter is used. In some embodiments, a chimeric promoter with cardiac specific expression is used. In some cases, a cardiac specific enhancer is combined with the promoter.

In some embodiments, a polynucleotide is operably linked to a cell type-specific transcriptional regulator element (TRE), where TREs include promoters and enhancers. Suitable TREs include, but are not limited to, TREs derived from the following genes: myosin light chain-2, α-myosin heavy chain, AE3, cardiac troponin C, and cardiac actin. Franz et al. (1997) Cardiovasc. Res. 35:560-566; Robbins et al. (1995) Ann. N. Y. Acad. Sci. 752:492-505; Linn et al. (1995) Circ. Res. 76:584-591; Parmacek et al. (1994) Cell.

Biol. 14: 1870-1885; Hunter et al. (1993) Hypertension 22:608-617; and Sartorelli et al. (1992) Proc. Natl. Acad. Sci. USA 89:4047-4051.

Alternatively, certain advantages will be gained by positioning the coding nucleic acid segment under the control of a recombinant or heterologous promoter, which refers to a promoter that is not normally associated with a nucleic acid in its natural environment. A recombinant or heterologous enhancer refers also to an enhancer not normally associated with a nucleic acid sequence in its natural environment. Such promoters or enhancers often include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences are sometimes produced using recombinant cloning and/or nucleic acid amplification technology, including PCR, in connection with the compositions disclosed herein (see U.S. Pat. Nos. 4,683,202, 5,928,906, each incorporated herein by reference).

In some embodiments, the vectors of the disclosure include one or more polyA signals. Illustrative polyA signals useful in the vectors of the disclosure include the short polyA signal and the bGH polyA signal. In some embodiments, the vectors of the disclosure include one or more 3' elements. Illustrative 3' elements include the woodchuck hepatitis virus posttranscriptional regulatory element (WPRE).

Gene Therapy Vector Compositions

To prepare the composition, the vectors and/or the cells are generated, and the vectors or cells are purified as necessary or desired. The vectors, and/or other agents are sometimes suspended in a pharmaceutically acceptable carrier. In some embodiments, the composition is lyophilized. These compounds and cells are often adjusted to an appropriate concentration, and optionally combined with other agents. The absolute weight of a given compound and/or other agent included in a unit dose varies widely. The dose and the number of administrations are contemplated to be optimized by those skilled in the art.

For example, in some embodiments, about $10^2$-$10^{10}$ vector genomes (vg) are be administered. In some embodiments, the dose be at least about $10^2$ vg, about $10^3$ vg, about $10^4$ vg, about $10^5$ vg, about $10^6$ vg, about $10^7$ vg, about $10^8$ vg, about $10^9$ vg, about $10^{10}$ vg, or more vector genomes. In some embodiments, the dose be about $10^2$ vg, about $10^3$ vg, about $10^4$ vg, about $10^5$ vg, about $10^6$ vg, about $10^7$ vg, about $10^8$ vg, about $10^9$ vg, about $10^{10}$ vg, or more vector genomes.

Daily doses of the compounds vary as well. Such daily doses often range, for example, from at least about $10^2$ vg/day, about $10^3$ vg/day, about $10^4$ vg/day, about $10^5$ vg/day, about $10^6$ vg/day, about $10^7$ vg/day, about $10^8$ vg/day, about $10^9$ vg/day, about $10^{10}$ vg/day, or more vector genomes per day.

In some embodiments, the method of the disclosure comprise administering a vector or vector system of the disclosure (e.g. an rAAV vector) by intracardiac injection, intramyocardiac injection, endocardial injection, intracardiac catheterization, or systemic administration. In some embodiments, the subject (e.g., a human) is treated by administering between about $1\times10^8$ and about $1\times10^{15}$ GC of a vector (e.g., an AAV vector or lentiviral vector) by intracardiac injection, intramyocardiac injection, endocardial injection, intracardiac catheterization, or systemic administration. In some embodiments, the subject is treated by administering between about $1\times10^8$ and about $1\times10^{15}$ GC, between about $1\times10^8$ and about $1\times10^{15}$ GC, between about $1\times10^9$ and about $1\times10^{14}$ GC, between about $1\times110^{10}$ and about $1\times10^{13}$ GC, between about $1\times10^{11}$ and about $1\times10^{12}$ GC, or between about $1\times110^{12}$ and about $1\times10^{13}$ GC of vector. In some embodiments, the subject is treated by administering between about $1\times10^8$ and about $1\times10^{10}$ GC, between about $1\times10^9$ and about $1\times10^{11}$ GC, between about $1\times10^{10}$ and about $1\times10^{12}$ GC, between about $1\times10^{11}$ and about $1\times10^{13}$ GC, between about $1\times10^{12}$ and about $1\times10^{14}$ GC, or between about $1\times10^{13}$ and about $1\times10^{15}$ GC of vector. In some embodiments, the subject is treated by administering at least $1\times10^8$, at least about $1\times10^9$, at least about $1\times10^{10}$, at least about $1\times10^{11}$, at least about $1\times10^{12}$, at least about $1\times10^{13}$, or at least about $1\times10^{15}$ GC of vector. In some embodiments, the subject is treated by administering at most $1\times10^8$, at most about $1\times10^9$, at most about $1\times10^{10}$, at most about $1\times10^{11}$, at most about $1\times10^{12}$, at most about $1\times10^{13}$, or at most about $1\times10^{15}$ GC of vector. In some embodiments, the subject (e.g., a human) is treated by administering between about $1\times10^8$ and about $1\times10^{15}$ GC/kg of a vector (e.g., an AAV vector or lentiviral vector) by intracardiac injection or systemically. In some embodiments, the subject is treated by administering between about $1\times10^8$ and about $1\times10^{15}$ GC/kg, between about $1\times10^8$ and about $1\times10^{15}$ GC/kg, between about $1\times10^9$ and about $1\times10^{14}$ GC/kg, between about $1\times10^{10}$ and about $1\times10^{13}$ GC/kg, between about $1\times10^{11}$ and about $1\times10^{12}$ GC/kg, or between about $1\times10^{12}$ and about $1\times10^{13}$ GC/kg of vector. In some embodiments, the subject is treated by administering between about $1\times10^8$ and about $1\times10^{10}$ GC/kg, between about $1\times10^9$ and about $1\times10^{11}$ GC/kg, between about $1\times10^{10}$ and about $1\times10^{12}$ GC/kg, between about $1\times10^{11}$ and about $1\times10^{13}$ GC/kg, between about $1\times10^{12}$ and about $1\times10^{14}$ GC/kg, or between about $1\times10^{13}$ and about $1\times10^{15}$ GC/kg of vector. In some embodiments, the subject is treated by administering at least $1\times10^8$, at least about $1\times10^9$, at least about $1\times10^{10}$, at least about $\mathbf{1\times10^{11}}$, at least about $1\times10^{12}$, at least about $1\times10^{13}$, or at least about $1\times10^{15}$ GC/kg of vector. In some embodiments, the subject is treated by administering at most $1\times10^8$, at most about $1\times10^9$, at most about $1\times10^{10}$, at most about $1\times10^{11}$, at most about $1\times10^{12}$, at most about $1\times10^{13}$, or at most about $1\times10^{15}$ GC/kg of vector. It will be appreciated that the amount of vectors and for use in treatment will vary not only with the particular carrier selected but also with the route of administration, the nature of the condition being treated and the age and condition of the patient. Ultimately, in some embodiments, the attendant health care provider will determine proper dosage. A pharmaceutical composition is contemplated to be formulated with the appropriate ratio of each compound in a single unit dosage form for administration.

The compositions are sometimes formulated for sustained release (for example, using microencapsulation, see WO 94/07529, and/or U.S. Pat. No. 4,962,091). The formulations, where appropriate, are conveniently presented in discrete unit dosage forms and, in some embodiments, are prepared by any of the methods well known to the pharmaceutical arts. Such methods often include the step of mixing the therapeutic agent with liquid carriers, solid matrices, semi-solid carriers, finely divided solid carriers or combinations thereof, and then, if necessary, introducing or shaping the product into the desired delivery system.

One or more suitable unit dosage forms containing the compounds, in some embodiments, are administered by a variety of routes including parenteral (including subcutaneous, intravenous, intramuscular and intraperitoneal), intracardially, pericardially, oral, rectal, dermal, transdermal, intrathoracic, intrapulmonary, and intranasal (respiratory) routes.

The gene therapy vectors provided herein are prepared in many forms that include aqueous solutions, suspensions, tablets, hard or soft gelatin capsules, and liposomes and other slow-release formulations, such as shaped polymeric gels. Administration of gene therapy vectors often involves parenteral or local administration in an aqueous solution. Similarly, compositions containing gene therapy vectors are sometimes administered in a device, scaffold, or as a sustained release formulation. Different types of formulating procedures are described in U.S. Pat. No. 6,306,434 and in the references contained therein.

Vectors, in some embodiments, are formulated for parenteral administration (e.g., by injection, for example, bolus injection or continuous infusion) and are often presented in unit dosage form in ampoules, prefilled syringes, small volume infusion containers or multi-dose containers with an added preservative. The pharmaceutical compositions often take the form of suspensions, solutions, or emulsions in oily or aqueous vehicles, and sometimes contain formulatory agents such as suspending, stabilizing and/or dispersing agents. Suitable carriers include saline solution, phosphate buffered saline, and other materials commonly used in the art.

The compositions sometimes also contain other ingredients such as agents useful for treatment of cardiac diseases, conditions and injuries, such as, for example, an anticoagulant (e.g., dalteparin (fragmin), danaparoid (orgaran), enoxaparin (lovenox), heparin, tinzaparin (innohep), and/or warfarin (coumadin)), an antiplatelet agent (e.g., aspirin, ticlopidine, clopidogrel, or dipyridamole), an angiotensin-converting enzyme inhibitor (e.g., Benazepril (Lotensin), Captopril (Capoten), Enalapril (Vasotec), Fosinopril (Monopril), Lisinopril (Prinivil, Zestril), Moexipril (Univasc), Perindopril (Aceon), Quinapril (Accupril), Ramipril (Altace), and/or Trandolapril (Mavik)), angiotensin II receptor blockers (e.g., Candesartan (Atacand), Eprosartan (Teveten), Irbesartan (Avapro), Losartan (Cozaar), Telmisartan (Micardis), and/or Valsartan (Diovan)), a beta blocker (e.g., Acebutolol (Sectral), Atenolol (Tenormin), Betaxolol (Kerlone), Bisoprolol/hydrochlorothiazide (Ziac), Bisoprolol (Zebeta), Carteolol (Cartrol), Metoprolol (Lopressor, Toprol XL), Nadolol (Corgard), Propranolol (Inderal), Sotalol (Betapace), and/or Timolol (Blocadren)), Calcium Channel Blockers (e.g., Amlodipine (Norvasc, Lotrel), Bepridil (Vascor), Diltiazem (Cardizem, Tiazac), Felodipine (Plendil), Nifedipine (Adalat, Procardia), Nimodipine (Nimotop), Nisoldipine (Sular), Verapamil (Calm, Isoptin, Verelan), diuretics (e.g., Amiloride (Midamor), Bumetanide (Bumex), Chlorothiazide (Diuril), Chlorthalidone (Hygroton), Furosemide (Lasix), Hydro-chlorothiazide (Esidrix, Hydrodiuril), Indapamide (Lozol) and/or Spironolactone (Aldactone)), vasodilators (e.g., Isosorbide dinitrate (Isordil), Nesiritide (Natrecor), Hydralazine (Apresoline), Nitrates and/or Minoxidil), statins, nicotinic acid, gemfibrozil, clofibrate, Digoxin, Digitoxin, Lanoxin, or any combination thereof.

Additional agents are sometimes included such as antibacterial agents, antimicrobial agents, anti-viral agents, biological response modifiers, growth factors; immune modulators, monoclonal antibodies and/or preservatives. The compositions provided herein are contemplated to also be used in conjunction with other forms of therapy.

The viral vectors described herein are suitable for administration to a subject to treat a disease or disorder. In some embodiments, such a composition is in a single dose, in multiple doses, in a continuous or intermittent manner, depending, for example, upon the recipient's physiological condition, whether the purpose of the administration is in response to traumatic injury or for more sustained therapeutic purposes, and other factors known to skilled practitioners. The administration of the compounds and compositions of provided herein, in some embodiments, are administered continuously over a preselected period of time or alternatively are administered in a series of spaced doses. Both local and systemic administration is contemplated. In some embodiments, localized delivery of a viral or non-viral vector is achieved. In some embodiments, localized delivery of cells and/or vectors is used to generate a population of cells within the heart. In some embodiments, such a localized population operates as "pacemaker cells" for the heart.

Definitions

As used herein, the term "cardiomyopathy" refers to any disease or dysfunction of the myocardium (heart muscle) in which the heart is abnormally enlarged, thickened and/or stiffened. As a result, the heart muscle's ability to pump blood is usually weakened. The etiology of the disease or disorder is, in some cases, inflammatory, metabolic, toxic, infiltrative, fibroplastic, hematological, genetic, or unknown in origin. There are two general types of cardiomyopathies: ischemic (resulting from a lack of oxygen) and non-ischemic. In some cases, a cardiomyopathy is arrhythmogenic right ventricular cardiomyopathy (ARVC) or arrhythmogenic cardiomyopathy (ACM).

"Heart failure (HF) is a complex clinical syndrome that often result from any structural or functional cardiovascular disorder causing systemic perfusion inadequate to meet the body's metabolic demands without excessively increasing left ventricular filling pressures. It is characterized by specific symptoms, such as dyspnea and fatigue, and signs, such as fluid retention. As used herein, "chronic heart failure" or "congestive heart failure" or "CHF" refer, interchangeably, to an ongoing or persistent forms of heart failure. Common risk factors for CHF include old age, diabetes, high blood pressure and being overweight. CHF is broadly classified according to the systolic function of the left ventricle as HF with reduced or preserved ejection fraction (HFrEF and HFpEF). The term "heart failure" does not mean that the heart has stopped or is failing completely, but that it is weaker than is normal in a healthy person. In some cases, the condition is mild, causing symptoms that are noticeable when exercising, in others, the condition is more severe, causing symptoms that are, in some cases, life-threatening, even while at rest. The most common symptoms of chronic heart failure include shortness of breath, tiredness, swelling of the legs and ankles, chest pain and a cough. In some embodiments, the methods of the disclosure decrease, prevent, or ameliorate one or more symptoms of CHF (e.g., HFrEF) in a subject suffering from or at risk for CHF (e.g., HFrEF). In some embodiments, the disclosure provides methods of treating CHF and conditions that sometimes lead to CHF.

As used herein "acute heart failure" or "decompensated heart failure" refer, interchangeably, to a syndrome of the worsening of signs and symptoms reflecting an inability of the heart to pump blood at a rate commensurate to the needs of the body at normal filling pressure. AHF typically develops gradually over the course of days to weeks and then decompensates requiring urgent or emergent therapy due to the severity of these signs or symptoms. In some cases, AHF is the result of a primary disturbance in the systolic or diastolic function of the heart or of abnormal venous or arterial vasoconstriction, but generally represents an interaction of multiple factors, including volume overload. The majority of patients with AHF have decompensation of chronic heart failure (CHF) and consequently much of the discussion of the pathophysiology, presentation, and diagnosis of CHF is directly relevant to an understanding of AHF. In other cases, AHF results from an insult to the heart or an event that impairs heart function, such as an acute myocardial infarction, severe hypertension, damage to a heart valve, abnormal heart rhythms, inflammation or infection of the heart, toxins and medications. In some embodiments, the methods of the disclosure decrease, prevent, or ameliorate one or more symptoms of AHF in a subject suffering from or at risk for AHF. In some embodiments, the disclosure provides methods of treating AHF and conditions that sometimes lead to AHF. In some cases, AHF is the result of ischemia associated with myocardial infarction.

As used herein, the terms "subject" or "individual" refers to any animal, such as a domesticated animal, a zoo animal, or a human. In some cases, the "subject" or "individual" is a mammal like a dog, cat, horse, livestock, a zoo animal, or a human. Alternatively or in combination, the subject or individual is a domesticated animal such as a bird, a pet, or a farm animal. Specific examples of "subjects" and "individuals" include, but are not limited to, individuals with a cardiac disease or disorder, and individuals with cardiac disorder-related characteristics or symptoms, such as arrhythmogenic right ventricular cardiomyopathy (ARVC) or arrhythmogenic cardiomyopathy (ACM).

The practice of the present disclosure will employ, unless otherwise indicated, conventional techniques of tissue culture, immunology, molecular biology, cell biology and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; IRL Press (1986) Immobilized Cells and Enzymes; Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3rd edition (2002) Cold Spring Harbor Laboratory Press; Sohail (2004) Gene Silencing by RNA Interference: Technology and Application (CRC Press); Sell (2013) Stem Cells Handbook.

Unless the context indicates otherwise, it is specifically intended that the various features of the disclosure described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth. It also is to be understood, although not always explicitly stated, that the reagents described herein are merely exemplary and that equivalents of such are known in the art.

It must be noted that as used herein and in the appended claims, the singular forms "a", "an", and "the" include plural referents unless the context clearly dictates otherwise. Thus, for example, reference to "a cardiomyocyte" includes a plurality of cardiomyocytes.

Also as used herein, "and/or" refers to and encompasses any and all possible combinations of one or more of the associated listed items, as well as the lack of combinations when interpreted in the alternative ("or").

"Administration," "administering" and the like, when used in connection with a gene therapy vector or composition thereof as provided herein refer both to direct administration, which, in some cases includes administration to non-cardiomyocytes in vitro, administration to non-cardiomyocytes in vivo, administration to a subject by a medical professional or by self-administration by the subject and/or to indirect administration, which, in some cases, is the act of prescribing a composition comprising a gene therapy vector provided herein. When used herein in reference to a cell, it refers to introducing a composition to the cell. Typically, an effective amount is administered, which amount is often to be determined by one of skill in the art. Any suitable method of administration is contemplated to be used. In some cases, a gene therapy vector is administered to the cells by, for example, by addition of the gene therapy vector to the cell culture media or injection in vivo to the site of cardiac injury. In some cases, administration to a subject is achieved by, for example, intravascular injection, intramyocardial delivery, and the like.

As used herein the term "cardiac cell" refers to any cell present in the heart that provides a cardiac function, such as heart contraction or blood supply, or otherwise serves to maintain the structure of the heart. Cardiac cells as used herein encompass cells that exist in the epicardium, myocardium or endocardium of the heart. Cardiac cells also include, for example, cardiac muscle cells or cardiomyocytes, and cells of the cardiac vasculatures, such as cells of a coronary artery or vein. Other non-limiting examples of cardiac cells include epithelial cells, endothelial cells, fibroblasts, cardiac stem or progenitor cells, cardiac conducting cells and cardiac pacemaking cells that constitute the cardiac muscle, blood vessels and cardiac cell supporting structure. In some cases, cardiac cells are derived from stem cells, including, for example, embryonic stem cells or induced pluripotent stem cells.

The term "cardiomyocyte" or "cardiomyocytes" as used herein refers to sarcomere-containing striated muscle cells, naturally found in the mammalian heart, as opposed to skeletal muscle cells. Cardiomyocytes are characterized by the expression of specialized molecules e.g., proteins like myosin heavy chain, myosin light chain, cardiac α-actinin. The term "cardiomyocyte" as used herein is an umbrella term comprising any cardiomyocyte subpopulation or cardiomyocyte subtype, e.g., atrial, ventricular and pacemaker cardiomyocytes.

The term "culture" or "cell culture" means the maintenance of cells in an artificial, in vitro environment. A "cell culture system" is used herein to refer to culture conditions in which a population of cells are grown as monolayers or in suspension. "Culture medium" is used herein to refer to a nutrient solution for the culturing, growth, or proliferation of cells. Culture medium is characterized, in some cases, by functional properties such as, but not limited to, the ability to maintain cells in a particular state (e.g., a pluripotent state, a quiescent state, etc.), or to mature cells, such as, in some embodiments, to promote the differentiation of progenitor cells into cells of a particular lineage (e.g., a cardiomyocyte).

As used herein, the term "expression" or "express" refers to the process by which nucleic acids or polynucleotides are transcribed into mRNA and/or the process by which the transcribed mRNA is subsequently being translated into peptides, polypeptides, or proteins. If the polynucleotide or nucleic acid is derived from genomic DNA, in some cases, expression includes splicing of the mRNA in a eukaryotic cell. In some cases, the expression level of a gene is determined by measuring the amount of mRNA or protein in a cell or tissue sample.

As used herein, an "expression cassette" is a DNA polynucleotide comprising one or more polynucleotides or nucleic acids encoding protein(s) or nucleic acid(s) that is configured to express the polynucleotide in a host cell. Typically, expression of the polynucleotide(s) is placed under the control of certain regulatory elements, including constitutive or inducible promoters, tissue-specific regulatory elements, and enhancers. Such polynucleotides are said to be "operably linked to" or "operatively linked to" the regulatory elements (e.g., a promoter).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Treatment," "treating," and "treat" are defined as acting upon a disease, disorder, or condition with an agent to reduce or ameliorate harmful or any other undesired effects of the disease, disorder, condition and/or their symptoms.

As used herein, the term "effective amount" and the like refers to an amount that is sufficient to induce a desired physiologic outcome (e.g., treatment of a disease). An effective amount is sometimes administered in one or more administrations, applications or dosages. Such delivery is dependent on a number of variables including the time period which the individual dosage unit is to be used, the bioavailability of the composition, the route of administration, etc. It is understood, however, that specific amounts of the compositions (e.g., gene therapy vectors) for any particular subject depends upon a variety of factors including the activity of the specific agent employed, the age, body weight, general health, sex, and diet of the subject, the time of administration, the rate of excretion, the composition combination, severity of the particular disease being treated and form of administration.

As used herein, the term "equivalents thereof" in reference to a polypeptide or nucleic acid sequence refers to a polypeptide or nucleic acid that differs from a reference polypeptide or nucleic acid sequence, but retains essential properties (e.g., biological activity). A typical variant of a polynucleotide differs in nucleotide sequence from another, reference polynucleotide. Changes in the nucleotide sequence of the variant, in some cases, alters the amino acid sequence of a polypeptide encoded by the reference polynucleotide. In some cases, nucleotide changes result in amino acid substitutions, deletions, additions, fusions and truncations in the polypeptide encoded by the reference sequence. Generally, differences are limited so that the sequences of the reference polypeptide and the variant are closely similar overall and, in many regions, identical.

As used herein, the term "nucleic acid" and "polynucleotide" are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers. As used herein, the word "polynucleotide" or "nucleic acid" preceded by a gene name (for example, "PKP2 nucleic acid") refers to a polynucleotide sequence encoding the corresponding protein (for example, a "PKP2 protein").

The terms "polypeptide," "peptide," and "protein," are used interchangeably herein and refer to a polymeric form of amino acids of any length, which sometimes include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues, immunologically tagged proteins, and the like. As used herein, the word "protein" preceded by a gene name (for example, "PKP2 protein") refers to either the native protein or a functional variant thereof. A "native protein" is a protein encoded by a genomic copy of a gene of an organism, preferably the organism for which the vector is intended (e.g., a human, a rodent, a primate, or an animal of veterinary interest), in any of the gene's functional isoforms or functional allelic variations.

As used herein, a "functional variant" or "variant" of a protein is a variant with any number of amino acid substitutions, insertions, truncations, or internal deletions that retains the functional attributes of the protein, including, e.g., the protein's ability to induce, in combination with other factors, organization of desmosomes. In some cases, functional variants are identified computationally, such as variants having only conservative substitutions, or experimentally using in vitro or in vivo assays.

As used herein, a "codon variant" of a polynucleotide sequence is polynucleotide sequence that encodes the same protein as a reference polynucleotide sequence having one or more synonymous codon substitutions. Selection of synonymous codons is within the skill of those in the art, the coding as the genetic code being known. In some cases, codon optimization is performed using a variety of computational tools (such the GENSMART™ Codon Optimization tool available at www.genscript.com). Generally codon optimization is used to increase the expression of protein in a heterologous system, for instance when a human coding sequence is expressed in a bacterial system. The term "codon variant" is intended to encompass both sequences that are optimized in this manner and sequences that are optimized for other purposes, such as removal of CpG islands and/or cryptic start sites.

The term "vector" refers to a macromolecule or complex of molecules comprising a polynucleotide or protein to be delivered to a host cell, either in vitro or in vivo. A vector is sometimes a modified RNA, a lipid nanoparticle (encapsulating either DNA or RNA), a transposon, an adeno-associated virus (AAV) vector, an adenovirus, a retrovirus, an integrating lentiviral vector (LVV), or a non-integrating LVV. Thus, as used herein "vectors" include naked polynucleotides used for transformation (e.g. plasmids) as well as any other composition used to deliver a polynucleotide to a cell, included vectors capable of transducing cells and vectors useful for transfection of cells.

As used herein, the term "viral vector" refers either to a nucleic acid molecule that includes virus-derived nucleic acid elements that typically facilitate transfer of the nucleic acid molecule or integration into the genome of a cell or to a viral particle that mediates nucleic acid transfer. Viral particles will typically include various viral components and sometimes also cell components in addition to nucleic acid(s).

The term "genetic modification" refers to a permanent or transient genetic change induced in a cell following introduction of new nucleic acid (i.e., nucleic acid exogenous to the cell). Genetic change is often accomplished by incorporation of the new nucleic acid into the genome of the cardiac cell, or by transient or stable maintenance of the new nucleic acid as an extrachromosomal element. Where the cell is a eukaryotic cell, a permanent genetic change is often achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

FIG. 1 shows cardiac desmosomes tie cells together (Brodehl et al., 2018; Moncayo-Arlandi and Brugada, 2017). The red line in the top panel is depicted as desmin, the intermediate filaments, which forms network to stabilize sarcomeres and other organelles. An EM picture of desmosome is shown in the left corner.

FIG. 2 shows a summary of ARVC disease indications and possible disease mechanisms.

Figure 3A:
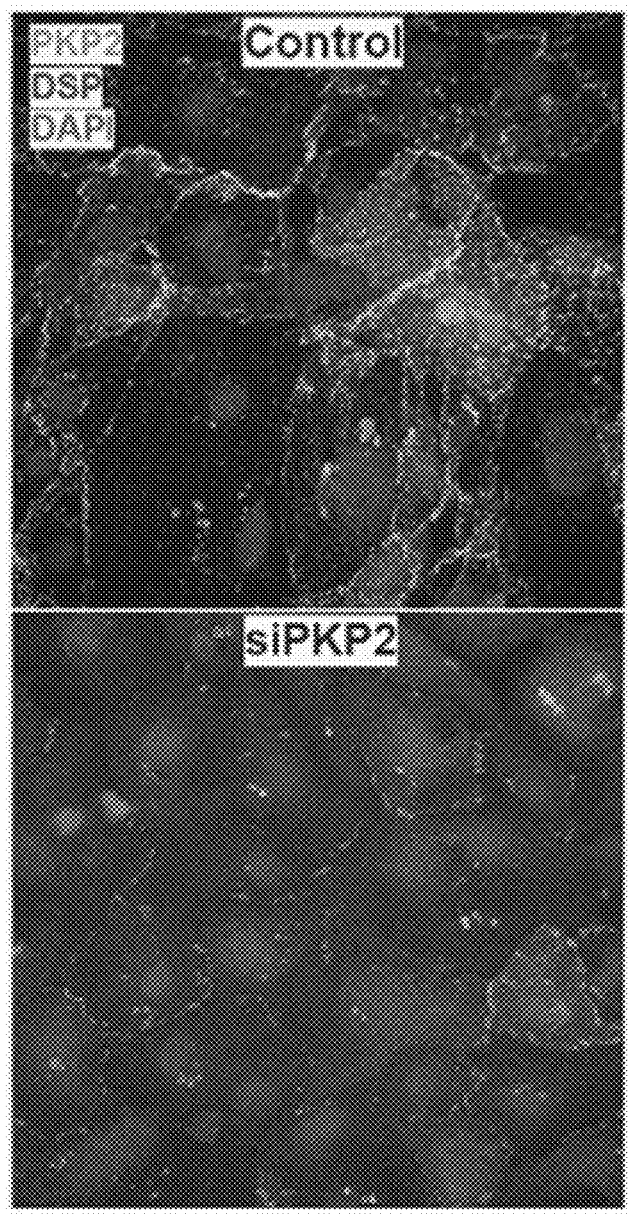
FIGS. 3A-3C show the results of acute silencing of PKP2 in iPSCM at day 8.
Figure 3B:
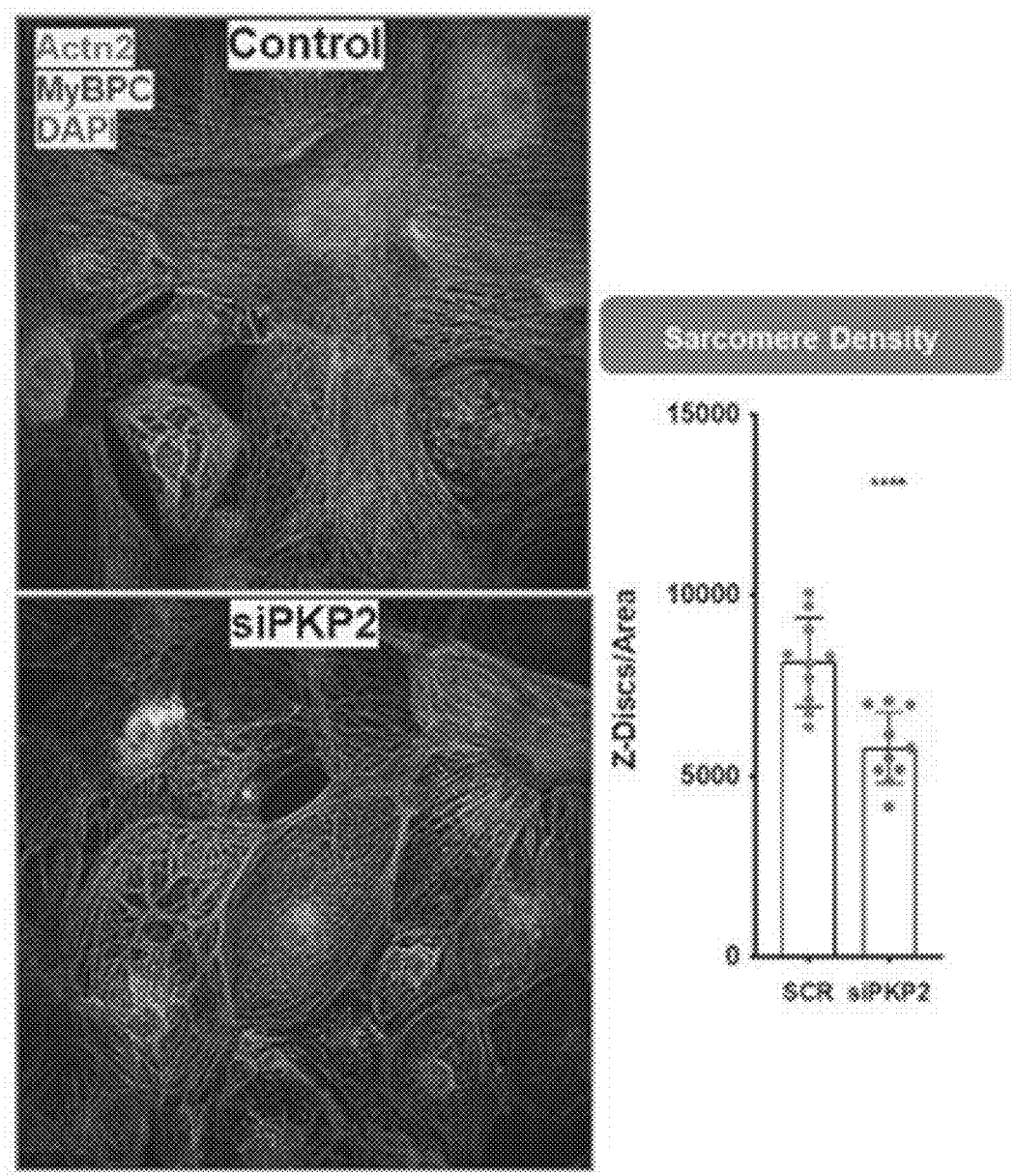
Figure 3C:
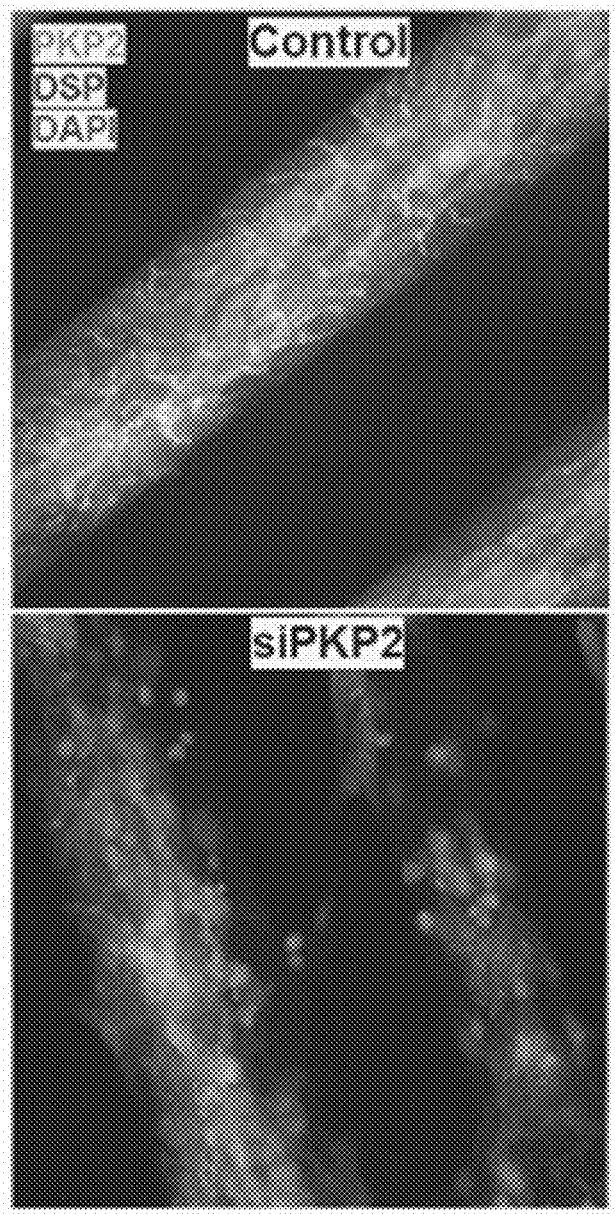

FIGS. 3A-3C show results of acute silencing of PKP2 in iPSCM at day 8 showed significant cellular phenotypes. In FIG. 3A and FIG. 3C PKP2 in green, DSP in red, and nuclei in blue. In FIG. 3B sarcomeric protein Actn2 in green and MyBPC in magenta.

Figure 4:
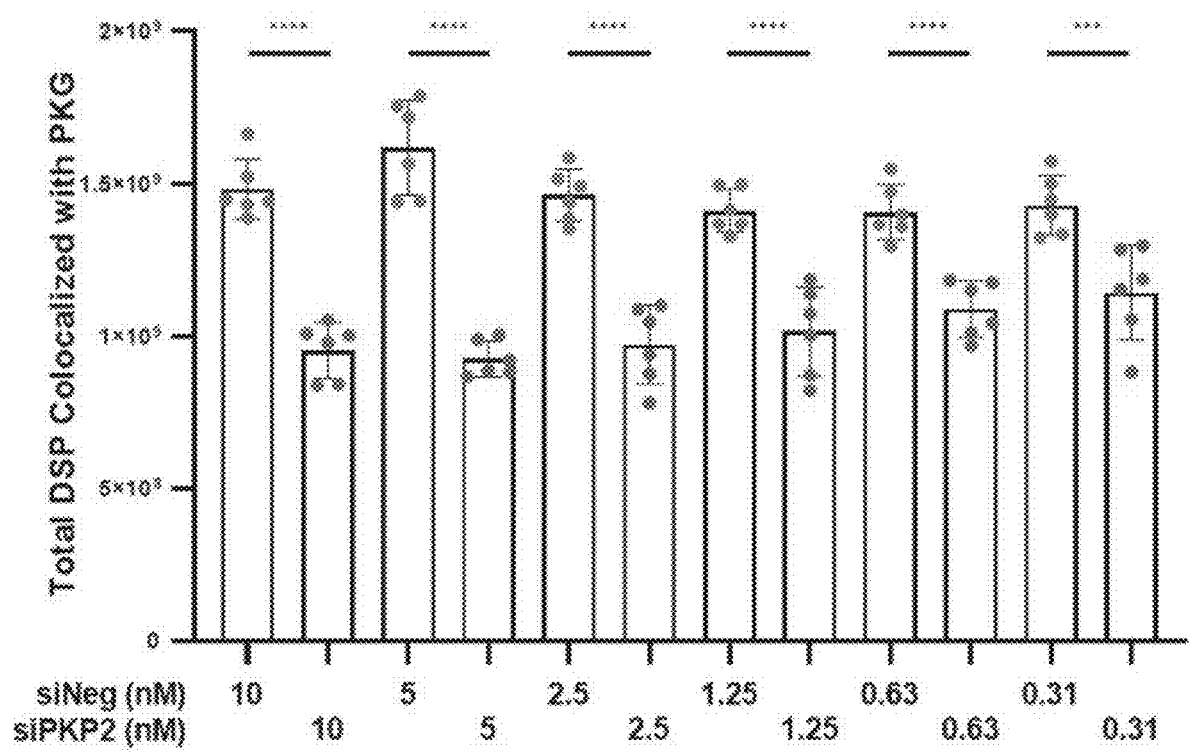
FIG. 4 shows a quantitative analysis of DSP membrane localization as determined by colocalization with PKG.

FIG. 4 shows a quantitative measurement of DSP membrane localization is estimated by its co-localization with PKG, another desmosomal protein, in response to a range of dosage of siPKP2 at day 8 of silencing.

Figure 5:
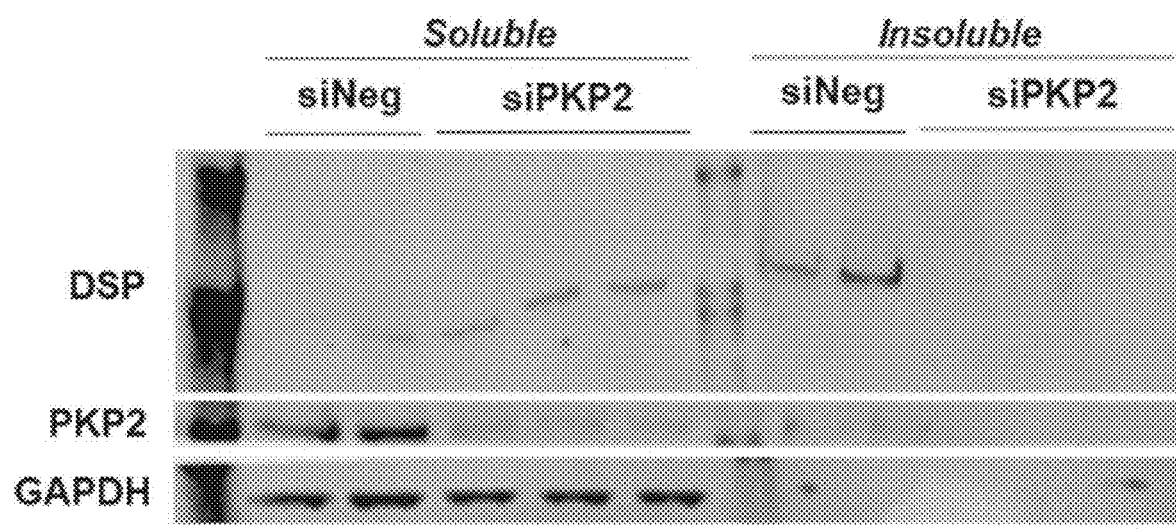
FIG. 5 shows an immunoblot which illustrates a reduced total amount of DSP protein, detected mainly in the insoluble fraction, in cells where PKP2 is silenced.

FIG. 5 illustrates an immunoblot showing that silencing PKP2 leads to a reduced total amount of DSP protein from the desmosomes, detected mainly in the insoluble fraction, in cells where PKP2 is silenced as compared to the silencing control, siNeg.

Figure 6A:
FIGS. 6A-6B show results of PKP2 transduction by AAV.
Figure 6B:
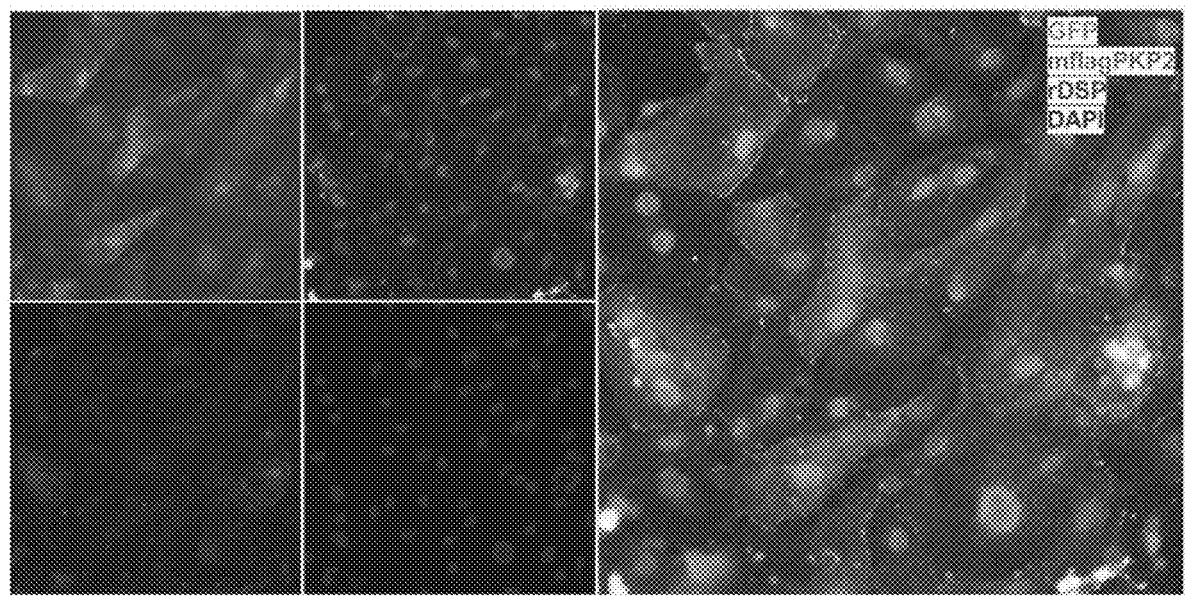
Figure 6C:
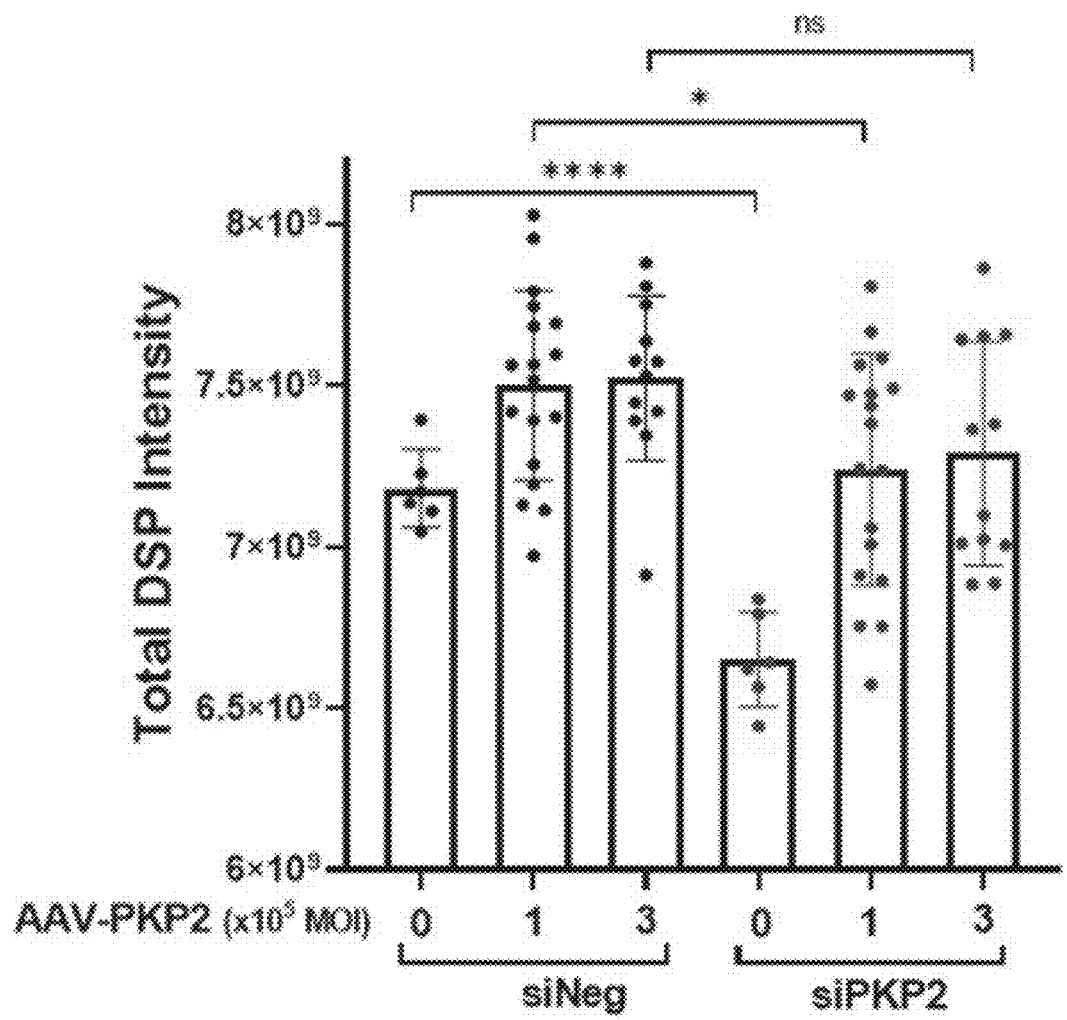
FIG. 6C shows a quantification of total DSP intensity post PKP2 silencing and AAV-PKP2 transgene rescue.

FIG. 6A shows a vector map for AAV-PKP2 gene therapy. FIG. 6B shows restoration of DSP membrane location by expressing PKP2 transgene using AAV-mediated gene delivery to iPSCM at day 10 of PKP2 silencing and at day 8 of AAV transduction. GFP is co-expressed with the flag-tagged PKP2. Flag tag is in cyan, DSP in red, and nuclei in blue. FIG. 6C shows AAV-PKP2 transgene restoration of expression of total DSP post PKP2 silencing in iPSC cardiomyocytes. A quantification of total DSP intensity in immunofluorescent signal is showed post PKP2 silencing in the absence or the presence of AAV-PKP2 transgene rescue.

Figure 7A:
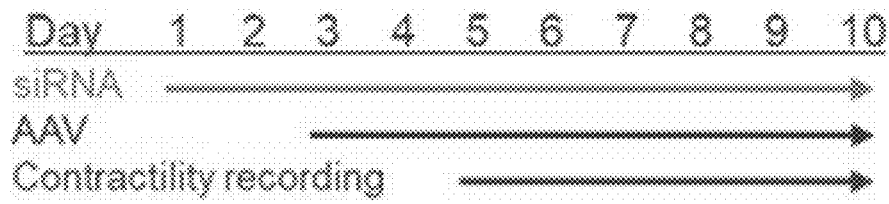
FIGS. 7A-7B show results of PKP2 transduction by AAV on contraction velocity.
Figure 7B:
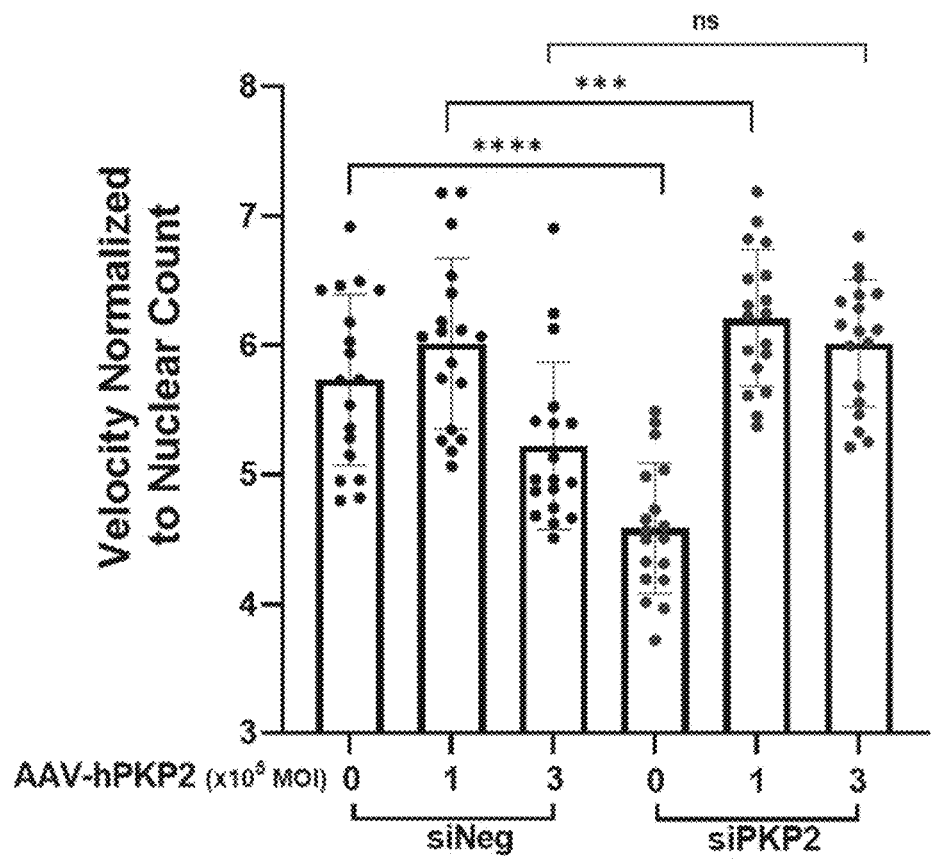

FIG. 7A-7B show AAV PKP2 transgene expression rescued contraction velocity of iPSCM post PKP2 silencing. FIG. 7A shows PKP2 silencing, AAV transduction, and contractility recording schedule. FIG. 7B shows AAV-PKP2 transgene partially restores contraction velocity post PKP2 silencing. Contraction velocity, normalized to the nuclear count, is shown post PKP2 silencing in the absence or the presence of AAV-PKP2 transgene rescue.

Figure 8:
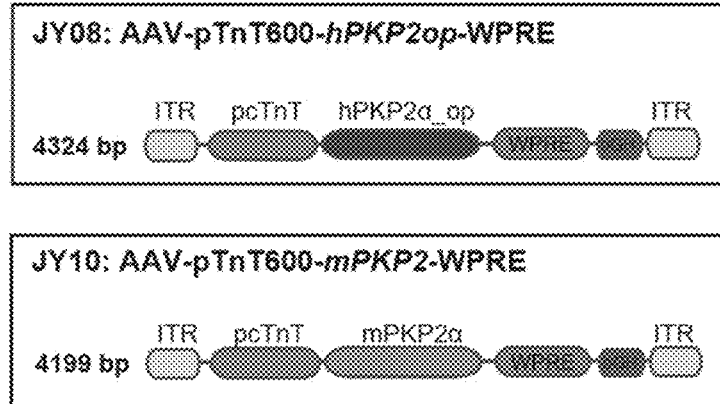
FIG. 8 shows a second generation schematic of an AAV expression cassette of human and mouse PKP2α. The left panel shows all of the elements in the expression cassette. The right panel shows the arrangement of elements in the expression cassettes.

FIG. 8 shows a schematic representation of the second generation AAV expression cassette of human and mouse PKP2α. The left table shows all elements in the expression cassette. The right panel shows the mouse and human expression cassettes.

Figure 9A:
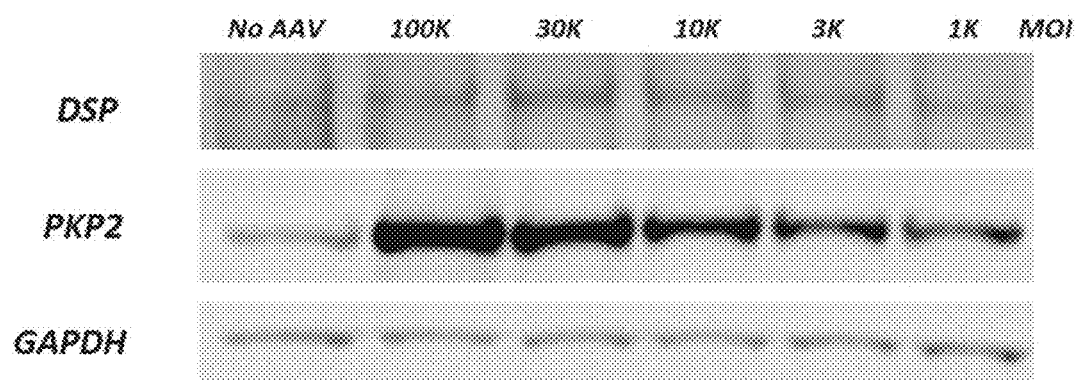
FIG. 9A and FIG. 9B show results of the second generation AAV-hPKP2α rescue of contraction velocity post PKP2 silencing in iPSC cardiomyocytes.
Figure 9A:
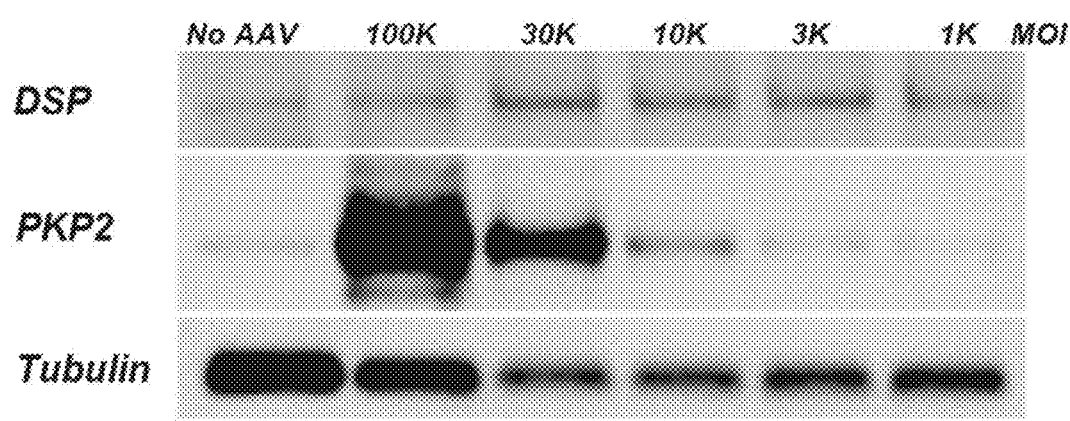
Figure 9B:
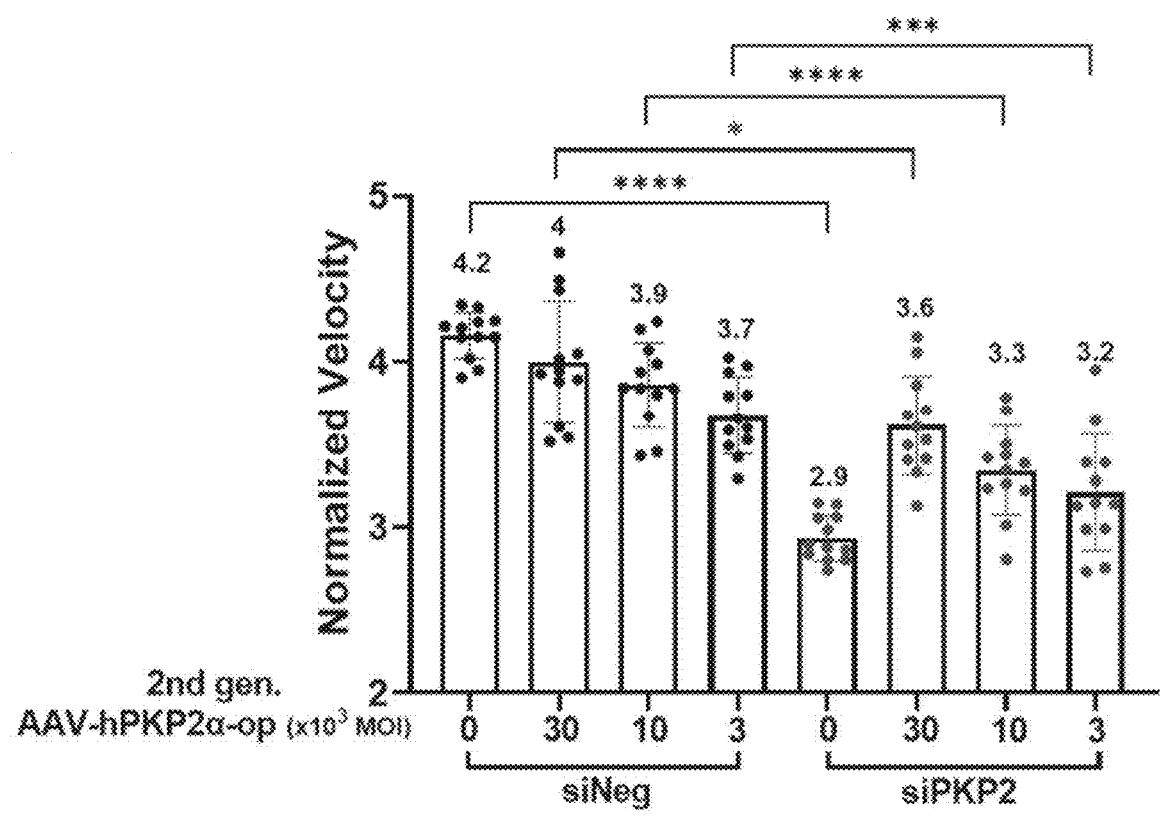

FIG. 9A-9B show preliminary results for the second generation AAV-hPKP2α partially rescues contraction velocity post PKP2 silencing in iPSC cardiomyocytes. FIG. 9A shows human PKP2a transgene was expressed in iPSC cardiomyocytes in a dose-dependent fashion. FIG. 9B shows human PKP2α transgene showed a partial rescue of contraction velocity post PKP2 silencing at 30K MOI.

Figure 10:
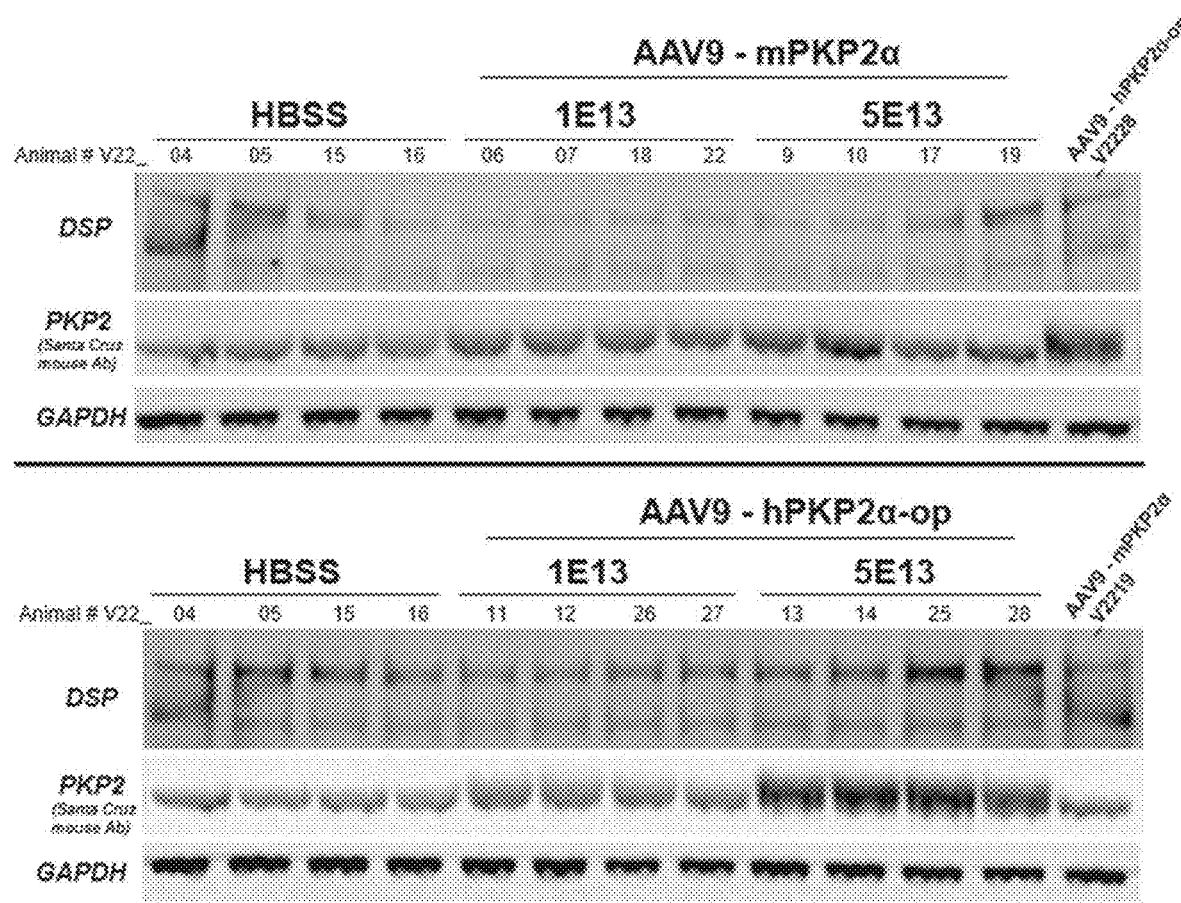
FIG. 10 shows expression of the second generation AAV-PKP2a in wildtype mice.

FIG. 10 shows expression analysis of second generation AAV9 human and mouse PKP2α in 12 week-old C57BJ6 animals. The upper panel shows expression of endogenous mouse PKP2α in HBSS control mice and expression of both endogenous and transduced mouse PKP2α at two AAV9 injected doses, 1E13 and 5E13, respectively. The lower panel shows corresponding expression analysis of transduced human PKP2α, a slightly larger homolog.

Figure 11A:
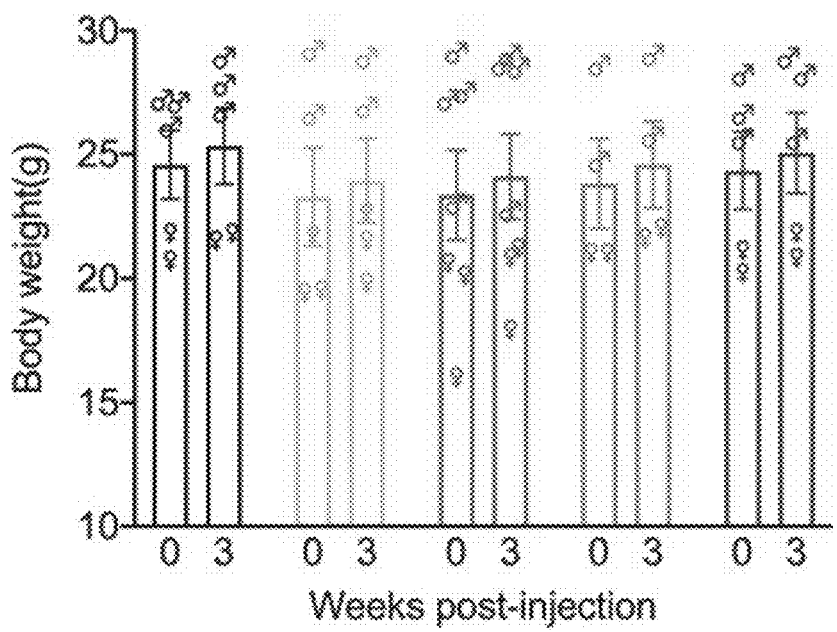
FIGS. 11A-11G show results of pilot expression safety studies of the second generation AAV9 human and mouse PKP2a in wildtype mice.
Figure 11B:
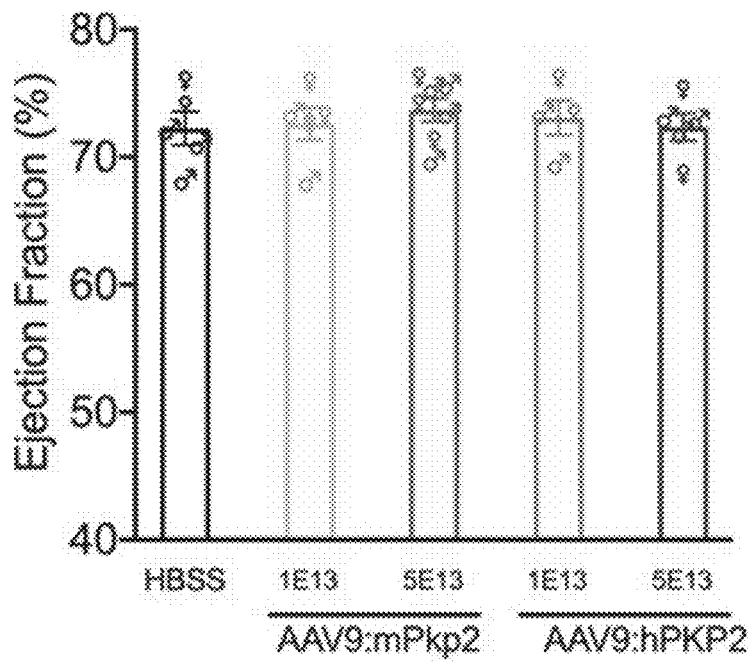
Figure 11C:
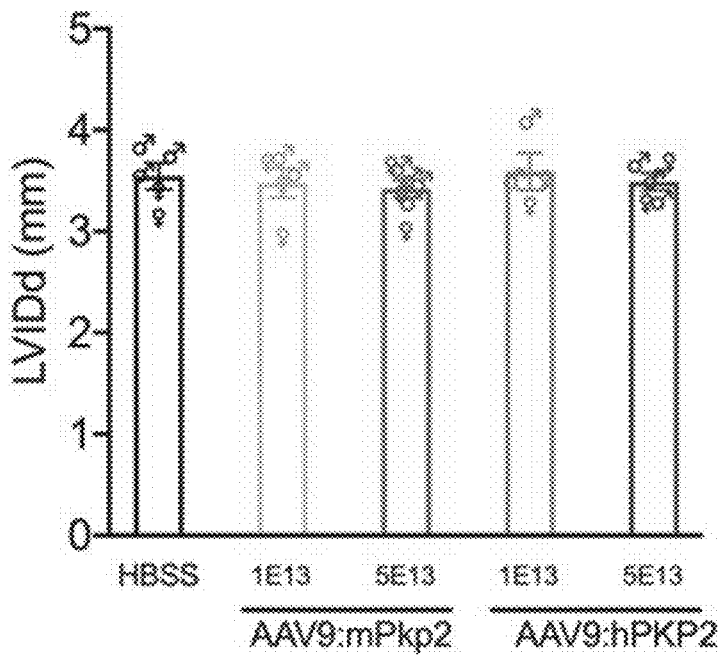
Figure 11D:
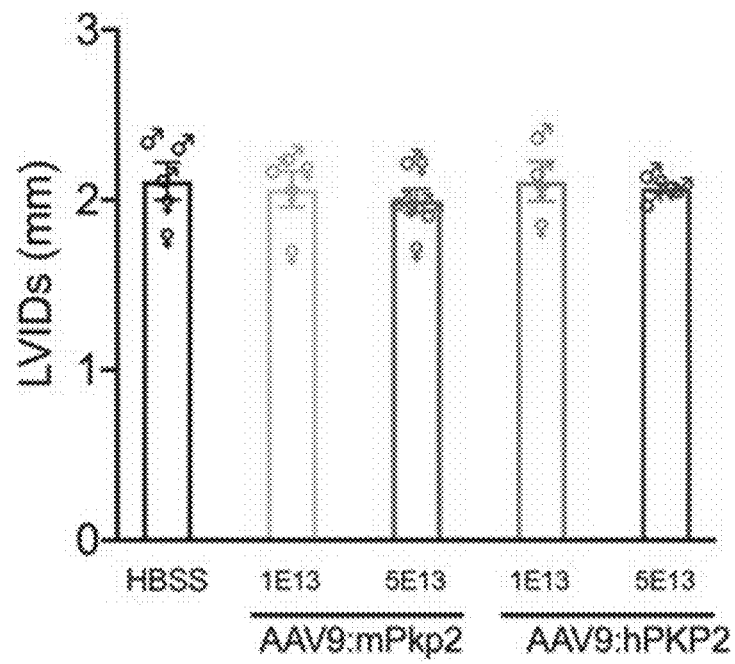
Figure 11E:
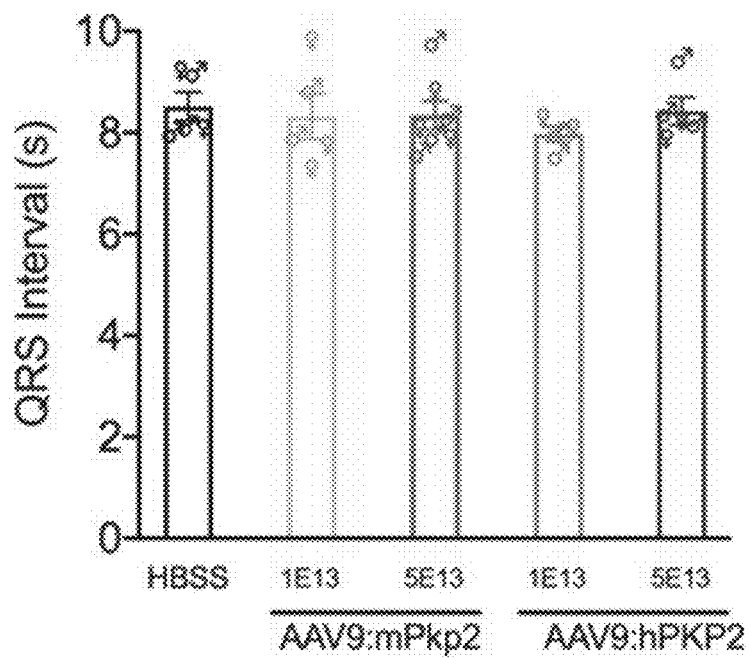
Figure 11F:
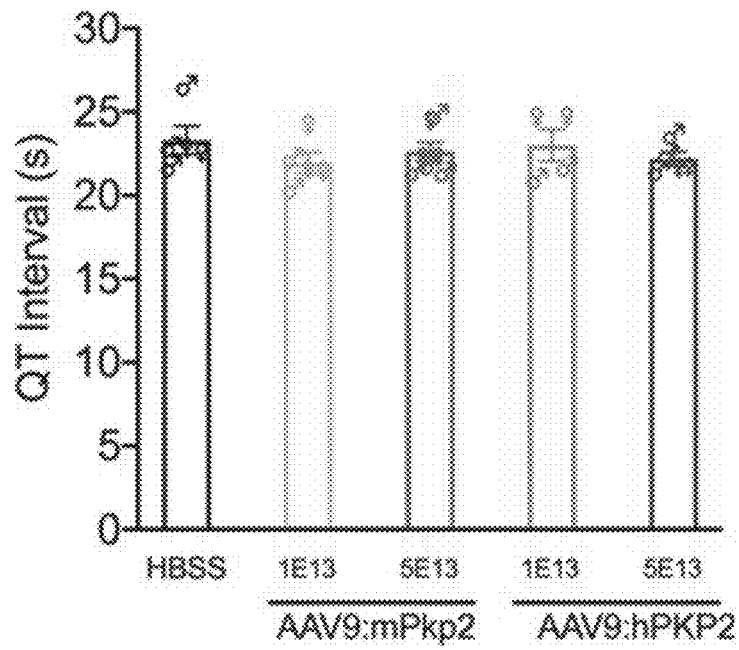
Figure 11G:
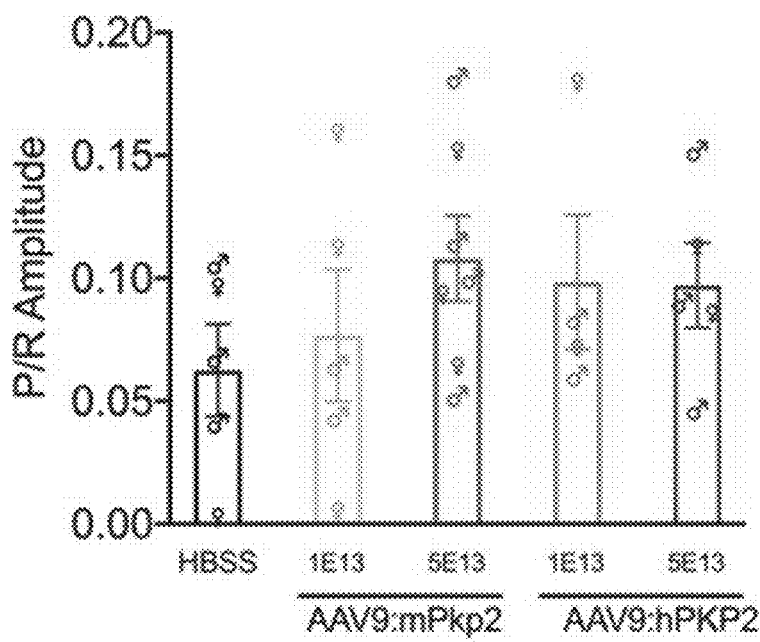

FIGS. 11A-G show pilot expression safety studies of second generation AAV9 human and mouse PKP2α in 12 week-old C57BL/6 animals. FIG. 11A shows body weight before AAV9 injection and body weight at 3 weeks post AAV9 injection. FIG. 11B shows heart function is measured by percentage of ejection fraction at 3 weeks post AAV9 injection of either mouse or human PKP2α. FIG. 11C and FIG. 11D show LV structure measured by both internal diameters end diastole and systole. FIGS. 11E-11G show electrophysiology activity measured by QRS (FIG. 11E), QT interval (FIG. 11F), and PIR amplitude (FIG. 11G).

Figure 12:
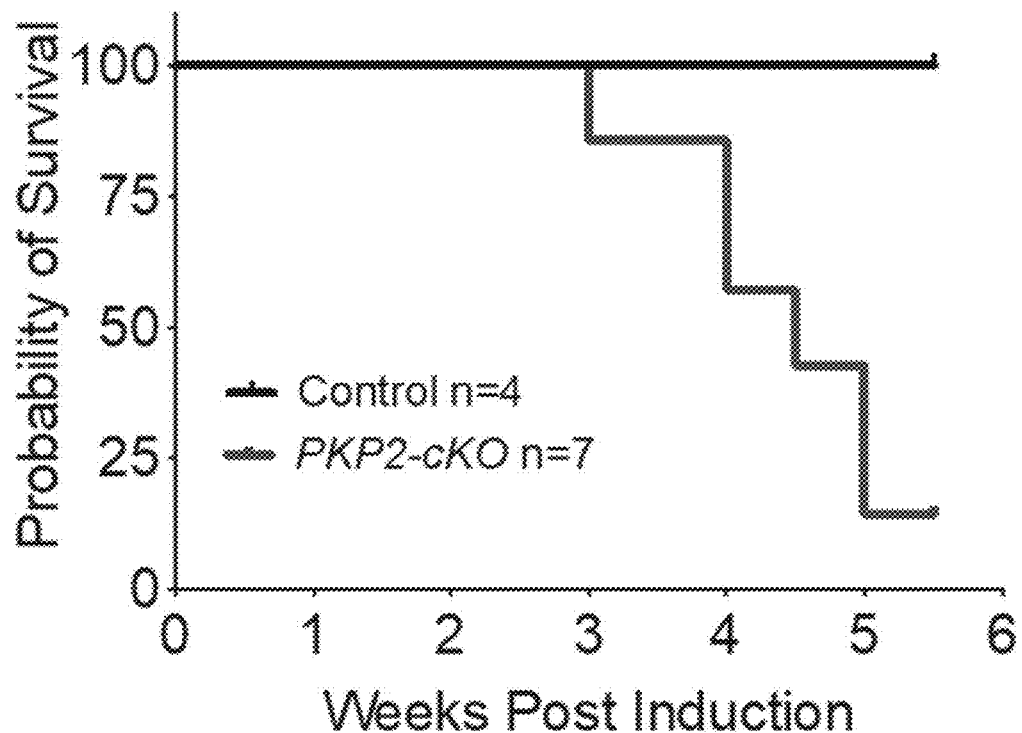
FIG. 12 shows a Kaplan-Meier survival curve of PKP2-cKO mice.

FIG. 12 shows a Kaplan-Meier survival curve of PKP2-cKO mice after tamoxifen induction. The curve shows that PKP2-cKO mice begin declining at three weeks post induction with only one mouse (of seven) surviving to six weeks.

Figure 13A:
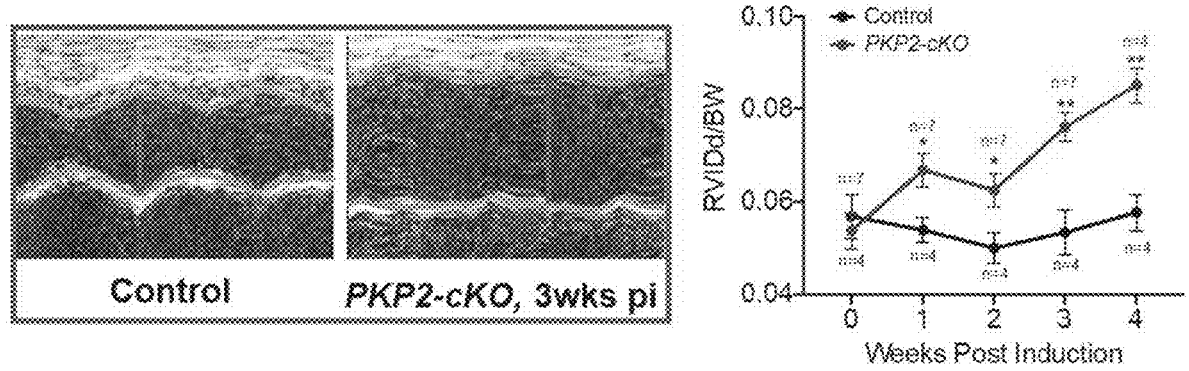
FIGS. 13A-13B show right ventricle (RV) dilated cardiomyopathy of PKP2-cKO mice.
Figure 13B:
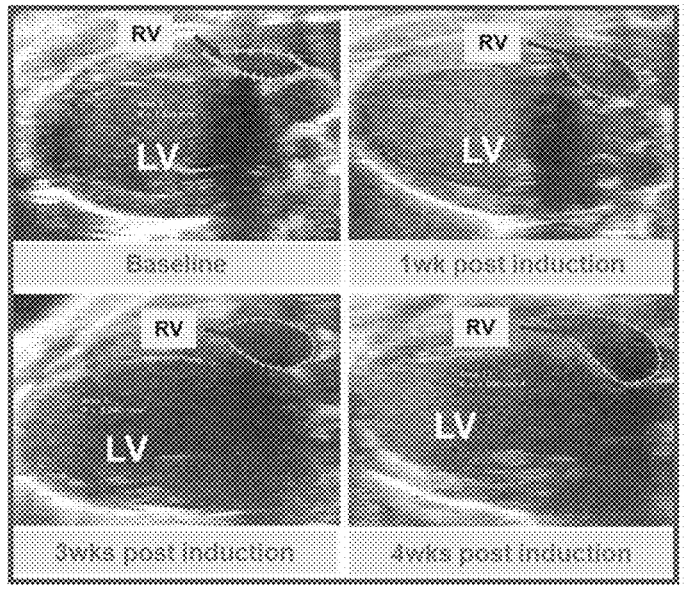
Figure 13B:
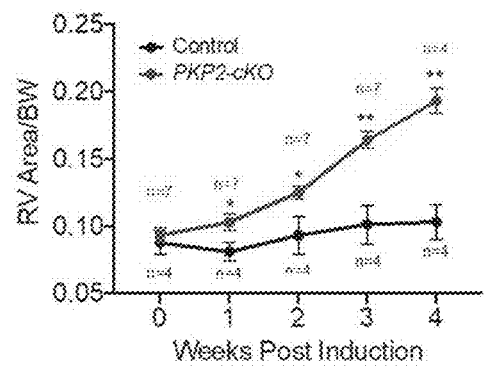

FIGS. 13A-13B show right ventricle (RV) dilated cardiomyopathy of PKP2-cKO mice. FIG. 13A (left panel) shows images that illustrate increased RV internal dimension at end-diastole (RVIDd) in PKP2-cKO mice at three weeks post tamoxifen induction compared with the control mice. FIG. 13A (right panel) shows a graph of RVIDd over time in PKP2-cKO mice compared with the control mice. FIG. 13B (left panel) shows images illustrating the increase in RV area in PKP2-cKO mice. The RV area is illustrated by a dotted line which is shown to increase in area starting at one week post induction, at three weeks, and at four weeks post induction. FIG. 13B (right panel) shows a graph of RV area over time in PKP2-cKO mice compared with control mice.

Figure 14A:
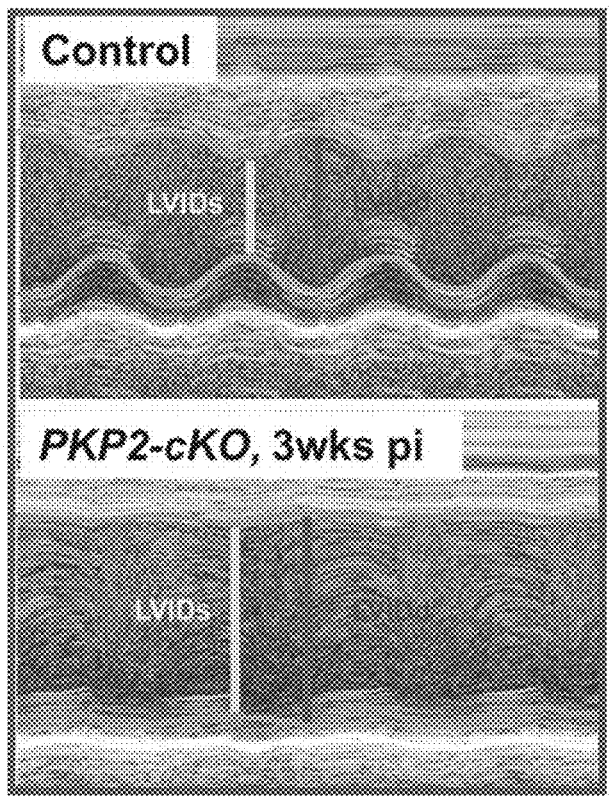
FIGS. 14A-14B show development of left ventricle (LV) dilated cardiomyopathy of PKP2-cKO mice compared with control.
Figure 14A:
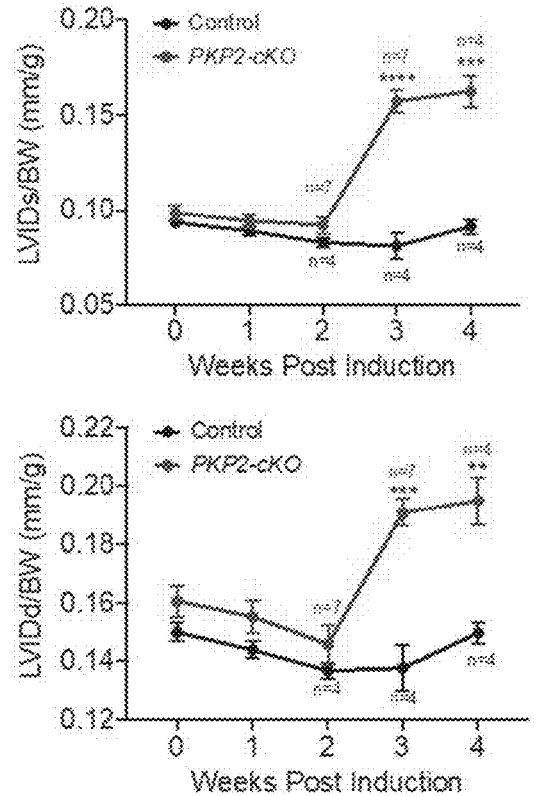
Figure 14B:
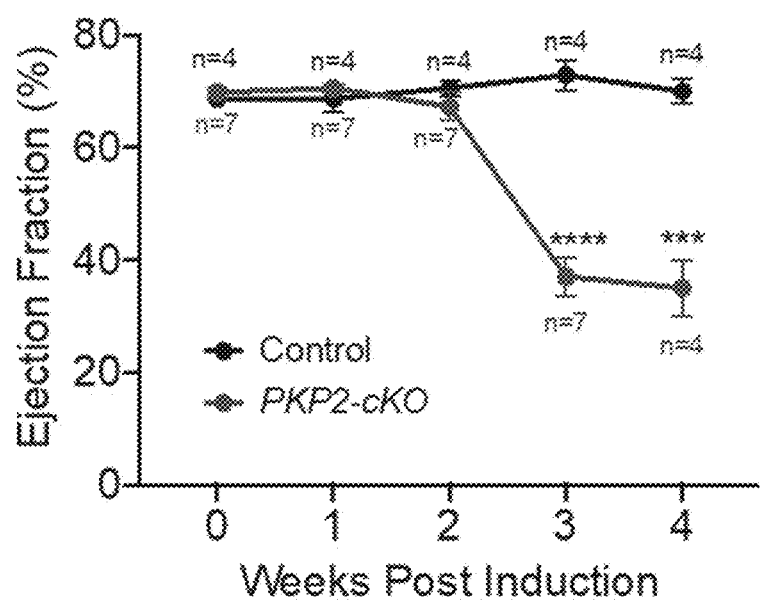

FIGS. 14A-14B show development of left ventricle (LV) dilated cardiomyopathy of PKP2-cKO mice compared with control. FIG. 14A (left panel) shows images of increased LV internal dimension at end-systole (LVIDs) and end-diastole (LVIDd) in PKP2-cKO mice compared with control. The LVIDs is shown as the yellow line to the left and the LVIDd is shown as the red line to the right. FIG. 14A (right panel) shows a graph which shows the increase in LVIDs and LVIDd in PKP2-cKO mice over time compared with control mice. FIG. 14B shows a graph of LV performance as measured by percent ejection fraction over time compared with control mice.

Figure 15:
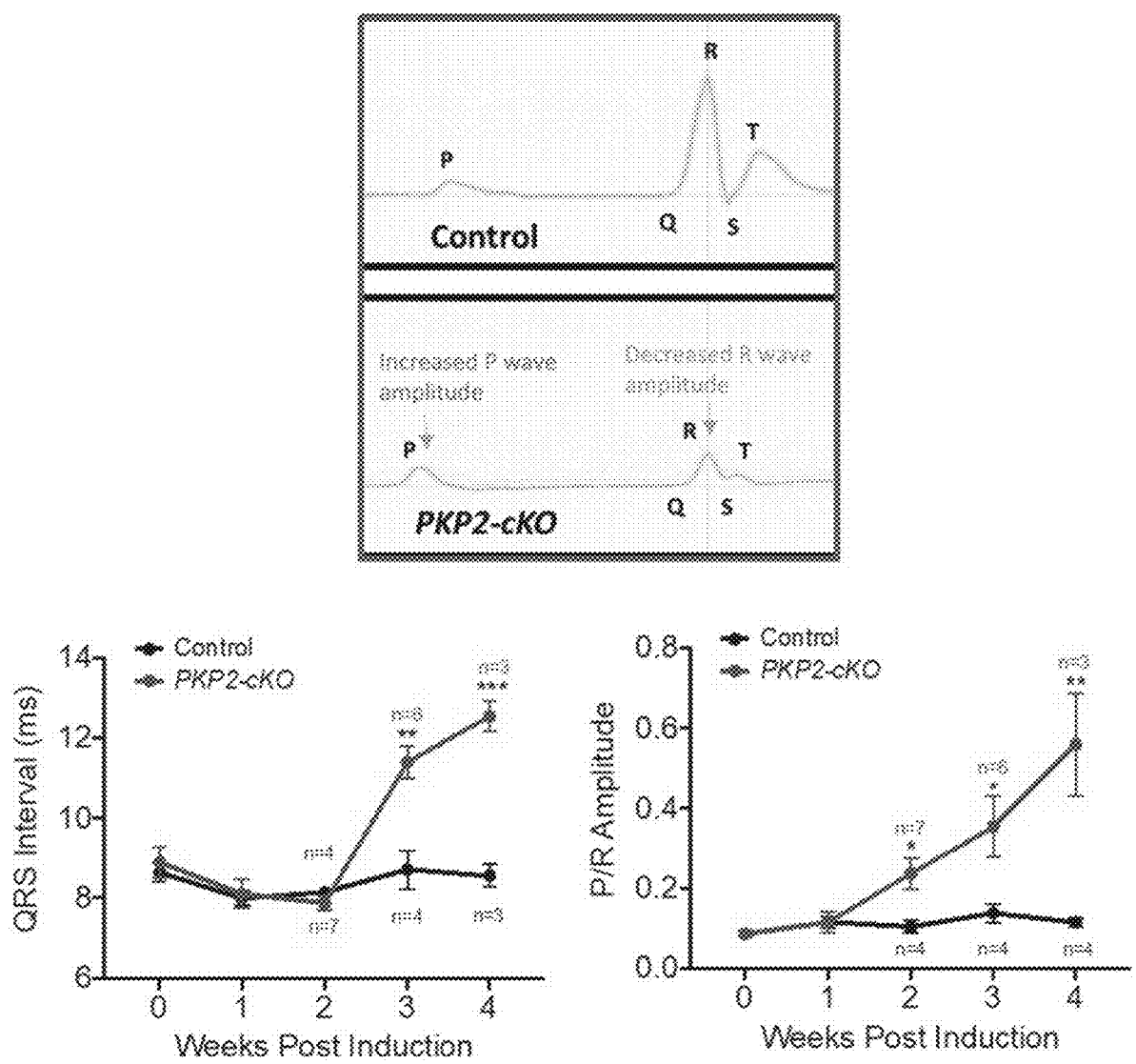
FIG. 15 shows development of severe electrophysiological phenotypes of PKP2-cKO mice compared with control, specifically prolonged QRS interval and increased P/R amplitude ratio in PKP2-cKO mice. The top panel shows exemplary electrocardiogram of control and PKP2-cKO mice. The bottom panel shows graphs of the increase in QRS interval and increase in P/R amplitude in PKP2-cKO mice compared with control.

FIG. 15 shows development of severe electrophysiological phenotypes of PKP2-cKO mice compared with control, specifically showing prolonged QRS interval and increased P/R amplitude ratio in PKP2-cKO mice. The top panel shows exemplary electrocardiogram of control (top) and PKP2-cKO mice (bottom). The increased P wave amplitude is shown in the PKP2-cKO mice compared with control. The electrocardiogram also shows a decreased R wave amplitude in PKP2-cKO mice compared with control mice. In addition, the QRS interval is prolonged in PKP2-cKO mice compared with control. The bottom panel shows graphs of the increase in QRS interval and increase in P/R amplitude in PKP2-cKO mice compared with control.

Figure 16A:
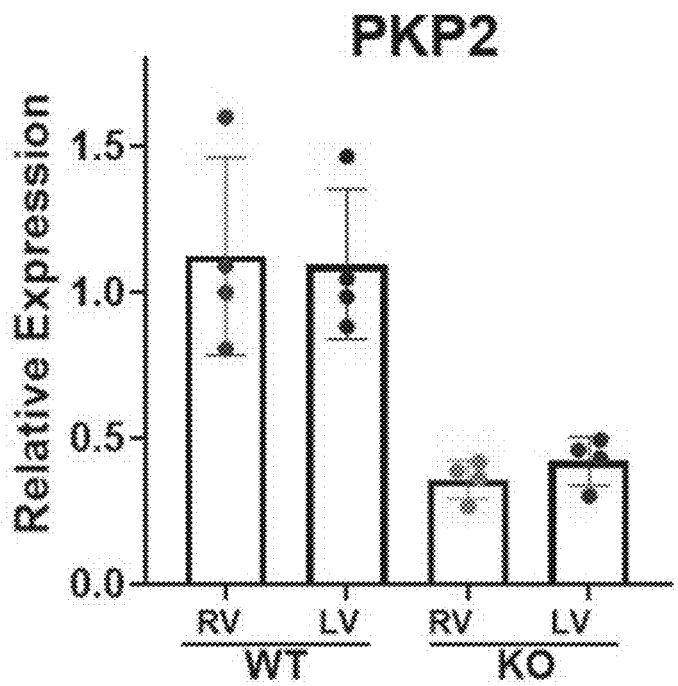
FIGS. 16A-16C show enhanced expression of fibrosis, tissue remodeling genes, and heart failure markers.
Figure 16A:
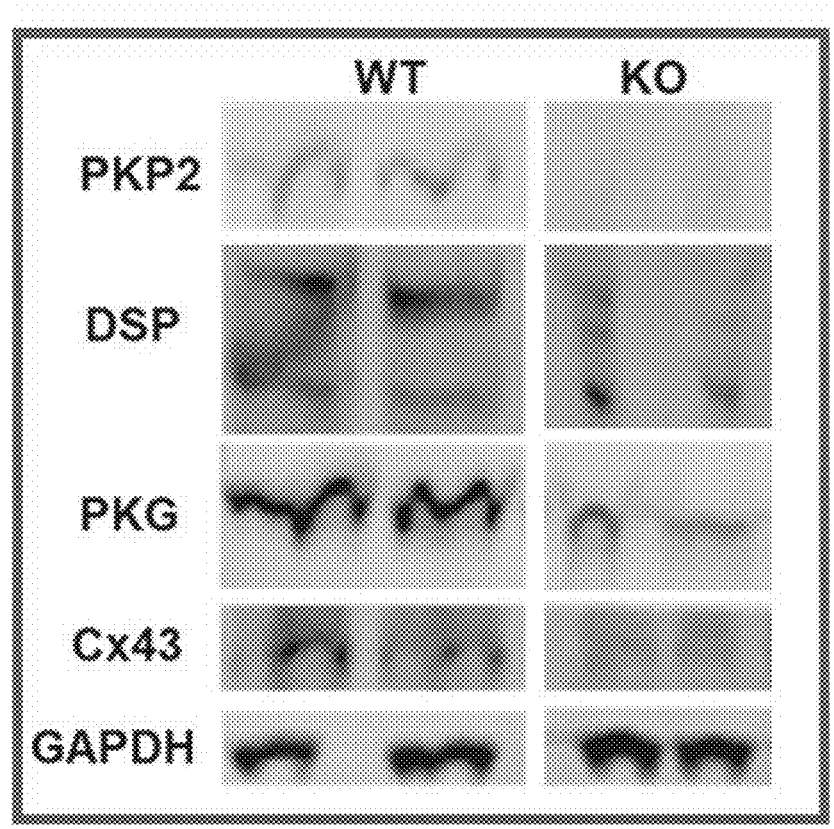
Figure 16B:
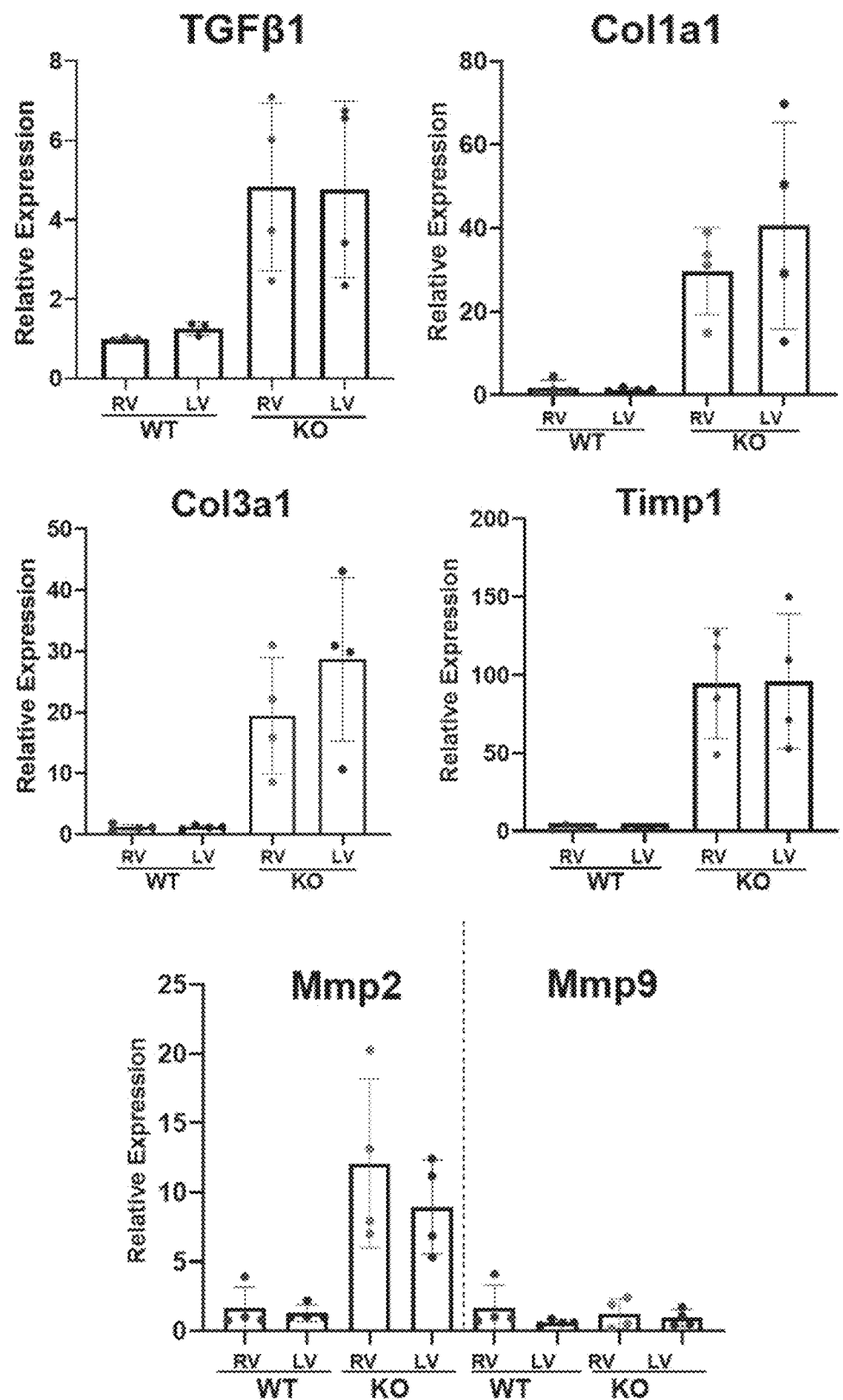
Figure 16C:
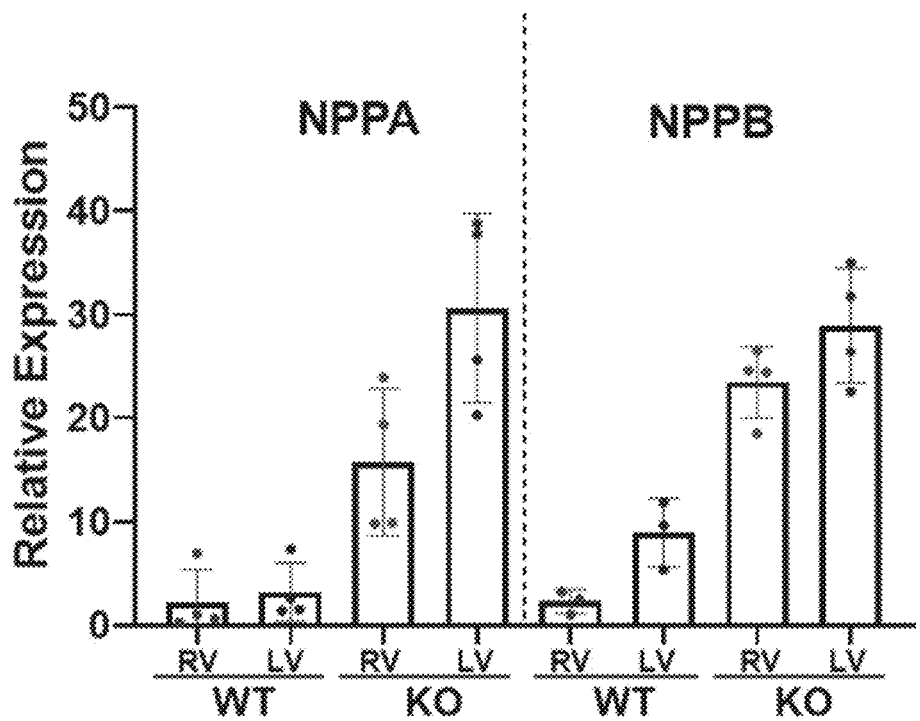

FIGS. 16A-16C show enhanced expression of fibrosis, tissue remodeling genes, and heart failure markers. FIG. 16A shows PKP2 RNA expression in RV and LV (top) and desmosome and Cx43 protein expression (bottom) of PKP2-cKO mice compared with control. The PKP2-cKO mice show about half the expression of PKP2 compared with control in both the LV and the RV. The bottom panel shows an immunoblot showing reduction in LV protein levels of PKP2, DSP, and PKG in desmosome and Cx43 in gap junction. FIG. 16B shows enhanced expression of fibrosis genes: TGFβ1, Col1a1, and Col3a1; and tissue remodeling genes: Timp1 and Mmp2 in PKP2-cKO mice compared with control. Here, expression of TGFβ1 and Timp1 is increased between control and PKP2-cKO mice in both RV and LV. Col1a1 and Col3a1 are also greatly increased in PKP2-cKO mice compared with control mice with slightly more elevated expression in LV compared to RV. Mmp2 is shown to be increased in PKP2-cKO mice compared with control mice with slightly more elevated expression in RV compared with LV. Mmp9 was not shown to have a difference in expression between control and PKP2-cKO mice. FIG. 16C shows enhanced expression of heart failure markers, NPPA and NPPB, in PKP2-cKO mice compared with control mice. In both NPPA and NPPB expression is slightly more elevated in LV compared with RV in PKP2-cKO mice.

Figure 17:
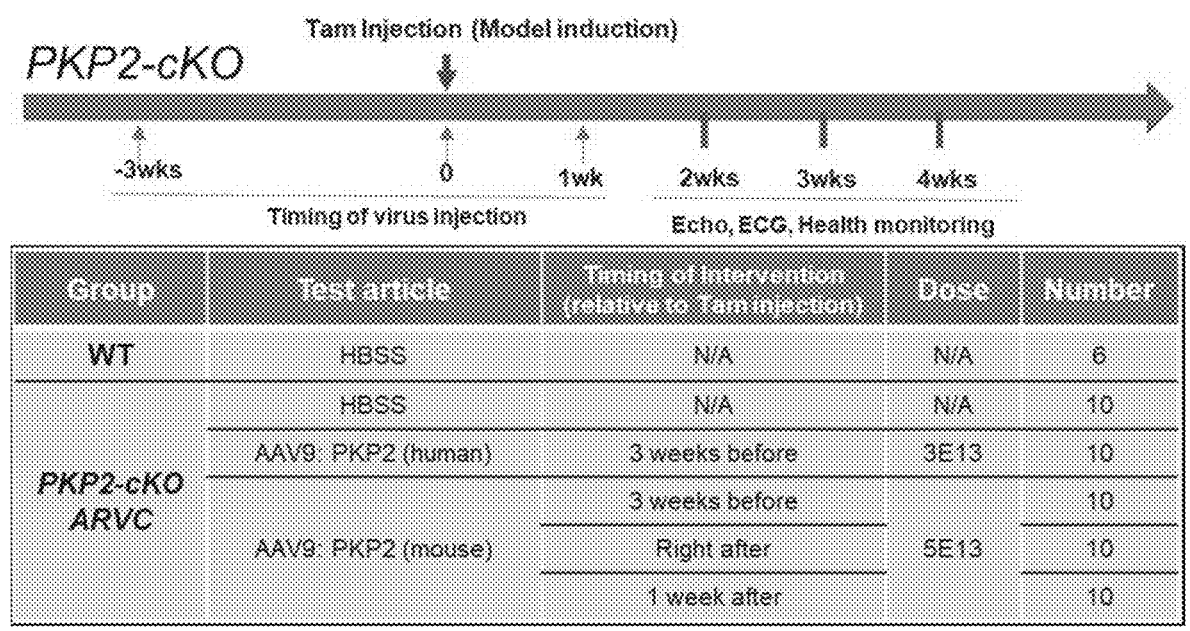
FIG. 17 shows the experimental design to evaluate PKP2 efficacy as gene therapy in the PKP2-cKO ARVC mouse model.

FIG. 17 shows the experimental design to evaluate PKP2 efficacy as gene therapy in the PKP2-cKO ARVC mouse model. A total of six individual treatment groups were included in the studies and all groups were tamoxifen treated for three consecutive days. They are: six WT mice with HBSS buffer treated; ten PKP2-cKO ARVC mice with HBSS buffer treated; ten PKP2-cKO ARVC mice with 3E13 vg/kg of AAV9:human PKP2 treated at 3 wks before tamoxifen induction; ten PKP2-cKO ARVC mice with 5E13 vg/kg of AAV9:mouse PKP2 treated at 3 wks before tamoxifen induction; ten PKP2-cKO ARVC mice with 5E13 vg/kg of AAV9:mouse PKP2 treated right after tamoxifen induction; and ten PKP2-cKO ARVC mice with 5E13 vg/kg of AAV9:mouse PKP2 treated at 1 wk after tamoxifen induction. Baseline readings of body weight, echocardiography, and EKG were collected before tamoxifen induction. All readings post tamoxifen induction were recorded weekly including echocardiography of B-mode, M-Mode (RV, LV), and structure (LV internal diameters) and 30-min ECG for quantifying arrythmias and evaluating electrophysiological parameters.

Figure 18A:
Figure 18A:
Figure 18B:
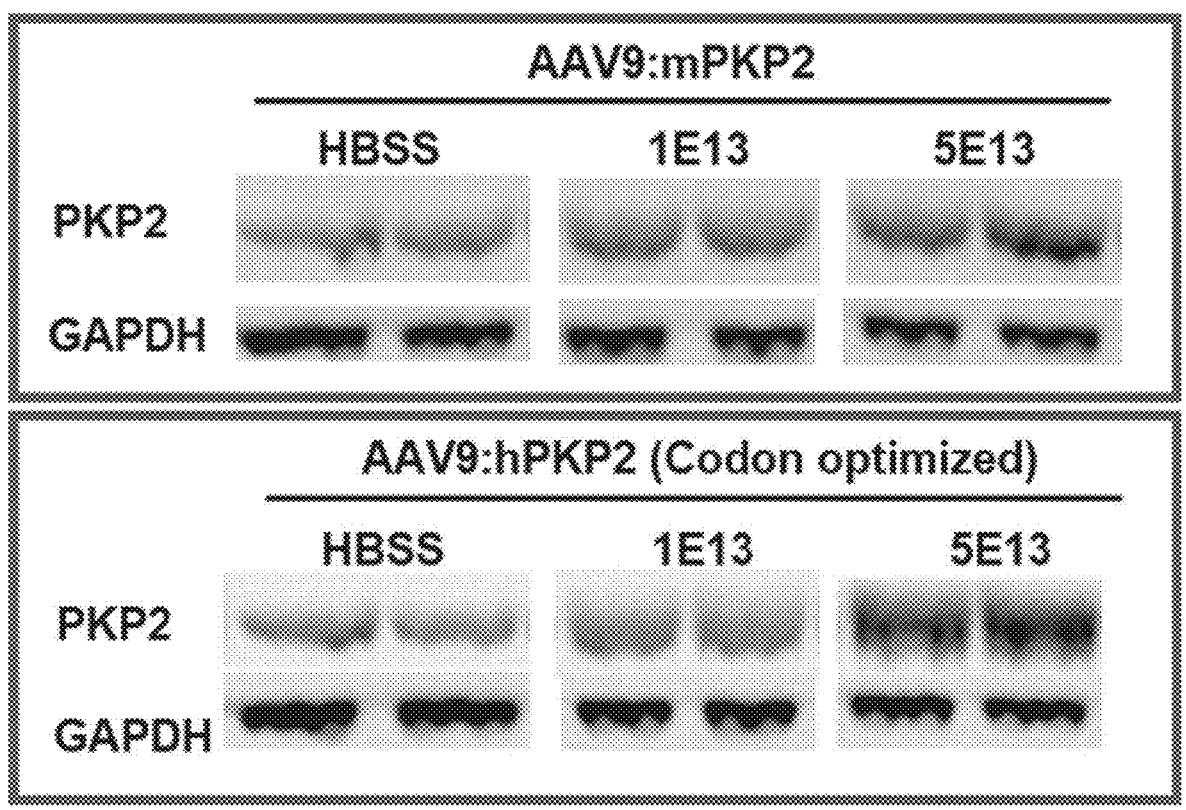
FIG. 18B shows immunoblots of protein expression of mouse and human PKP2a from mice treated with AAV9:PKP2.

FIG. 18A shows a schematic of the AAV expression cassettes for human and mouse PKP2α. The AAV-pTnT600-mPKP2-WPRE has 4199 basepairs which include inverted terminal repeats (ITR) on the 5' end and the 3' end, the pcTNT promoter followed by the coding sequence for mouse PKP2α, then the WPRE and bGH at the 3' end before the 3' ITR. The AAV-pTnT600-hPKP2op-WPRE has 4324 basepairs which include inverted terminal repeats (ITR) on the 5' end and the 3' end, the pcTNT promoter followed by a codon optimized coding sequence for human PKP2α, then the WPRE and bGH at the 3' end before the 3' TR. FIG. 18B shows immunoblots of protein expression of mouse and human PKP2α from wildtype mice treated with AAV9:PKP2 (see full blots in FIG. 10). Buffer treated mice are in the left panel. The middle panel shows an immunoblot from mice treated with 1E13 viral genomes per kg with the AAV9:mPKP2 in the top immunoblot and the AAV9:hPKP2 (codon optimized) in the bottom immunoblot. The right panel shows immunoblots from mice treated with 5E13 viral genomes per kg with the AAV9:mPKP2 in the top immunoblot and the AAV9:hPKP2 (codon optimized) in the bottom immunoblot.

Figure 19:
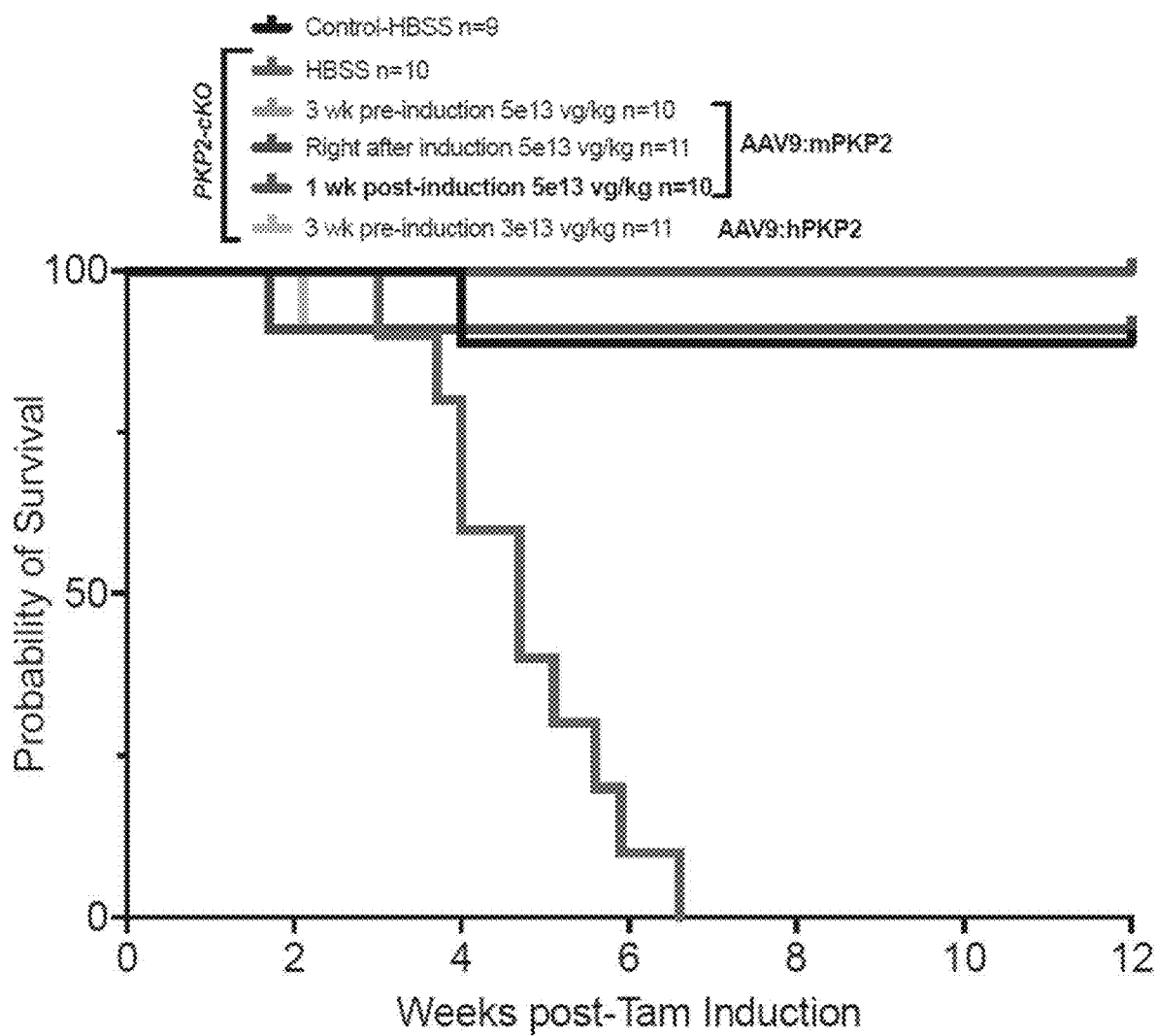
FIG. 19 shows a Kaplan-Meier survival curve of PKP2-cKO mice treated with AAV9:PKP2.

FIG. 19 shows a Kaplan-Meier survival curve of PKP2-cKO mice treated with AAV9:PKP2. Mice treated with buffer are shown in the red line that begins declining at three weeks post tamoxifen induction and near zero probability of survival at six weeks post-tamoxifen induction. All of the treated groups have 90% or greater probability of survival at six weeks post-tamoxifen induction.

Figure 20A:
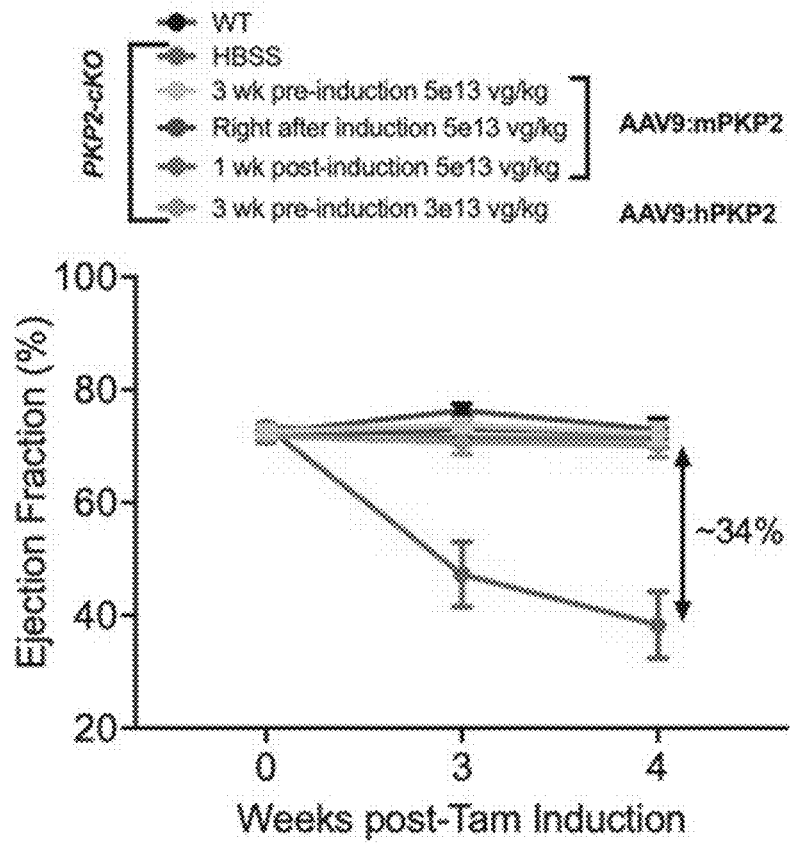
FIGS. 20A-20C show the efficacy of AAV9:PKP2 treatment of PKP2-cKO mice in reducing RV and LV dilation and maintaining cardiac function.
Figure 20B:
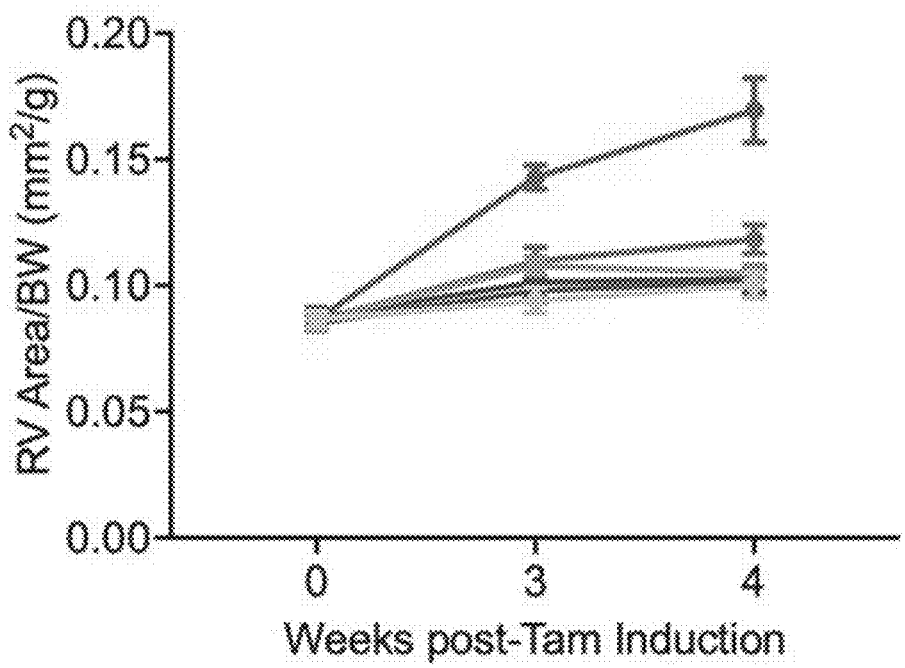
Figure 20C:
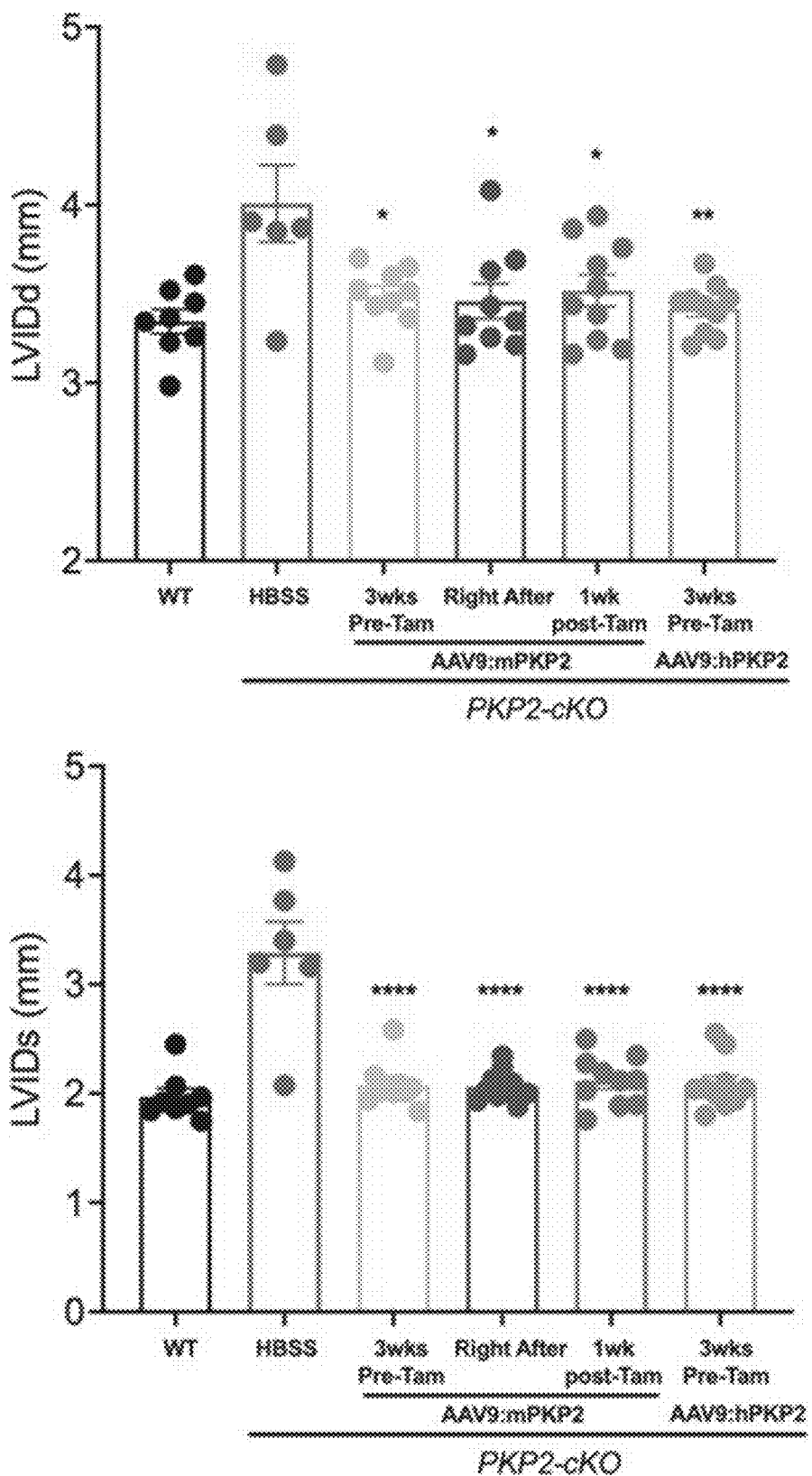

FIGS. 20A-20C show the efficacy of AAV9:PKP2 treatment of PKP2-cKO mice in reducing RV and LV dilation and maintaining cardiac function. FIG. 20A shows a graph illustrating improvement in ejection fraction in AAV9:PKP2 treated mice. In this graph buffer treated PKP2-cKO mice have a 34% reduction in ejection fraction compared to both wildtype and AAV9:PKP2 treated mice. FIG. 20B shows a graph illustrating reduction of RV dilation in AAV9:PKP2 treated mice compared with buffer treated mice which are shown in the red line that is elevated in the graph compared to wildtype mice and AAV9:PKP2 treated mice. FIG. 20C shows graphs illustrating improvement in LVIDd (top) and LVIDs (bottom). Each treatment group is illustrated by a separate bar graph with wildtype and buffer treated PKP2-cKO mice on the left side.

Figure 21A:
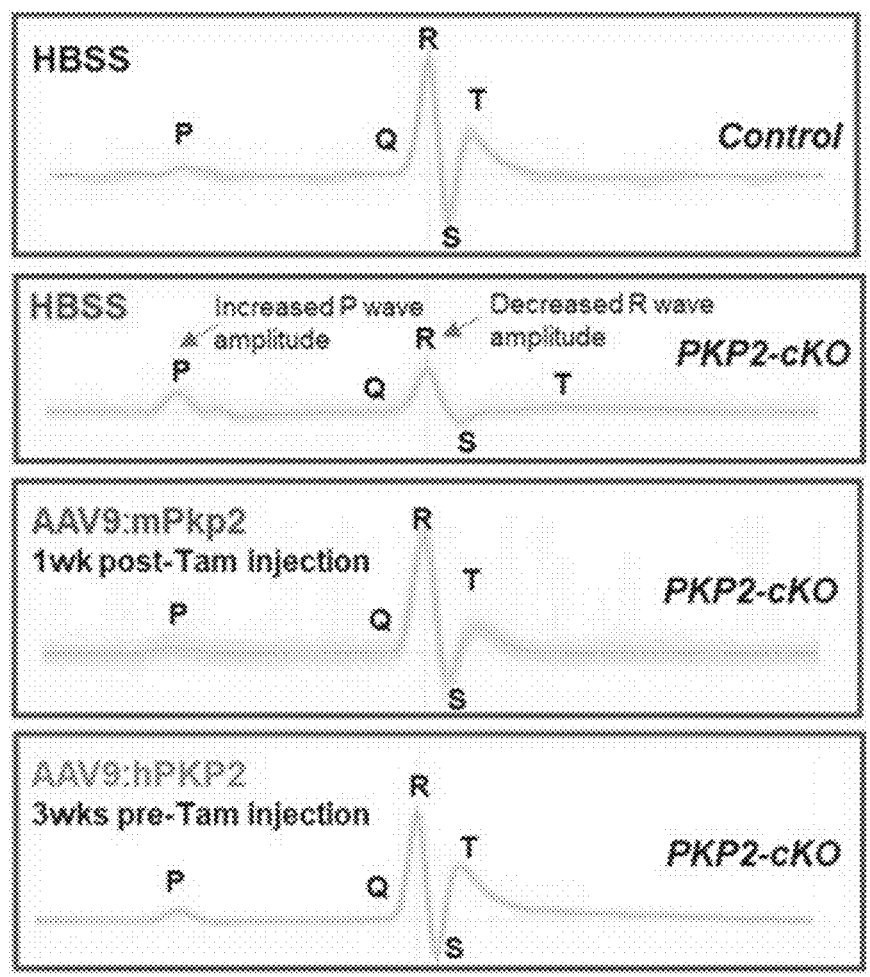
FIGS. 21A-21B show improvement in ECG parameters of PKP2-cKO mice treated with AAV:PKP2.
Figure 21B:
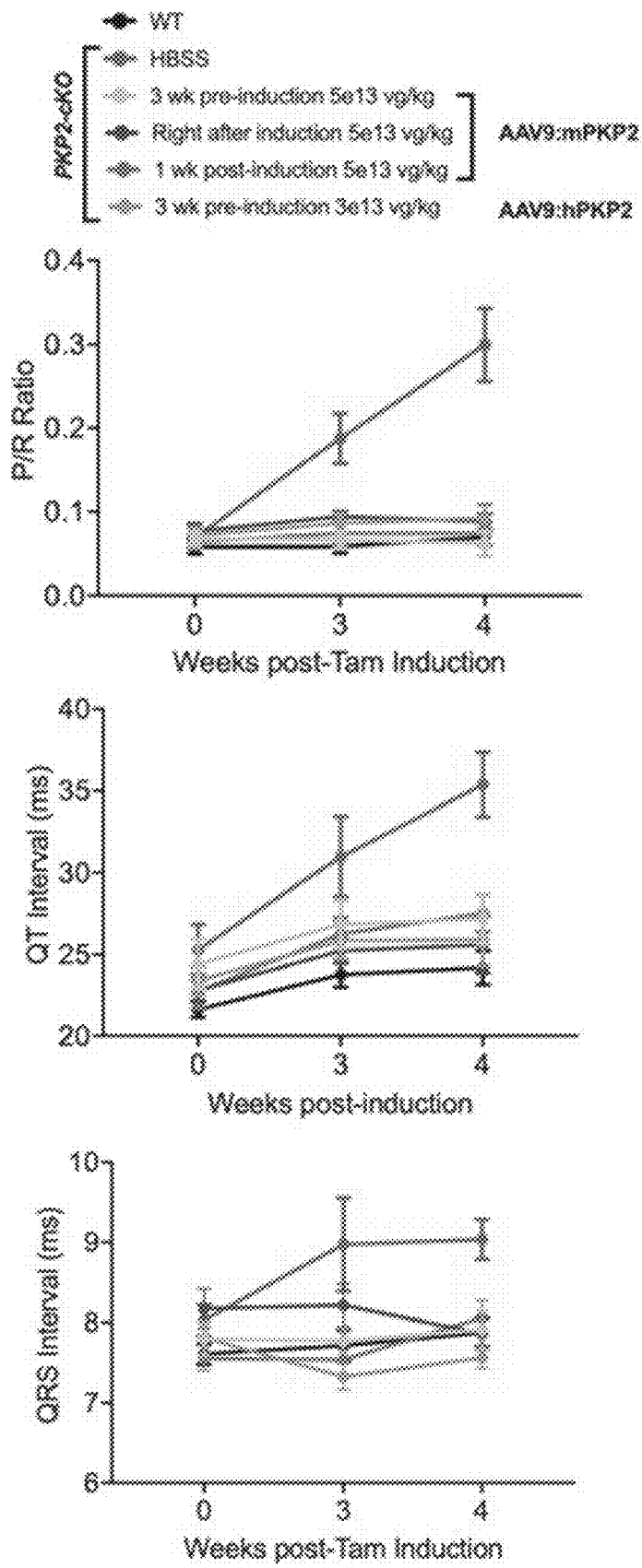

FIGS. 21A-21B show improvement in ECG parameters of PKP2-cKO mice treated with AAV:PKP2. FIG. 21A shows exemplary raw ECG traces of control and PKP2-cKO mice treated with AAV9:PKP2 and buffer. The ECG traces of buffer treated control and PKP2-cKO mice are shown on the top two panels. AAV9:PKP2 treated PKP2-cKO mice are shown in the bottom two traces. FIG. 21B shows graphs illustrating improvement of P/R ratio (top graph), QT interval (middle graph), and QRS interval (bottom graph) in PKP2-cKO mice treated with AAV9:PKP2 compared with treatment with buffer. In each instance, buffer treated PKP2-cKO mice are outliers with the treated and wild type mice.

Figure 22A:
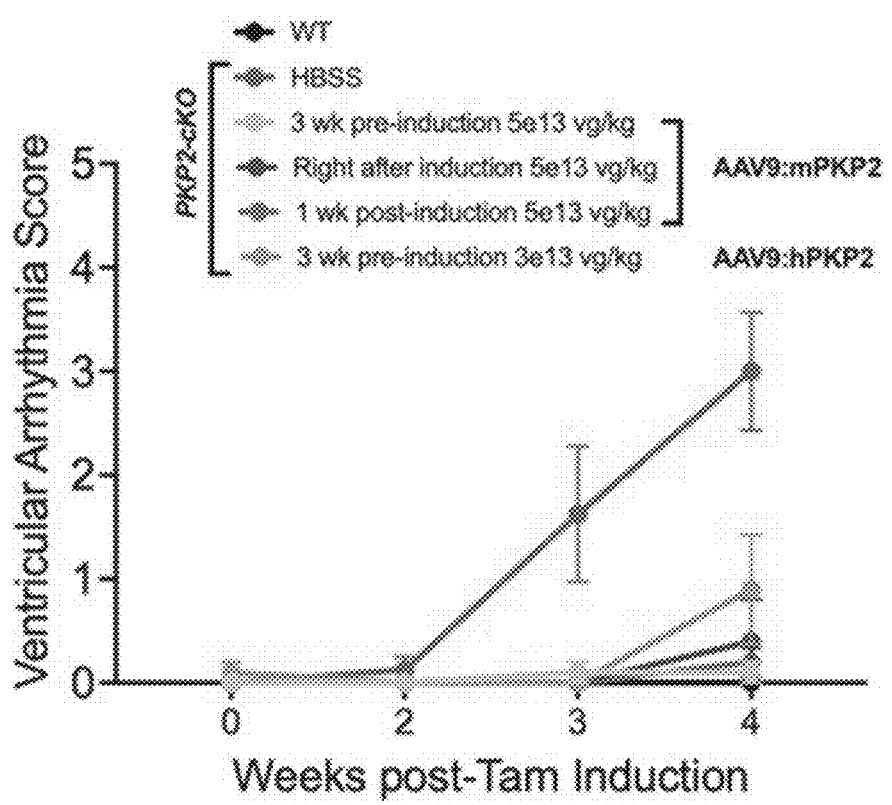
FIGS. 22A-22B show AAV9:PKP2 treatment improvement in arrhythmias in PKP2-cKO mice.
Figure 22B:
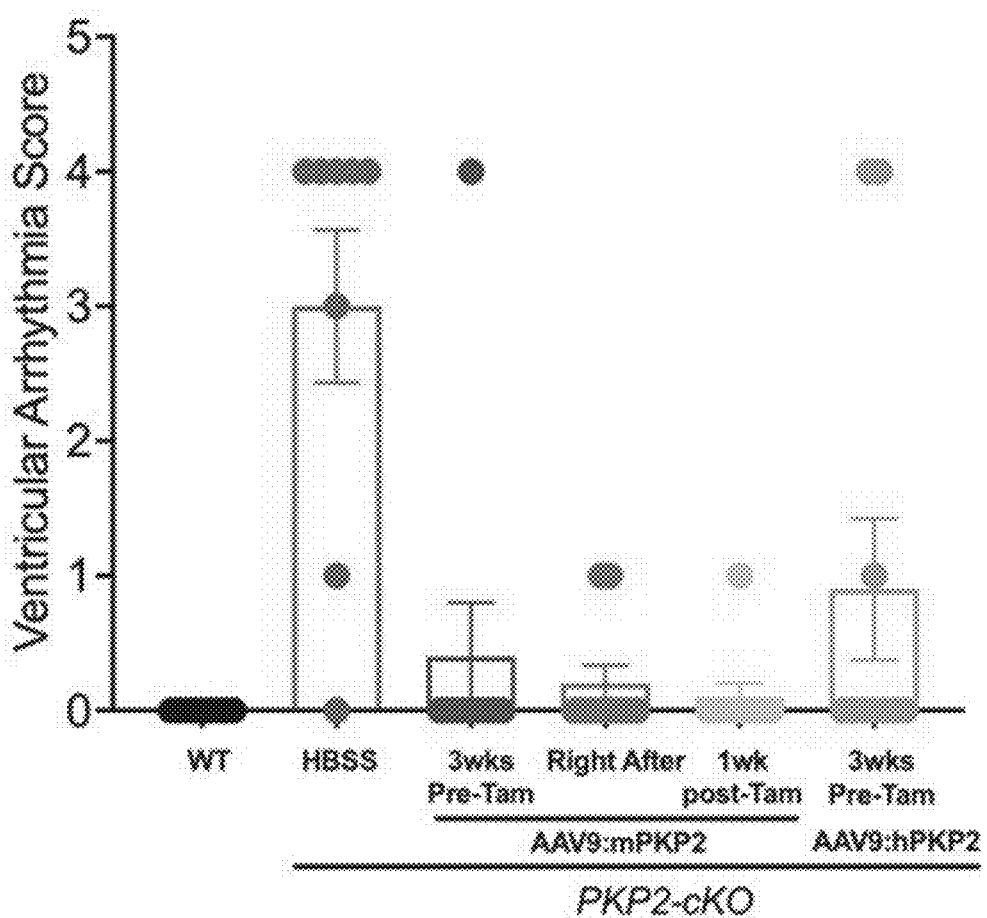

FIGS. 22A-22B show AAV9:PKP2 treatment improvement in arrhythmias in PKP2-cKO mice. FIG. 22A (top) shows a table grading of severity of arrhythmias. Grade 5 represents S-VT/VF/cardiac sudden death; 4 represents NSVT; 3 represents >100 PVCs, couplets and triplets; 2 represents >50,<100 PVCs; 1 represents <50 PVCs, PJCs, and AV block; and 0 represents <10 PVCs. FIG. 22A (bottom) shows a graph which summarizes improvement of arrhythmia scores of PKP2-cKO mice treated with AAV9: PKP2 compared with control. The buffer treated PKP2-cKO mice with an increase in ventricular arrhythmia score starting three weeks post-tamoxifen induction. FIG. 22B shows a distribution graph showing improvement in severity of arrhythmias in PKP2-cKO mice treated with AAV9:PKP2 compared with control. Wildtype mice are shown in the left most bar graph followed by buffer treated PKP2-cKO mice which showed an average score of 3. Treated mice are represented by the four bar graphs which show, on average, a dramatic decrease in score.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the claims. Changes therein and other uses which are encompassed within the spirit of the disclosure as defined by the scope of the claims will occur to those skilled in the art.

Example 1: Cellular Model of PKP2 Depletion

As an initial proof of concept, a cellular model of depletion of PKP2 was created using siRNA. PKP2 was depleted in in induced pluripotent stem cell-derived cardiomyocytes (iPSCM). Acute silencing of PKP2 by siRNAs was performed using siRNAs purchased from Invitrogen including both siPKP2 and negative control siRNA (4390843 Silencer Select Negative Control No. 1 siRNA; 4392420 Assay Id s531202 Silencer Select Pre-Designed siRNA #1; 4392420 Assay Id s531203 Silencer Select Pre-Designed siRNA #2; 4392420 Assay Id s531204 Silencer Select Pre-Designed siRNA #3; and 4392420 Assay Id s10585 Silencer Select Pre-Designed siRNA #4). This silencing led to disappearance of DSP from the cellular membrane at day 8 as shown by immunofluorescence at FIG. 3A. The DSP membrane localization was quantitatively measured (FIG. 4) which illustrated a significant reduction in DSP-PKG co-localization. A reduction of sarcomere density was also observed by immunofluorescence (FIG. 3B). In addition, a disarray of cell compaction in patterned iPSCM was seen by immunofluorescence (FIG. 3C).

An immunoblot of siPKP2 iPSCM lysate was performed showing that a reduced total amount of DSP protein from the desmosomes is detected mainly in the insoluble fraction of cells were PKP2 is silenced (FIG. 5).

Example 2: AAV9-PKP2 Rescues PKP2 Depletion Phenotype

By delivering AAV9 variant CR9-01 flag-tagged PKP2 expression driven by 600 nt cardiac troponin (TnT) promoter with GFP to identify transduced cells (FIG. 6A), re-localization of DSP back to the membrane in PKP2 silenced iPSCM was observed (FIG. 6B), thereby restoring desmosome structure. PKP2 transgene was codon optimized to resist siRNA-mediated silencing. Due to a technical difficulty, it was not possible accurately quantify how much DSP was specifically localized to the membrane where cellular junction occurs and desmosomes exist. Therefore, the total cellular DSP intensity, instead of an amount of DSP localized to membrane, was quantified.

To demonstrate that PKP2 transgene could functionally restore the contractility of cardiomyocytes, bright field-based contraction of iPSCM was recorded by SONY imaging and videos were analyzed by DANA Solutions Pulse analysis software. An experimental timeline is shown in FIG. 7A. In this experiment, siRNA was used to deplete endogenous PKP2 expression in iPSCM cells on day 1. Two siRNA concentrations, 5 and 1.25 nM, were used for either siRNA negative control or siPKP2. Two siPKP2 #3 and #4 were combined to silence the transcript. On day 3, an AAV PKP2 was used to transduce depleted cells resulting in a rescue of contraction velocity was observed in iPSCM in response to PKP2 transgene expression (FIG. 7B). Contractility was recorded at days 3, 4, 5, 6, 7, and 8 post AAV transduction. Contraction velocity was averaged from three 96-well plates and from cells transduced with either AAV 300K MOI or 100K MOI, respectively, at both 5 and 1.25 nM siRNAs. The velocity value was further normalized to the average nuclear count corresponding to 300K or 100K MOI, respectively.

Example 3: Treatment with Second Generation PKP2α AAV9

A second generation AAV expression cassette was developed for expressing human or mouse PKP2α. The second generation cassette included a Woodchuck Hepatitis Virus Posttranscriptional Regulatory Element (WPRE) and a bovine growth hormone polyadenylation signal (bGH poly (A)). The second generation vector is illustrated in FIG. 8.

Transgene rescue studies were conducted in PKP2 silenced iPSC cardiomyocytes. Preliminary results suggested that the second generation AAV-hPKP2α partially rescued contraction velocity post PKP2 silencing in iPSC cardiomyocytes. FIG. 9A shows results where human PKP2α transgene was expressed in iPSC cardiomyocytes in a dose-dependent fashion by different MOI (multiplicity of infection, the average number of virus particles infecting each cells). PKP2 and DSP (desmoplakin) expression were evaluated in both soluble and insoluble fractions of cells at 3 days post AAV transduction. FIG. 9B shows that human PKP2α transgene showed a partial rescue of contraction velocity post PKP2 silencing at 30K MOI as indicated by Student t test with a p value of 0.0103 in contrast to a p value of <0.0001 without AAV PKP2 transgene.

An experiment was conducted to study expression analysis of the second generation AAV9 human and mouse PKP2α in 12 week-old C57BL/6 animals. The results of this experiment are shown in FIG. 10. Animals were retro-orbital intravenously administered with AAV9-PKP2α at doses of 1E13 and 5E13 vg/kg, respectively. Heart LV tissues were harvested at 3.5 weeks post injection. Soluble fraction of LV tissues were analyzed here with Western blot. The upper panel shows expression of endogenous mouse PKP2α in HBSS control mice and expression of both endogenous and transduced mouse PKP2α at two AAV9 injected doses, 1E13 and 5E13, respectively. The lower panel shows corresponding expression analysis of transduced human PKP2α, a slightly larger homolog. This human homolog is codon optimized. There were no adverse cardiac event observed at 3.5 weeks post AAV injection by echocardiogram.

FIGS. 11A-G show pilot expression safety studies of second generation AAV9 human and mouse PKP2α in 12 week-old C57BL/6 animals did not show any adverse cardiac event at 3 weeks post AAV injection by echocardiogram. Animals were retro-orbital intravenously administrated with AAV9-PKP2α at doses of 1E13 and 5E13 vg/kg, respectively. FIG. 11A shows body weight before AAV9 injection and body weight at 3 weeks post AAV9 injection. FIG. 11B shows heart function measured by percentage of ejection fraction at 3 weeks post AAV9 injection of either mouse or human PKP2α. FIGS. 11C and 11D show LV structure measured by both internal diameters end diastole and systole. FIG. 11E-11F show electrophysiology activity measured by QRS, QT interval, and P/R amplitude.

Example 4: PKP2-cKO ARVC Mouse Model Characterization

Four wild-type and seven PKP2-cKO ARVC mice, αMYHC-Cre-ER(T2), PKP2O, at approximately 3 months of age were intraperitoneally injected for four consecutive days with tamoxifen (20 mg/ml in corn oil 100 µl/mice (approximately 75 mg/kg)). Baseline readings of body weight, echocardiography, and EKG were collected before tamoxifen induction. All readings post-tamoxifen induction were recorded weekly including echocardiography of B-mode, M-mode (RV, LV), and structure (LV internal diameters) and 30-minute ECG for quantifying arrythmias and evaluating electrophysiological parameters. Terminal tissues, including heart and lung, were collected at the end of the study.

A survival analysis was performed on the mice (FIG. 12). The Kaplan-Meier survival curve showed a sharp decline of survival of PKP2-cKO mice three weeks post-tamoxifen induction, with only one animal reaching six weeks post-tamoxifen induction. Animals showed severe clinical symptoms including sudden death, edema, reduced activity, less tolerance to isoflurane three weeks post-induction.

PKP2-cKO mice developed RV dilated cardiomyopathy at as early as one week post-tamoxifen induction. FIG. 13A, in the left panel, shows that at three weeks post-tamoxifen induction, PKP2-cKO mice developed an increased RV internal dimension at end-diastole (RVIDd). The right panel of FIG. 13A summarizes the continuous increases in RVIDd normalized to body weight during four weeks of tamoxifen induction. FIG. 13B, in the left panel, shows images of weekly increases in RV area suggesting RV dilation. The right panel of FIG. 13B summarizes the RV area increases normalized to body weight. P value: Student's t-test. Error bar: s.e.m. *P<0.05, **P<0.01 Vs. Control.

PKP2-cKO mice developed LV dilated cardiomyopathy post-tamoxifen induction. FIG. 14A, left panel, shows that at three weeks post-tamoxifen induction, PKP2-cKO developed an increased LV internal dimension at end-systole (LVIDs) and end diastole (LVIDd). The right panel of FIG. 14A summarizes the continuous increases in LVIDs and LVIDd normalized to body weight during four weeks of tamoxifen induction. FIG. 14B shows LV performance as measured by % ejection fraction sharply declined after two weeks post-tamoxifen induction. P value: Student's t-test. Error bar: s.e.m. *P<0.05, P<0.01, *P<0.001 Vs. Control.

PKP2-cKO mice developed prolonged QRS interval and increased P/R amplitude ratio suggesting ventricular conduction disturbance and intraventricular block. FIG. 15 top panel shows that at three weeks post-tamoxifen induction, PKP2-cKO mice developed an increased P wave amplitude and decreased R wave amplitude. The bottom left graph in FIG. 15 shows the continuous increases in QRS interval and the lower right graph shows the increase in P/R amplitude ratio during four weeks of tamoxifen induction. P value: Student's t-test. Error bar: s.e.m. *P<0.05, P<0.01, *P<0.001 Vs. Control.

PKP2-cKO mice developed spontaneous premature ventricular contractions (PVCs). Table 2 shows data obtained during 30 minutes of continuous recording, PVCs were nearly absent at one week, whereas occasional extra systoles were detected in all the PKP2-cKO animals at two weeks. The occurrence of PVCs increased further at later times with a majority of animals showing over 100 PVCs. Starting from three weeks, sudden cardiac death was observed in PKP2-cKO animals.

TABLE 2

PKP2-cKO ARVC Mouse Model PVC

| Animal ID | Week Post Tamoxifen induction | | | |
|---|---|---|---|---|
| | Week-1 | Week-2 | Week-3 | Week-4 |
| 121 | 0 | 5 | >100 | Died |
| 125 | 0 | 12 | 12 | Died |
| 130 | 0 | 2 | Died | Died |
| 137 | 0 | 66 | >100 | N/A |
| 138 | 0 | 20 | >100 | Died |
| 150 | 0 | 1 | 11 | >100 |
| 152 | 4 | 5 | >100 | >100 |

PKP2-cKO mice showed enhanced expression of fibrosis, tissue remodeling genes, and heart failure markers. FIG. 16A, top panel, shows PKP2 mRNA expression in both RV and LV of wild type and PKP2-cKO mice. Red and blue dots represent each individual mouse. The bottom panel of FIG. 16A shows representative immunoblots of reduction in LV protein levels of PKP2, DSP, and PKG in desmosome and Cx43 in gap junction. FIG. 16B shows that PKP2-cKO mice showed enhanced expression of fibrosis genes, TGFβ1, Col1a1, and Col3a1, and tissue remodeling genes, Timp1 and Mmp2. FIG. 16C shows PKP2-cKO mice showed enhanced expression of heart failure markers, NPPA and NPPB.

Example 5: PKP2 Gene Therapy Efficacy in PKP2-cKO ARVC Mouse Model

FIG. 17 shows the experimental design used to evaluate PKP2 efficacy as a gene therapy target using the PKP2-cKO ARVC mouse model. A total of six individual treatment groups were included in the studies and all groups were tamoxifen treated for three consecutive days. The treatment groups are as follows: six wildtype mice treated with HBSS buffer; ten PKP2-cKO ARVC mice treated with HBSS buffer; ten PKP2-cKO ARVC mice treated with 3E13 vg/kg of AAV9:hman PKP2 at three weeks before tamoxifen induction; ten PKP2-cKO ARVC mice treated with 5E13 vg/kg of AAV9:mouse PKP2 at three weeks before tamoxifen induction; ten PKP2-cKO ARVC mice treated with 5E13 vg/kg of AAV9:mouse PKP2 right after tamoxifen induction; and ten PKP2-cKO ARVC mice with 5E13 vg/kg of AAV9:mouse PKP2 at one week after tamoxifen induction.

Baseline recordings of body weight, echocardiography, and EKG were collected before tamoxifen induction. All readings post tamoxifen induction were recorded weekly including echocardiography of B-mode, M-mode (RV, LV) and structure (LV internal diameters), and 30-minute ECG for quantifying arrythmias and evaluating electrophysiological parameters. Terminal tissues (heart and lung) will be collected at the end of the study.

AAV9:PKP2 protein expression was detected in wildtype mouse LV heart tissue. FIG. 18A shows a schematic representation of the second generation AAV expression cassette of human and mouse PKP2α. FIG. 18B shows representative immunoblots conducted to show expression of mouse and human PKP2 at three weeks post retro-orbital injection of AAV9:PKP2 (full blots are shown in FIG. 10). A total of five C57BL6 wildtype mice at eight weeks of age were injected for each treatment: HBSS, 1E13 vg/kg, or 5E13 vg/kg.

A Kaplan-Meier survival curve showed that AAV9:PKP2 extended life span of PKP2-cKO mice after 6 weeks post-tamoxifen induction in all AAV9:PKP2 treated groups. Both human and mouse PKP2 demonstrated efficacy in extending life span of treated PKP2-cKO mice. In FIG. 19, the red line is PKP2-cKO mice treated with HBSS buffer showing a sharp decline after three weeks post-tamoxifen induction. In contrast, all AAV9-PKP2 treated mice survived until six weeks post-tamoxifen induction.

AAV9:PKP2 treatment of PKP2-cKO mice showed efficacy in reducing RV and LV dilation and maintaining cardiac function. FIG. 20A shows AAV9:PKP2 treatment prevented a decline in percent ejection fraction compared to HBSS-treated mice (shown in the red line). FIG. 20B shows AAV9:PKP2 treatment showed a reduction of RV dilation at weekly bases as estimated by RV area normalized to body weight. FIG. 20C shows at four weeks post-tamoxifen induction, AAV9:PKP2 treatment significantly reduced LV dilation of PKP2-cKO mice as measured by both LV internal dimension at end-diastole (LVIDd) (top graph) and LV internal dimension at end-systole (LVIDs) (bottom graph), both normalized by body weight. Error bar: s.e.m. *$P<0.05$, $P<0.01$, *$P<0.001$ Vs. Control.

AAV9:PKP2 treatment also significantly improved ECG parameters of PKP2-cKO mice. FIG. 21A shows examples of raw ECG traces which showed a significant improvement of electrophysiological behaviors of AAV9:PKP2 treated PKP2-cKO mouse hearts. FIG. 21B shows AAV9:PKP2 treatment showed significant improvement of P/R ratio (top graph), QT interval (middle graph), and QRS interval (bottom graph) as compared to PKP2-cKO mice treated with HBSS shown in red lines.

AAV9:PKP2 treatment also significantly reduced arrhythmias in PKP2-cKO mice. FIG. 22A (top) shows a table with a grading chart to categorize severity of spontaneous arrhythmias during 30 minutes of recording in anesthetized PKP2-cKO mice. Premature ventricular contractions (IPVCs), premature junctional complexes (PJCs), AV block (atrioventricular block), non-sustained ventricular tachycardia (NSVT), supraventricular tachycardia (S-VT), and ventricular fibrillation. FIG. 22A (bottom) summarizes averaged scores based on the grading chart showing amelioration of arrhythmias in AAV9:PKP2 treated PKP2-cKO mice. FIG. 22B shows a distribution of individual mice in each treatment group at four weeks post-tamoxifen induction. AAV9:PKP2 treatment showed a reduction of both arrhythmia event frequency and severity as indicated by improved arrhythmia scores when compared to PKP2-cKO mice treated with HBSS buffer shown in the red bar.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein may be employed. It is intended that the following claims define the scope of the disclosure and that methods and structures within the scope of these claims and their equivalents be covered thereby.

What is claimed is:

1. A method for treating arrhythmogenic right ventricular cardiomyopathy (ARVC) or arrhythmogenic cardiomyopathy (ACM) in a mammal with ARVC or ACM, the method comprising administering a composition to the mammal intravenously, intracardially, pericardially, or intraarterially such that the ARVC or ACM is treated in the mammal, wherein the composition comprises (a) a viral vector comprising a nucleic acid sequence that is at least 90% identical to SEQ ID NO: 2 encoding a plakophilin 2 (PKP2) polypeptide having the amino acid sequence of SEQ ID NO: 8 operatively linked to a cardiac specific promoter and a 3' element; and (b) a pharmaceutically acceptable carrier or excipient.

2. The method of claim 1, wherein the viral vector comprises a viral vector selected from the group consisting of an adeno-associated virus, an adenovirus, a lentivirus, a pox virus, a vaccinia virus, and a herpes virus.

3. The method of claim 1, wherein the viral vector is an adeno-associated virus.

4. The method of claim 3, wherein the adeno-associated virus is selected from the group consisting of an AAV6, an AAV8, an AAV9, and an AAV.rh74.

5. The method of claim 4, wherein the adeno-associated virus is an AAV9.

6. The method of claim 1, wherein the cardiac specific promoter is a PKP2 promoter, a troponin promoter, or an alpha-myosin heavy chain promoter.

7. The method of claim 1, wherein the 3' element comprises a Woodchuck Hepatitis Virus Posttransciptional Regulatory Element (WPRE), a bovine growth hormone polyadenylation (bGH polyA) sequence, or a combination thereof.

8. The method of claim 1, wherein the viral vector further comprises a cardiac specific enhancer.

9. The method of claim 1, wherein the nucleic acid sequence has a size less than or equal to about 4.7 kb.

10. The method of claim 1, wherein the pharmaceutically acceptable carrier or excipient comprises a buffer, a polymer, a salt, or a combination thereof.

11. The method of claim 1, wherein the method reverses or reduces at least one of fibrofatty tissue replacement; myocardial atrophy; predominant right ventricular dilation; ventricular arrhythmias; sudden cardiac death; exercise-triggered cardiac events; right ventricular cardiomyopathy, dilation, or heart failure; left ventricular cardiomyopathy, dilation, or heart failure; atrial arrhythmias; syncope; palpitations; shortness of breath; or chest pain.

12. The method of claim 1, wherein the method restores expression of one or more genes having a direct or indirect effect on one or more symptoms of the heart disease.

13. The method of claim 12, wherein the one or more genes comprises one or more of Ryanodine Receptor 2 (Ryr2), Ankyrin-B (Ank2), Cacna1c (CaV1.2), Triadin (Trdn), or Calsequestrin-2 (Casq2).

14. The method of claim 1, wherein the mammal is identified as having at least one variation in a desmosome protein.

15. The method of claim 14, wherein the desmosome protein is PKP2.

16. The method of claim 15, wherein the variation comprises a deletion, an insertion, a single nucleotide variation, or a copy number variation.

17. The method of claim 1, wherein the nucleic acid sequence is at least 95% identical to SEQ ID NO: 2.

\* \* \* \* \*

SEQUENCE LISTING

<160> NUMBER OF SEQ ID NOS: 11

<210> SEQ ID NO 1
<211> LENGTH: 2514
<212> TYPE: DNA
<213> ORGANISM: Homo sapiens

<400> SEQUENCE: 1

```
atggcagccc ccggcgcccc agctgagtac ggctacatcc ggaccgtcct gggccagcag      60
atcctgggac aactggacag ctccagcctg gcgctgcccc ccgaggccaa gctgaagctg     120
gcggggagca gcggccgcgg cggccagaca gtcaagagcc tgcggatcca ggagcaggtg     180
cagcagaccc tcgcccggaa gggccgcagc tccgtgggca acggaaatct tcaccgaacc     240
agcagtgttc ctgagtatgt ctacaaccta cacttggttg aaaatgattt tgttggaggc     300
cgttcccctg ttcctaaaac ctatgacatg ctaaaggctg gcacaactgc cacttatgaa     360
ggtcgctggg gaagaggaac agcacagtac agctcccaga agtccgtgga agaaaggtcc     420
ttgaggcatc ctctgaggag actggagatt tctcctgaca gcagcccgga gagggctcac     480
tacacgcaca gcgattacca gtacagccag agaagccagg ctgggcacac cctgcaccac     540
caagaaagca ggcgggccgc cctcctagtg ccaccgagat atgctcgttc cgagatcgtg     600
ggggtcagcc gtgctggcac cacaagcagg cagcgccact ttgacacata ccacagacag     660
taccagcatg gctctgttag cgacaccgtt tttgacagca tccctgccaa cccggccctg     720
```

```
ctcacgtacc ccaggccagg gaccagccgc agcatgggca acctcttgga gaaggagaac      780
tacctgacgg cagggctcac tgtcgggcag gtcaggccgc tggtgcccct gcagcccgtc      840
actcagaaca gggcttccag gtcctcctgg catcagagct ccttccacag cacccgcacg      900
ctgagggaag ctgggcccag tgtcgccgtg gattccagcg ggaggagagc gcacttgact      960
gtcggccagg cggccgcagg gggaagtggg aatctgctca ctgagagaag cactttcact     1020
gactcccagc tggggaatgc agacatggag atgactctgg agcgagcagt gagtatgctc     1080
gaggcagacc acatgctgcc atccaggatt tctgctgcag ctactttcat acagcacgag     1140
tgcttccaga atctgaagc tcggaagagg gttaaccagc ttcgtggcat cctcaagctt      1200
ctgcagctcc taaaagttca gaatgaagac gttcagcgag ctgtgtgtgg ggccttgaga     1260
aacttagtat ttgaagacaa tgacaacaaa ttggaggtgg ctgaactaaa tggggtacct     1320
cggctgctcc aggtgctgaa gcaaaccaga gacttggaga ctaaaaaaca aataacaggt     1380
ttgctgtgga atttgtcatc taatgacaaa ctcaagaatc tcatgataac agaagcattg     1440
cttacgctga cggagaatat catcatcccc ttttctgggt ggcctgaagg agactaccca     1500
aaagcaaatg gtttgctcga ttttgacata ttctacaacg tcactggatg cctaagaaac     1560
atgagttctg ctggcgctga tgggagaaaa gcgatgagaa gatgtgacgg actcattgac     1620
tcactggtcc attatgtcag aggaaccatt gcagattacc agccagatga caaggccacg     1680
gagaattgtg tgtgcattct tcataacctc tcctaccagc tggaggcaga gctcccagag     1740
aaatattccc agaatatcta tattcaaaac cggaatatcc agactgacaa caacaaaagt     1800
attggatgtt ttggcagtcg aagcaggaaa gtaaagagc aataccagga cgtgccgatg     1860
ccggaggaaa agagcaaccc caagggcgtg gagtggctgt ggcattccat tgttataagg     1920
atgtatctgt ccttgatcgc caaaagtgtc cgcaactaca cacaagaagc atccttagga     1980
gctctgcaga acctcacggc cggaagtgga ccaatgccga catcagtggc tcagacagtt     2040
gtccagaagg aaagtggcct gcagcacacc cgaaagatgc tgcatgttgg tgacccaagt     2100
gtgaaaaaga cagccatctc gctgctgagg aatctgtccc ggaatctttc tctgcagaat     2160
gaaattgcca agaaactct ccctgatttg gttccatca ttcctgacac agtcccgagt      2220
actgaccttc tcattgaaac tacagcctct gcctgttaca cattgaacaa cataatccaa     2280
aacagttacc agaatgcacg cgaccttcta aacaccgggg gcatccagaa aatttatggcc    2340 attagtgcag gcgatgccta tgcctccaac aaagcaagta agctgcttc cgtccttctg      2400 tattctctgt gggcacacac ggaactgcat catgcctaca agaaggctca gtttaagaag     2460
acagattttg tcaacagccg gactgccaaa gcctaccact cccttaaaga ctga           2514
```

<210> SEQ ID NO 2
<211> LENGTH: 2511
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
atggctgctc ctggtgctcc tgccgagtac ggctacatca gaacagtgct gggccagcag       60
atcctgggac agctggattc tagctctctg gccctgcctt ctgaggccaa gctgaaactg      120
gccggcagtt ctggaagagg cggccagaca gtgaagtccc tgcggatcca agaacaggtg      180
cagcagaccc tggccagaaa gggcagatct tctgtcggca acggcaacct gcacagaacc      240
```

```
agctctgtgc ccgagtacgt gtacaatctg cacctggtgg aaaacgactt cgtcggcggc    300
agatcccctg tgcctaagac ctacgatatg ctgaaggccg gcaccaccgc cacctatgaa    360
ggcagatggg gaagaggcac agcccagtac agcagccaga aaagcgtgga agagagaagc    420
ctgcggcacc ctctgcggag actggaaatc agccctgata gcagcccaga gagagcccac    480
tacacccaca gcgactacca gtactcccag agatctcagg ccggccacac actgcaccac    540
caagagtcta aagggccgc tctgctggtg cctcctagat acgccagatc tgagatcgtg     600
ggcgtgtcca gagccggcac aacaagcaga cagagacact tcgacaccta ccaccggcag    660
tatcagcacg gcagcgtgtc cgataccgtg ttcgatagca tccccgccaa tcctgctctg    720
ctgacatacc ctagacctgg cacctccaga tccatgggca atctgctgga aaagagaac    780
tacctgaccg ccggactgac cgtgggacaa gttcgacctc tggttcctct gcagcccgtg    840
acacagaaca gagccagcag aagcagctgg caccagtcca gcttccacag caccagaaca    900
ctgagagaag ctgccctag cgtggccgtg gattcttctg gtagaagggc tcacctgaca    960
gttggccaag cagctgcagg cggaagcgga atctgctga ccgagagaag caccttcacc    1020
gacagccagc tggcaacgc cgacatggaa atgacactgg aacgggccgt gtccatgctg    1080
gaagccgatc acatgctgcc cagcagaatt agcgccgctg ccacctttat ccagcacgag    1140
tgcttccaga gtctgaggc ccggaagaga gtgaaccagc tgagaggcat cctgaagctg    1200
ctgcagctcc tgaaggtgca gaacgaggat gtgcagaggg ctgtgtgtgg ggccctgaga    1260
aatctggtgt tcgaggacaa cgacaacaag ctggaagtgg ccgagctgaa cggcgtgcca    1320
agactgctgc aggttctgaa acagacccgc gacctggaaa caaagaagca gatcaccggc    1380
ctgctctgga acctgagcag caacgacaag ctgaagaacc tgatgatcac agaggccctg    1440
ctgaccctga cagagaacat catcatccct ttcagcggct ggcccgaggg cgattaccct    1500
aaagctaatg gcctgctgga cttcgacatc ttctacaacg tgaccggctg cctgagaaac    1560
atgtctagcg ctggcgccga tggcagaaag gccatgagaa gatgtgacgg cctgatcgac    1620
agcctggtgc actatgtgcg gggcacaatc gccgattacc agcctgatga taaggccacc    1680
gagaactgcg tgtgcatcct gcacaacctg agctaccagc tggaagcaga gctgcccgag    1740
aagtacagcc agaacatcta catccagaac cggaacatcc agaccgacaa caacaagagc    1800
atcggctgct cggcagccg cagccggaaa gtgaaagaac agtaccagga cgtgcccatg    1860
cctgaggaaa agtctaaccc caaaggcgtg gaatggctgt ggcacagcat cgtgatccgg    1920
atgtacctga gcctgatcgc caagagcgtg cggaattaca cccaagaggc atctctgggc    1980
gccctgcaga atctgacagc aggatctggc ctatgcctta cctctgtggc tcagaccgtg    2040
gtgcagaaag agtctggcct gcagcacacc cggaagatgc tgcatgtggg agatcccagc    2100
gtgaagaaaa ccgccatcag cctgctgaga acctgagcc ggaatctgtc tctgcagaat    2160
gagatcgcca agagacact gcccgacctg gtgtctatca tccctgacac cgtgcctagc    2220
accgacctgc tgattgagac aacagccagc gcctgctaca ccctgaacaa catcattcag    2280
aactcctacc agaacgcccg cgatctgctg aacacaggcg gcatccagaa aatcatggcc    2340
atctctgccg gcgacgccta cgcctctaac aaggcctcta agccgccag cgtgctgctg    2400
tattctctgt gggcccatac cgagctgcac catgcctata agaaggccca gttcaaaaag    2460
accgacttcg tgaacagccg gaccgccaag gcctaccact ctctgaaaga t             2511
```

<210> SEQ ID NO 3

```
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gtcatggaga agacccacct tgcagatgtc ctcactgggg ctggcagagc cggcaacctg      60
cctaaggctg ctcagtccat taggagccag tagcctggaa gatgtcttta cccccagcat     120
cagttcaagt ggagcagcac ataactcttg ccctctgcct tccaagattc tggtgctgag     180
acttatggag tgtcttggag gttgccttct gcccccaac cctgctccca gctggccctc      240
ccaggcctgg gttgctggcc tctgctttat caggattctc aagagggaca gctggtttat     300
gttgcatgac tgttccctgc atatctgctc tggttttaaa tagcttatct gagcagctgg     360
aggaccacat gggcttatat ggcgtgggt acatgttcct gtagccttgt ccctggcacc      420
tgccaaaata gcagccaaca cccccaccc ccaccgccat cccctgccc cacccgtccc       480 ctgtcgcaca ttcctccctc cgcagggctg gctcaccagg ccccagccca catgcctgct     540
taaagccctc tccatcctct gcctcaccca gtccccgctg agactgagca gacgcctcca    600

<210> SEQ ID NO 4
<211> LENGTH: 1624
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
catctcagca tcatggttgg atgtttccac ctggctacat aagcaagctt tacacaaggt      60
gtaatttgcc taaatagtgg tccattctat tggggtggga gcaattgctt ccaggactca     120
catccatatg gctcccactt agccatgtgg cctgctgaca aagggtggcg gaactgtcac     180
tactctgttg tccacgcttt cagtcctttg gtttcctctt cactccctgg acgctcatgt     240
aaaaagggag gccatatacc tgtgcattgt gtgtctaagc attcagtgtg tgtctaaagg     300
cagaagggtg tgggtaggaa acaaagacg agggaagctg cgttctccaa acacttcaga      360
cttgagtaag tggggttttg cagcaattga gtgatttgag ggaaagtgaa catacaaacc     420
caagcaatca aagggaatat tatcttaata ccagggatac atgttttct ttctgcctct      480 taagtccaaa gaggcaaatc aggacaagtg gctttggttg taaactttaa ggtcaaggat     540
cctttctgtt gagcttagct ctcaagttct cagtagtcaa ctgcggtgaa acataattaa     600
tagcacgata aatacaagtt gtggaagatt cgattgaaag ttggaggccc tctccgtgga     660
tctctctaca aagagcctgt aataaagagg acttaatcaa cgttagcagg gctatttaaa     720
aagcatcgtc tattaaaatt catttcttct ctagagcctc ttgttggagt ttctctgtgt     780
gggtgtgttc gtaagagagg aatgggttag caagagtact gggtacaatt tgtgtatcca     840
agagaaaaca gaagctctca atgaggaaga acatatgttt ctgggactgc atctgtgcaa     900
aaagtacata gtcctgacgt tgtactaaga aaaaaacac tctctttaga aagtcttta      960 tttcacacgt tatcttcttg gcacatttcc ctcatattgc cctttccgcc tgaccaaata    1020 gcccttctc accctcaggt ccaggaaaac caggaaacgt ttccaacagt gcgacaaagc     1080
ctgactaacc agacatacta ctcgctcggg gatcccggag gcaagcctca gtccaagaac    1140
aggagtgact ctcgagggct cacctgcctg cagggcagcc cctccctgca tcgagcggaa   1200
```

| | |
|---|---|
| atccatcctg tccagcgcgg ggcgtgggca gagcggggcg cggcccccggc aggcggtatc | 1260 |
| cgctgggact ccgacaacgt gcgcgacccc aggcgaaccg cgcccctctc cccacctccc | 1320 |
| cgcgggcggg tacaagtctc caggtgtccg cgcgctcagc gggtccggcc cgccccgcc | 1380 |
| cccgcccccg ggcccgactg cgcgtgcccg gccggagccg cgcccctcc tcagggaagg | 1440 |
| ccgggcgtcc ggcccacgag gccgagctcc ccccggccc gggcctctca ccggcgcggg | 1500 |
| gggcgggcca gggggcgggc cggactcgag cggggcggg ctcgcgccag cgcccccagc | 1560 |
| tccgtggcgg cttcgcccgc gagtccagag gcaggcgagc agctcggtcg cccccaccgg | 1620 |
| cccc | 1624 |

<210> SEQ ID NO 5
<211> LENGTH: 4490
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctacgta gccatgctct | 180 |
| aggaagatcg gaattcgccc ttaagtcatg gagaagaccc accttgcaga tgtcctcact | 240 |
| ggggctggca gagccggcaa cctgcccaag gctgctcagt ccattaggag ccagtagcct | 300 |
| ggaagatgtc tttaccccca gcatcagttc aagtggagca gcacataact cttgccctct | 360 |
| gccttccaag attctggtgc tgagacttat ggagtgtctt ggaggttgcc ttctgccccc | 420 |
| caaccctgct cccagctggc cctcccaggc ctgggttgct ggcctctgct ttatcaggat | 480 |
| tctcaagagg gacagctggt ttatgttgca tgactgttcc ctgcatatct gctctggttt | 540 |
| taaatagctt atctgagcag ctggaggacc acatgggctt atatggcgtg gggtacatgt | 600 |
| tcctgtagcc ttgtccctgg cacctgccaa aatagcagcc aacacccccc accccaccg | 660 |
| ccatcccct gccccacccg tccctgtcg cacattcctc cctccgcagg gctggctcac | 720 |
| caggccccag cccacatgcc tgcttaaagc cctctccatc ctctgcctca ccagtcccc | 780 |
| gctgagactg agcagacgcc tccagccacc atggctgctc ctggtgctcc tgccgagtac | 840 |
| ggctacatca gaacagtgct gggccagcag atcctgggac agctggattc tagctctctg | 900 |
| gccctgcctt ctgaggccaa gctgaaactg gccggcagtt ctggaagagg cggccagaca | 960 |
| gtgaagtccc tgcggatcca agaacaggtg cagcagaccc tggccagaaa gggcagatct | 1020 |
| tctgtcggca acggcaacct gcacagaacc agctctgtgc ccgagtacgt gtacaatctg | 1080 |
| cacctggtgg aaaacgactt cgtcggcggc agatccctg tgcctaagac ctacgatatg | 1140 |
| ctgaaggccg gcaccaccgc cacctatgaa ggcagatggg gaagaggcac agcccagtac | 1200 |
| agcagccaga aaagcgtgga agagagaagc ctgcggcacc tctgcggag actggaaatc | 1260 |
| agccctgata gcagcccaga gagagccacc tacacccaca gcgactacca gtactcccag | 1320 |
| agatctcagg ccggccacac actgcaccac caagagtcta aagggccgc tctgctggtg | 1380 |
| cctcctagat acgccagatc tgagatcgtg ggcgtgtcca gagccggcac aacaagcaga | 1440 |
| cagagacact tcgacaccta ccaccggcag tatcagcacg cagcgtgtc cgataccgtg | 1500 |
| ttcgatagca tccccgccaa tcctgctctg ctgacatacc ctagacctgg cacctccaga | 1560 |

```
tccatgggca atctgctgga aaaagagaac tacctgaccg ccggactgac cgtgggacaa      1620
gttcgacctc tggttcctct gcagcccgtg acacagaaca gagccagcag aagcagctgg      1680
caccagtcca gcttccacag caccagaaca ctgagagaag ctggccctag cgtggccgtg      1740
gattcttctg gtagaagggc tcacctgaca gttggccaag cagctgcagg cggaagcgga      1800
aatctgctga ccgagagaag caccttcacc gacagccagc tgggcaacgc cgacatggaa      1860
atgacactgg aacgggccgt gtccatgctg aagccgatc acatgctgcc cagcagaatt       1920
agcgccgctg ccacctttat ccagcacgag tgcttccaga gtctgaggc ccggaagaga       1980 gtgaaccagc tgagaggcat cctgaagctg ctgcagctcc tgaaggtgca gaacgaggat      2040
gtgcagaggg ctgtgtgtgg ggccctgaga aatctggtgt tcgaggacaa cgacaacaag      2100
ctggaagtgg ccgagctgaa cggcgtgcca agactgctgc aggttctgaa acagacccgc      2160
gacctggaaa caaagaagca gatcaccggc ctgctctgga acctgagcag caacgacaag      2220
ctgaagaacc tgatgatcac agaggccctg ctgaccctga cagagaacat catcatccct      2280
ttcagcggct ggcccgaggg cgattaccct aaagctaatg gcctgctgga cttcgacatc      2340
ttctacaacg tgaccggctg cctgagaaac atgtctagcg ctggcgccga tgcagaaag      2400 gccatgagaa gatgtgacgg cctgatcgac agcctggtgc actatgtgcg gggcacaatc      2460
gccgattacc agcctgatga taaggccacc gagaactgcg tgtgcatcct gcacaacctg      2520
agctaccagc tggaagcaga gctgcccgag aagtacagcc agaacatcta catccagaac      2580
cggaacatcc agaccgacaa caacaagagc atcggctgct cggcagccg cagccggaaa      2640 gtgaaagaac agtaccagga cgtgcccatg cctgaggaaa agtctaaccc caaaggcgtg      2700
gaatggctgt ggcacagcat cgtgatccgg atgtacctga gcctgatcgc caagagcgtg      2760
cggaattaca cccaagaggc atctctgggc gccctgcaga atctgacagc aggatctggc      2820
cctatgccta cctctgtggc tcagaccgtg gtgcagaaag agtctggcct gcagcacacc      2880
cggaagatgc tgcatgtggg agatcccagc gtgaagaaaa ccgccatcag cctgctgaga      2940
aacctgagcc ggaatctgtc tctgcagaat gagatcgcca agagacact gcccgacctg      3000 gtgtctatca tccctgacac cgtgcctagc accgacctgc tgattgagac aacagccagc      3060
gcctgctaca ccctgaacaa catcattcag aactcctacc agaacgcccg cgatctgctg      3120
aacacaggcg catccagaa atcatggcc atctctgccg cgacgccta cgcctctaac       3180 aaggcctcta agccgccag cgtgctgctg tattctctgt gggcccatac cgagctgcac      3240
catgcctata agaaggccca gttcaaaaag accgacttcg tgaacagccg gaccgccaag      3300
gcctaccact ctctgaaaga tgtcgacgga tccggtaccg attacaagga cgacgatgac      3360
aagggcagcg cgccacaaa cttctctctg ctaaagcaag caggtgatgt tgaagaaaac      3420
cccgggcctg gctccggcga gggcagggga agtcttctaa catgcgggga cgtggaggaa      3480
aatcccggcc caatggtgag caagggcgag gagctgttca ccggggtggt gcccatcctg      3540
gtcgagctgg acggcgacgt aaacggccac aagttcagcg tgtccggcga gggcgagggc      3600
gatgccacct acggcaagct gaccctgaag ttcatctgca ccaccggcaa gctgcccgtg      3660
ccctggccca ccctcgtgac cacccctgacc tacggcgtgc agtgcttcag ccgctacccc      3720
gaccacatga agcagcacga cttcttcaag tccgccatgc ccgaaggcta cgtccaggag      3780
cgcaccatct tcttcaagga cgacggcaac tacaagaccc gcgccgaggt gaagttcgag      3840
ggcgacaccc tggtgaaccg catcgagctg aagggcatcg acttcaagga ggacggcaac      3900
```

-continued

```
atcctggggc acaagctgga gtacaactac aacagccaca acgtctatat catggccgac      3960
aagcagaaga acggcatcaa ggtgaacttc aagatccgcc acaacatcga ggacggcagc      4020
gtgcagctcg ccgaccacta ccagcagaac acccccatcg gcgacggccc cgtgctgctg      4080
cccgacaacc actacctgag cacccagtcc gccctgagca agacccccaa cgagaagcgc      4140
gatcacatgg tcctgctgga gttcgtgacc gccgccggga tcactctcgg catggacgag      4200
ctgtacaagt aaagcttaat aaaagatctt tattttcatt agatctgtgt gttggttttt      4260
tgtgtgctgg ggactcgagt taagggcgaa ttcccgataa ggatcttcct agagcatggc      4320
tacgtagata agtagcatgg cgggttaatc attaactaca aggaacccct agtgatggag      4380
ttggccactc cctctctgcg cgctcgctcg ctcactgagg ccgggcgacc aaaggtcgcc      4440
cgacgcccgg gctttgcccg gcggcctca gtgagcgagc gagcgcgcag                 4490
```

<210> SEQ ID NO 6
<211> LENGTH: 4662
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
ctgcgcgctc gctcgctcac tgaggccgcc cgggcaaagc ccgggcgtcg ggcgaccttt        60
ggtcgcccgg cctcagtgag cgagcgagcg cgcagagagg gagtggccaa ctccatcact      120
aggggttcct tgtagttaat gattaacccg ccatgctact tatctacgta gccatgctct      180
aggaagatcg gaattcgccc ttaacatctc agcatcatgg ttggatgttt ccacctggct      240
acataagcaa gctttacaca aggtgtaatt tgcctaaata gtggtccatt ctattgtggt      300
gggagcaatt gcttccagga ctcacatcca tatggctccc acttagccat gtggcctgct      360
gacaaagggt ggcggaactg tcactactct gttgtccacg ctttcagtcc tttggttttcc     420 tcttcactcc ctggacgctc atgtaaaaag ggaggccata tacctgtgca ttgtgtgtct      480
aagcattcag tgtgtgtcta aaggcagaag ggtgtgggta ggaaaacaaa gacgagggaa      540
gctgcgttct ccaaacactt cagacttgag taagtggggt tttgcagcaa ttgagtgatt      600
tgagggaaag tgaacataca aacccaagca atcaaaggga atattatctt aataccaggg      660
atacatgttt ttctttctgc ctcttaagtc caaagaggca aatcaggaca gtggctttg      720 gttgtaaact ttaaggtcaa ggatccttc tgttgagctt agctctcaag ttctcagtag      780
tcaactgcgg tgaaacataa ttaatagcac gataaataca agttgtggaa gattcgattg      840
aaagttggag gccctctccg tggatctctc tacaaagagc ctgtaataaa gaggacttaa      900
tcaacgttag cagggctatt taaaaagcat cgtctattaa aattcatttc ttctctagag      960
cctcttgttg gagtttctct gtgtgggtgt gttcgtaaga gaggaatggg ttagcaagag     1020
tactgggtac aatttgtgta tccaagagaa aacagaagct ctcaatgagg aagaacatat     1080
gtttctggga ctgcatctgt gcaaaaagta catagtcctg acgttgtact aagaaaaaaa     1140
acactctctt tagaaagtct tttatttcac acgttatctt cttggcacat ttccctcata     1200
ttgccctttc cgcctgacca aatagccctt tctcaccctc aggtccagga aaaccaggaa     1260
acgtttccaa cagtgcgaca aagcctgact aaccagacat actactcgct cggggatccc     1320
ggaggcaagc ctcagtccaa gaacaggagt gactctcgag ggctcacctg cctgcagggc     1380
agcccctccc tgcatcgagc ggaaatccat cctgtccagc gcggggcgtg ggcagagcgg     1440
```

```
ggcgcggccc cggcaggcgg tatccgctgg gactccgaca acgtgcgcga ccccaggcga      1500
accgcgcccc tctccccacc tccccgcggg cgggtacaag tctccaggtg tccgcgcgct      1560
cagcgggtcc ggcccgcccc cgccccgcc   cccgggcccg actgcgcgtg cccggccgga      1620
gccgcgcccc ctcctcaggg aaggccggc   gtccggccca cgaggccgag ctcccccccg      1680
gcccgggcct ctcaccggcg cggggggcgg gccaggggcg gggccggact cgagcggggc      1740
ggggctcgcg ccagcgcccc cagctccgtg gcggcttcgc ccgcgagtcc agaggcaggc      1800
gagcagctcg gtcgccccca ccggccccat ggctgctcct ggtgctcctg ccgagtacgg      1860
ctacatcaga acagtgctgg gccagcagat cctgggacag ctggattcta gctctctggc      1920
cctgccttct gaggccaagc tgaaactggc cggcagttct ggaagaggcg ccagacagt       1980 gaagtccctg cggatccaag aacaggtgca gcagaccctg gccagaaagg gcagatcttc      2040
tgtcggcaac ggcaacctgc acagaaccag ctctgtgccc gagtacgtgt acaatctgca      2100
cctggtggaa aacgacttcg tcggcggcag atcccctgtg cctaagacct acgatatgct      2160
gaaggccggc accaccgcca cctatgaagg cagatgggga agaggcacag cccagtacag      2220
cagccagaaa agcgtggaag agagaagcct gcggcaccct ctgcggagac tggaaatcag      2280
ccctgatagc agcccagaga gagcccacta caccacagc  gactaccagt actcccagag      2340
atctcaggcc ggccacacac tgcaccacca agagtctaga agggccgctc tgctggtgcc      2400
tcctagatac gccagatctg agatcgtggg cgtgtccaga gccggcacaa caagcagaca      2460
gagacacttc gacacctacc accggcagta tcagcacggc agcgtgtccg ataccgtgtt      2520
cgatagcatc cccgccaatc ctgctctgct gacatacccct agacctggca cctccagatc      2580
catgggcaat ctgctggaaa agagaactaa cctgaccgcc ggactgaccg tgggacaagt      2640
tcgacctctg gttcctctgc agcccgtgac acagaacaga gccagcagaa gcagctggca      2700
ccagtccagc ttccacagca ccagaacact gagagaagct ggccctagcg tggccgtgga      2760
ttcttctggt agaagggctc acctgacagt tggccaagca gctgcaggcg aagcggaaa      2820 tctgctgacc gagagaagca ccttcaccga cagccagctg ggcaacgccg acatggaaat      2880
gacactggaa cgggccgtgt ccatgctgga agccgatcac atgctgccca gcagaattag      2940
cgccgctgcc acctttatcc agcacgagtg cttccagaag tctgaggccc ggaagagagt      3000
gaaccagctg agaggcatcc tgaagctgct gcagctcctg aaggtgcaga acgaggatgt      3060
gcagagggct gtgtgtgggg ccctgagaaa tctggtgttc gaggacaacg acaacaagct      3120
ggaagtggcc gagctgaacg gcgtgccaag actgctgcag gttctgaaac agacccgcga      3180
cctggaaaca aagaagcaga tcaccggcct gctctgaaac ctgagcagca acgacaagct      3240
gaagaacctg atgatcacag aggccctgct gaccctgaca gagaacatca tcatcccttt      3300
cagcggctgg cccgagggcg attaccctaa agctaatggc ctgctggact cgacatctt      3360 ctacaacgtg accggctgcc tgagaaacat gtctagcgct ggcgccgatg cagaaaggc      3420 catgagaaga tgtgacggcc tgatcgacag cctggtgcac tatgtgcggg gcacaatcgc      3480
cgattaccag cctgatgata aggccaccga gaactgcgtg tgcatcctgc acaacctgag      3540
ctaccagctg gaagcagagc tgcccgagaa gtacagccaa acatctacat ccagaaccg      3600 gaacatccag accgacaaca caagagcat  cggctgcttc ggcagccgca gccggaaagt      3660
gaaagaacag taccaggacg tgcccatgcc tgaggaaaag tctaaccccca aggcgtgga      3720 atggctgtgg cacagcatcg tgatccggat gtacctgagc ctgatcgcca agagcgtgcg      3780
gaattacacc caagaggcat ctctgggcgc cctgcagaat ctgacagcag gatctggccc      3840
```

| | |
|---|---|
| tatgcctacc tctgtggctc agaccgtggt gcagaaagag tctggcctgc agcacacccg | 3900 |
| gaagatgctg catgtgggag atcccagcgt gaagaaaacc gccatcagcc tgctgagaaa | 3960 |
| cctgagccgg aatctgtctc tgcagaatga gatcgccaaa gagacactgc ccgacctggt | 4020 |
| gtctatcatc cctgacaccg tgcctagcac cgacctgctg attgagacaa cagccagcgc | 4080 |
| ctgctacacc ctgaacaaca tcattcagaa ctcctaccag aacgcccgcg atctgctgaa | 4140 |
| cacaggcggc atccagaaaa tcatggccat ctctgccggc gacgcctacg cctctaacaa | 4200 |
| ggcctctaaa gccgccagcg tgctgctgta ttctctgtgg gcccatacccg agctgcacca | 4260 |
| tgcctataag aaggcccagt caaaaagac cgacttcgtg aacagccgga ccgccaaggc | 4320 |
| ctaccactct ctgaaagatg tcgacggatc cggtaccgat tacaaggacg acgatgacaa | 4380 |
| gtgaagctta ataaaagatc tttatttttca ttagatctgt gtgttggttt tttgtgtgct | 4440 |
| ggggactcga gttaagggcg aattcccgat aaggatcttc ctagagcatg gctacgtaga | 4500 |
| taagtagcat ggcgggttaa tcattaacta caaggaaccc ctagtgatgg agttggccac | 4560 |
| tccctctctg cgcgctcgct cgctcactga ggccgggcga ccaaaggtcg cccgacgccc | 4620 |
| gggctttgcc cgggcggcct cagtgagcga gcgagcgcgc ag | 4662 |

<210> SEQ ID NO 7
<211> LENGTH: 4682
<212> TYPE: DNA
<213> ORGANISM: Adeno-associated virus

<400> SEQUENCE: 7

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctggagg ggtggagtcg tgacgtgaag tacgtcatag | 180 |
| ggttagggag gtcctgtatt agaggtcacg tgagtgtttt gcgacatttt gcgacaccat | 240 |
| gtggttacgc tgggtattta agcccgagtg agcacgcagg gtctccattt tgaagcggga | 300 |
| ggtttgaacg cgcagccgcc atgccggggt tttacgagat tgtgattaag gtccccagcg | 360 |
| accttgacga gcatctgccc ggtatttctg acagctttgt gaactgggtg gccgagaaag | 420 |
| aatgggagtt gccgccagat tctgacatgg atctgaatct gattgagcag gcaccctga | 480 |
| ccgtagccga gaaactgcag cgcgactttc tgacagaatg gcgccgtgtg agtaaggccc | 540 |
| ccgaggccct ctttttttgtg caatttgaaa agggagagag ctacttccac atgcacgtgc | 600 |
| tggtggagac caccggggtg aagtccatgg ttttgggacg tttcctgagt cagattcgcg | 660 |
| aaaaactgat tcagagaatt taccgcggga tcgagccgac tttgccaaat tggttcgcgg | 720 |
| tcacaaagac ccgaaatggc gccggaggcg ggaacaaggt ggtggacgag tgctacatcc | 780 |
| ccaattacct gctccctaaa acccagcctg agctccagtg ggcgtggact aatatggaac | 840 |
| agtatttaag cgcctgtttg aacctcgcgg agcgtaaacg gttggtggcg cagcatctga | 900 |
| cgcacgtgtc gcagacccag gagcagaaca agaaaatca gaatcccaat tctgacgcgc | 960 |
| cggtgatcag atcaaaaacc tcagccaggt acatggagct ggtcgggtgg ctcgtggaca | 1020 |
| agggattac ctccgagaaa cagtggatc aggaggacca ggcttcatac atctccttca | 1080 |
| atgcggcctc caactcgcgg tctcaaatca aggctgctct ggacaatgcg ggaaagatta | 1140 |
| tgagcctcac taaaaccgcc ccgactacc tggtgggcca gcagcccgtg gaggacattt | 1200 |
| ccggcaatcg gatttataaa atcttggaac tgaacgggta cgatcccaa tacgcggctt | 1260 |

```
ccgtctttct gggatgggcc acgaaaaagt tcggcaagag gaacaccatc tggctgtttg    1320
ggcctgcaac taccgggaag accaacatcg cggaggccat agcccacacg gtgcccttct    1380
acgggtgcgt aaactggacc aacgagaact ttcccttaa cgactgcgtc gacaagatgg     1440
tgatttggtg ggaggagggg aagatgaccg ccaaggtcgt ggaatcggcc aaagccattc    1500
tcggaggaag caaggtgcgc gtggaccaga aatgcaagtc ctcggcccag atagacccga    1560
ctcccgtgat cgtcacctcc aacaccaaca tgtgcgccgt gattgacggg aactcaacga    1620
ccttcgagca ccagcagccg ttgcaagacc ggatgttcaa atttgaactc acccgccgtc    1680
tggatcatga ctttgggaag gtcaccaagc aggaagtcaa agactttttc cggtgggcaa    1740
aggatcacgt ggttgaggtg gagcatgaat tctacgtcaa aaagggtgga gctaagaaaa    1800
ggcccgcccc cagtgacgca gatataagtg agcccaaacg ggcgcgcgag tcagttgcgc    1860
agacatcgac gtcagacgcg gaagcttcga tcaactacgc ggacaggtac caaaacaaat    1920
gttctcgtca cgtgggcatg aatctgatgc tgtttccgtg caaaacctgc gagagaatga    1980
atcagatttc aaatgtctgt ttcacgcacg gtgtcaaaga ctgtggggag tgctttcccg    2040
tgtcaaaatc tcaacccgtt tctgtcgtca aaaagaagac ttatcagaaa ctgtgtccaa    2100
ttcatcacat tttgggaaga gcacccgaga ttgcgtgttc ggcctgcgat atggccaatg    2160
tggacttgga tgactgtgtt tctgaacaat aaatgactta aaccaggtat ggctgccgat    2220
ggttatcttc cagattggct cgaggacaac ctcagtgaag gaattcgcga gtggtgggct    2280
ttgaaacctg gagcccctca acccaaggca aatcaacaac atcaagacaa cgctcggggt    2340
cttgtgcttc cgggttacaa ataccttgga cccggcaacg gactcgacaa gggggagccg    2400
gtcaacgcag cagacgcggc ggccctcgag cacgacaagg catacgacaa gcagctcaag    2460
gccggagaca acccgtacct caagtacaac cacgccgacg cggagtttca ggagcgtctt    2520
aaagaagata cgtcttttgg gggcaacctc ggacgagcag tcttccaggc gaaaaagagg    2580
gttctcgaac ctctgggcct ggttgaggaa cctgttaaga cggctccggg aaaaaagagg    2640
ccggtagagc actctcctgc ggagccagat tcctcctccg gaactggaaa gtcgggccaa    2700
cagcctgcaa gaaaaagatt gaattttggt cagactggag acgcagactc cgtacctgac    2760
ccccagcctc tcggacagcc accagcagcc ccctctggtc tgggatctac tacaatggct    2820
acaggcagtg gcgcaccaat ggcagacaat aacgagggtg ccgatggagt gggtaattcc    2880
tcaggaaatt ggcattgcga ttcccaatgg ctgggcgaca gagtcatcac caccagcacc    2940
cgaacctggg ccctgcccac ctacaacaat cacctctaca agcaaatctc cagccaatca    3000
ggagcttcga acgacaacca ctactttggc tacagcaccc cttgggggta ttttgacttc    3060
aacagattcc actgccactt ttcaccacgt gactggcaaa gactcatcaa caacaactgg    3120
ggattccgac ccaagagact caacttcaag ctctttaaca ttcaagtcaa agaggtcacg    3180
cagaatgacg gtacgacgac gattgccaat aaccttacca gcacggttca ggtgtttact    3240
gactcggagt accagctccc gtacgtcctc ggctcggcgc atcaaggatg cctcccgccg    3300
tttccagcgg acgtcttcat ggtgccacag tatggatacc tcaccctaaa caacgggagt    3360
caggcggtag gacgctcttc cttttactgc ctggagtact tccttctca gatgctgcgt    3420 acaggaaaca actttcagtt cagctacact tttgaagacg tgcctttcca cagcagctac    3480
gctcacagcc agagtctgga tcggctaatg aatcctctga tcgaccagta cctgtattat    3540
ctaaacagga cacaaacagc cagtggaact cagcagtctc ggctactgtt tagccaagct    3600
ggacccacca gcatgtctct tcaagctaaa aactggctgc ctggaccttg ctacagacaa    3660
```

```
cagcgtttgt caaagcaggc aaacgacaac aacaatagca actttccctg gactgcggct    3720
acaaagtacc acctcaatgg cagagactct ctggtgaatc cgggccctgc tatggccagt    3780
cacaaagacg atgaagaaaa gttttcccc atgcatggaa ccctgatatt tggtaaagaa     3840
ggaacaaatg ctaccaacgc ggatttggac aatgtcatga ttacagatga agaagaaatc    3900
cgcaccacaa atcctgtagc tacggagcag tatggatatg tgtcaaataa tttgcaaaac    3960
tcaaatactg ctgcaactac tgaaactgtc aatcaccaag gagcgttacc tggtatggtg    4020
tggcaggata gagacgtgta cctgcaggga cccatttggg ccaaaattcc tcacaccgat    4080
ggacactttc atccttctcc gctgatggga ggttttggac tcaaacaccc acctcctcag    4140
atcatgatca aaacactcc cgttccagcc aatcctccca caaactttag tgcggcaaag     4200
tttgcttctt tcatcacaca gtattccacg gggcaagtca gcgtggagat cgagtgggag    4260
ctgcagaagg agaacagcaa acgctggaac cccgagatcc agtacacttc caactacaac    4320
aaatctgtta atgtggactt tactgtggac actaatggtg tgtattcaga gcctcgcccc    4380
attggcacca gataccctga tcgtaatctg taattgcttg ttaattaata aaccgtttaa    4440
ttcgtttcag ttaaactttg gtctctgcgt acttctttct tatctagttt ccatggctac    4500
gtagataagt accatggcgg gttaatcatt aactctaagg aacccctagt gatggagttg    4560
gccactccct ctctgcgcgc tcgctcgctc actgaggccg cccgggcaaa gcccgggcgt    4620
cgggcgacct ttggtcgccc ggcctcagtg agcgagcgag cgcgcagaga gggagtggcc    4680
aa                                                                   4682
```

<210> SEQ ID NO 8
<211> LENGTH: 837
<212> TYPE: PRT
<213> ORGANISM: Homo sapiens

<400> SEQUENCE: 8

```
Met Ala Ala Pro Gly Ala Pro Ala Glu Tyr Gly Tyr Ile Arg Thr Val
  1               5                  10                  15

Leu Gly Gln Gln Ile Leu Gly Gln Leu Asp Ser Ser Leu Ala Leu
                 20                  25                  30

Pro Ser Glu Ala Lys Leu Lys Leu Ala Gly Ser Ser Arg Gly Gly
         35                  40                  45

Gln Thr Val Lys Ser Leu Arg Ile Gln Glu Gln Val Gln Gln Thr Leu
     50                  55                  60

Ala Arg Lys Gly Arg Ser Ser Val Gly Asn Gly Asn Leu His Arg Thr
 65                  70                  75                  80

Ser Ser Val Pro Glu Tyr Val Tyr Asn Leu His Leu Val Glu Asn Asp
                 85                  90                  95

Phe Val Gly Gly Arg Ser Pro Val Pro Lys Thr Tyr Asp Met Leu Lys
                100                 105                 110

Ala Gly Thr Thr Ala Thr Tyr Glu Gly Arg Trp Gly Arg Gly Thr Ala
            115                 120                 125

Gln Tyr Ser Ser Gln Lys Ser Val Glu Glu Arg Ser Leu Arg His Pro
        130                 135                 140

Leu Arg Arg Leu Glu Ile Ser Pro Asp Ser Pro Glu Arg Ala His
145                 150                 155                 160

Tyr Thr His Ser Asp Tyr Gln Tyr Ser Gln Arg Ser Gln Ala Gly His
                165                 170                 175

Thr Leu His His Gln Glu Ser Arg Arg Ala Ala Leu Leu Val Pro Pro
```

```
            180                 185                 190
Arg Tyr Ala Arg Ser Glu Ile Val Gly Val Ser Arg Ala Gly Thr Thr
            195                 200                 205

Ser Arg Gln Arg His Phe Asp Thr Tyr His Arg Gln Tyr Gln His Gly
            210                 215                 220

Ser Val Ser Asp Thr Val Phe Asp Ser Ile Pro Ala Asn Pro Ala Leu
225                 230                 235                 240

Leu Thr Tyr Pro Arg Pro Gly Thr Ser Arg Ser Met Gly Asn Leu Leu
                    245                 250                 255

Glu Lys Glu Asn Tyr Leu Thr Ala Gly Leu Thr Val Gly Gln Val Arg
            260                 265                 270

Pro Leu Val Pro Leu Gln Pro Val Thr Gln Asn Arg Ala Ser Arg Ser
            275                 280                 285

Ser Trp His Gln Ser Ser Phe His Ser Thr Arg Thr Leu Arg Glu Ala
            290                 295                 300

Gly Pro Ser Val Ala Val Asp Ser Ser Gly Arg Arg Ala His Leu Thr
305                 310                 315                 320

Val Gly Gln Ala Ala Ala Gly Gly Ser Gly Asn Leu Leu Thr Glu Arg
                    325                 330                 335

Ser Thr Phe Thr Asp Ser Gln Leu Gly Asn Ala Asp Met Glu Met Thr
                    340                 345                 350

Leu Glu Arg Ala Val Ser Met Leu Glu Ala Asp His Met Leu Pro Ser
            355                 360                 365

Arg Ile Ser Ala Ala Thr Phe Ile Gln His Glu Cys Phe Gln Lys
            370                 375                 380

Ser Glu Ala Arg Lys Arg Val Asn Gln Leu Arg Gly Ile Leu Lys Leu
385                 390                 395                 400

Leu Gln Leu Leu Lys Val Gln Asn Glu Asp Val Gln Arg Ala Val Cys
                    405                 410                 415

Gly Ala Leu Arg Asn Leu Val Phe Glu Asp Asn Asp Asn Lys Leu Glu
                    420                 425                 430

Val Ala Glu Leu Asn Gly Val Pro Arg Leu Leu Gln Val Leu Lys Gln
            435                 440                 445

Thr Arg Asp Leu Glu Thr Lys Lys Gln Ile Thr Gly Leu Leu Trp Asn
            450                 455                 460

Leu Ser Ser Asn Asp Lys Leu Lys Asn Leu Met Ile Thr Glu Ala Leu
465                 470                 475                 480

Leu Thr Leu Thr Glu Asn Ile Ile Ile Pro Phe Ser Gly Trp Pro Glu
                    485                 490                 495

Gly Asp Tyr Pro Lys Ala Asn Gly Leu Leu Asp Phe Asp Ile Phe Tyr
                    500                 505                 510

Asn Val Thr Gly Cys Leu Arg Asn Met Ser Ser Ala Gly Ala Asp Gly
            515                 520                 525

Arg Lys Ala Met Arg Arg Cys Asp Gly Leu Ile Asp Ser Leu Val His
            530                 535                 540

Tyr Val Arg Gly Thr Ile Ala Asp Tyr Gln Pro Asp Asp Lys Ala Thr
545                 550                 555                 560

Glu Asn Cys Val Cys Ile Leu His Asn Leu Ser Tyr Gln Leu Glu Ala
                    565                 570                 575

Glu Leu Pro Glu Lys Tyr Ser Gln Asn Ile Tyr Ile Gln Asn Arg Asn
                    580                 585                 590

Ile Gln Thr Asp Asn Asn Lys Ser Ile Gly Cys Phe Gly Ser Arg Ser
            595                 600                 605
```

```
Arg Lys Val Lys Glu Gln Tyr Gln Asp Val Pro Met Pro Glu Glu Lys
            610                 615                 620

Ser Asn Pro Lys Gly Val Glu Trp Leu Trp His Ser Ile Val Ile Arg
625                 630                 635                 640

Met Tyr Leu Ser Leu Ile Ala Lys Ser Val Arg Asn Tyr Thr Gln Glu
                645                 650                 655

Ala Ser Leu Gly Ala Leu Gln Asn Leu Thr Ala Gly Ser Gly Pro Met
            660                 665                 670

Pro Thr Ser Val Ala Gln Thr Val Gln Lys Glu Ser Gly Leu Gln
            675                 680                 685

His Thr Arg Lys Met Leu His Val Gly Asp Pro Ser Val Lys Lys Thr
            690                 695                 700

Ala Ile Ser Leu Leu Arg Asn Leu Ser Arg Asn Leu Ser Leu Gln Asn
705                 710                 715                 720

Glu Ile Ala Lys Glu Thr Leu Pro Asp Leu Val Ser Ile Ile Pro Asp
                725                 730                 735

Thr Val Pro Ser Thr Asp Leu Leu Ile Glu Thr Ala Ser Ala Cys
            740                 745                 750

Tyr Thr Leu Asn Asn Ile Ile Gln Asn Ser Tyr Gln Asn Ala Arg Asp
                755                 760                 765

Leu Leu Asn Thr Gly Gly Ile Gln Lys Ile Met Ala Ile Ser Ala Gly
770                 775                 780

Asp Ala Tyr Ala Ser Asn Lys Ala Ser Lys Ala Ala Ser Val Leu Leu
785                 790                 795                 800

Tyr Ser Leu Trp Ala His Thr Glu Leu His His Ala Tyr Lys Lys Ala
                805                 810                 815

Gln Phe Lys Lys Thr Asp Phe Val Asn Ser Arg Thr Ala Lys Ala Tyr
            820                 825                 830

His Ser Leu Lys Asp
        835

<210> SEQ ID NO 9
<211> LENGTH: 540
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
tcaacctctg gattacaaaa tttgtgaaag attgactggt attcttaact atgttgctcc    60
ttttacgcta tgtggatacg ctgctttaat gcctttgtat catgctattg cttcccgtat   120
ggctttcatt ttctcctcct tgtataaatc ctggttgctg tctctttatg aggagttgtg   180
gcccgttgtc aggcaacgtg gcgtggtgtg cactgtgttt gctgacgcaa cccccactgg   240
ttggggcatt gccaccacct gtcagctcct tccgggact ttcgctttcc ccctccctat    300
tgccacggcg gaactcatcg ccgcctgcct tgcccgctgc tggacagggg ctcggctgtt   360
gggcactgac aattccgtgg tgttgtcggg gaaatcatcg tcctttcctt ggctgctcgc   420
ctgtgttgcc acctggattc tgcgcgggac gtccttctgc tacgtccctt cggccctcaa   480
tccagcggac cttccttccc gcggcctgct gccggctctg cggcctcttc gcgtcttcg    540

<210> SEQ ID NO 10
<211> LENGTH: 221
<212> TYPE: DNA
```

```
<213> ORGANISM: Artificial Sequence
<220> FEATURE:
<223> OTHER INFORMATION: Description of Artificial Sequence: Synthetic
      polynucleotide

<400> SEQUENCE: 10
cctcgactgt gccttctagt tgccagccat ctgttgtttg cccctccccc gtgccttcct      60
tgaccctgga aggtgccact cccactgtcc tttcctaata aaatgaggaa attgcatcgc     120
attgtctgag taggtgtcat tctattctgg ggggtggggt ggggcaggac agcaaggggg     180
aggattggga agacaatagc aggcatgctg gggactgggg a                         221

<210> SEQ ID NO 11
<211> LENGTH: 855
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
tcaacctctg gattacaaaa tttgtgaaag attgactggt attcttaact atgttgctcc      60
ttttacgcta tgtggatacg ctgctttaat gcctttgtat catgctattg cttcccgtat     120
ggctttcatt ttctcctcct tgtataaatc ctggttgctg tctctttatg aggagttgtg     180
gcccgttgtc aggcaacgtg gcgtggtgtg cactgtgttt gctgacgcaa ccccactgg      240 ttggggcatt gccaccacct gtcagctcct ttccgggact ttcgctttcc ccctccctat     300
tgccacggcg gaactcatcg ccgcctgcct tgcccgctgc tggacagggg ctcggctgtt     360
gggcactgac aattccgtgg tgttgtcggg gaaatcatcg tcctttcctt ggctgctcgc     420
ctgtgttgcc acctggattc tgcgcgggac gtccttctgc tacgtccctt cggccctcaa     480
tccagcggac cttccttccc gcggcctgct gccggctctg cggcctcttc cgcgtcttcg     540
agatctgcct cgactgtgcc ttctagttgc cagccatctg ttgtttgccc ctcccccgtg     600
ccttccttga ccctggaagg tgccactccc actgtccttt cctaataaaa tgaggaaatt     660
gcatcgcatt gtctgagtag gtgtcattct attctggggg gtggggtggg gcaggacagc     720
aagggggagg attgggaaga caatagcagg catgctgggg actggggact cgagttaagg     780
gcgaattccc gataaggatc ttcctagagc atggctacgt agataagtag catggcgggt     840
taatcattaa ctaca                                                      855
```